US010098958B2

(12) United States Patent
Mirkin et al.

(10) Patent No.: US 10,098,958 B2
(45) Date of Patent: Oct. 16, 2018

(54) DELIVERY OF OLIGONUCLEOTIDE FUNCTIONALIZED NANOPARTICLES

(71) Applicant: NORTHWESTERN UNIVERSITY, Evanston, IL (US)

(72) Inventors: Chad A. Mirkin, Wilmette, IL (US); Amy S. Paller, Wilmette, IL (US); David A. Giljohann, Chicago, CA (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 13/721,366

(22) Filed: Dec. 20, 2012

(65) Prior Publication Data

US 2013/0172404 A1 Jul. 4, 2013

Related U.S. Application Data

(63) Continuation of application No. 12/724,395, filed on Mar. 15, 2010, now abandoned, and a continuation-in-part of application No. 12/684,836, filed on Jan. 8, 2010, now abandoned.

(60) Provisional application No. 61/187,759, filed on Jun. 17, 2009, provisional application No. 61/143,293, filed on Jan. 8, 2009, provisional application No. 61/169,384, filed on Apr. 15, 2009.

(51) Int. Cl.
| | |
|---|---|
| *A61K 48/00* | (2006.01) |
| *C12N 15/113* | (2010.01) |
| *A61K 47/48* | (2006.01) |
| *A61K 9/50* | (2006.01) |
| *A61K 31/00* | (2006.01) |
| *B82Y 5/00* | (2011.01) |
| *A61K 9/00* | (2006.01) |

(52) U.S. Cl.
CPC ...... *A61K 47/48015* (2013.01); *A61K 9/5094* (2013.01); *A61K 31/00* (2013.01); *A61K 47/48861* (2013.01); *B82Y 5/00* (2013.01); *A61K 9/0014* (2013.01)

(58) Field of Classification Search
CPC .............. C12N 15/111; C12N 2310/11; C12N 2320/32; A61K 31/00; A61K 48/00
USPC ....... 435/6, 91.1, 91.31, 455, 458, 6.1, 6.11, 435/6.12, 4; 514/1, 2, 44; 536/23.1, 536/24.5, 24.31; 977/773, 906
See application file for complete search history.

(56) References Cited

U.S. PATENT DOCUMENTS

| | | |
|---|---|---|
| 3,687,808 A | 8/1972 | Merigan et al. |
| 4,179,337 A | 12/1979 | Davis et al. |
| 4,289,872 A | 9/1981 | Denkewalter et al. |
| 4,301,144 A | 11/1981 | Iwashita et al. |
| 4,469,863 A | 9/1984 | Ts'o et al. |
| 4,476,301 A | 10/1984 | Imbach et al. |
| 4,489,055 A | 12/1984 | Couvreur et al. |
| 4,496,689 A | 1/1985 | Mitra |
| 4,587,044 A | 5/1986 | Miller et al. |
| 4,605,735 A | 8/1986 | Miyoshi et al. |
| 4,640,835 A | 2/1987 | Shimizu et al. |
| 4,667,025 A | 5/1987 | Miyoshi et al. |
| 4,670,417 A | 6/1987 | Iwasaki et al. |
| 4,762,779 A | 8/1988 | Snitman |
| 4,789,737 A | 12/1988 | Miyoshi et al. |
| 4,791,192 A | 12/1988 | Nakagawa et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,229,490 A | 7/1993 | Tam |
| 5,235,033 A | 8/1993 | Summerton et al. |
| 5,245,022 A | 9/1993 | Weis et al. |

(Continued)

FOREIGN PATENT DOCUMENTS

| | | |
|---|---|---|
| EP | 1072679 | 1/2001 |
| EP | 1674128 | 6/2006 |

(Continued)

OTHER PUBLICATIONS

McKenzie et al (Small, vol. 3, No. 11, pp. 1866-1868 (2007).*

(Continued)

*Primary Examiner* — Jane J Zara
(74) *Attorney, Agent, or Firm* — Marshall, Gerstein & Borun LLP

(57) ABSTRACT

The present invention relates to compositions and methods for delivering an oligonucleotide-functionalized nanoparticle.

22 Claims, 6 Drawing Sheets

Specification includes a Sequence Listing.

(56) References Cited

U.S. PATENT DOCUMENTS

| | | |
|---|---|---|
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,270,163 A | 12/1993 | Gold et al. |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,272 A | 10/1995 | Hooykaas |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,547,842 A | 8/1996 | Hogan et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,637,459 A | 6/1997 | Burke et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,287,860 B1 | 9/2001 | Monia et al. |
| 6,361,944 B1 | 3/2002 | Mirkin et al. |
| 6,403,312 B1 | 6/2002 | Dahiyat et al. |
| 6,417,340 B1 | 7/2002 | Mirkin et al. |
| 6,495,324 B1 | 12/2002 | Mirkin et al. |
| 6,506,564 B1 | 1/2003 | Mirkin et al. |
| 6,544,776 B1 | 4/2003 | Gold et al. |
| 6,582,921 B2 | 6/2003 | Elghanian et al. |
| 6,602,669 B2 | 8/2003 | Letsinger et al. |
| 6,610,491 B2 | 8/2003 | Mirkin et al. |
| 6,656,730 B1 | 12/2003 | Manoharan |
| 6,677,122 B2 | 1/2004 | Mirkin et al. |
| 6,677,153 B2 | 1/2004 | Iversen |
| 6,678,548 B1 | 1/2004 | Echauz et al. |
| 6,682,895 B2 | 1/2004 | Mirkin et al. |
| 6,709,825 B2 | 3/2004 | Mirkin et al. |
| 6,720,147 B2 | 4/2004 | Mirkin et al. |
| 6,720,411 B2 | 4/2004 | Mirkin et al. |
| 6,750,016 B2 | 6/2004 | Mirkin et al. |
| 6,759,199 B2 | 7/2004 | Mirkin et al. |
| 6,767,702 B2 | 7/2004 | Mirkin |
| 6,773,884 B2 | 8/2004 | Mirkin et al. |
| 6,777,186 B2 | 8/2004 | Mirkin et al. |
| 6,812,334 B1 | 11/2004 | Mirkin et al. |

(56) References Cited

U.S. PATENT DOCUMENTS

| | | |
|---|---|---|
| 6,818,753 B2 | 11/2004 | Mirkin et al. |
| 6,827,979 B2 | 12/2004 | Mirkin et al. |
| 6,828,432 B2 | 12/2004 | Mirkin et al. |
| 6,844,161 B2 | 1/2005 | Siani et al. |
| 6,861,221 B2 | 3/2005 | Mirkin et al. |
| 6,878,814 B2 | 4/2005 | Mirkin et al. |
| 6,974,669 B2 | 12/2005 | Mirkin et al. |
| 6,991,900 B2 | 1/2006 | Shizuya |
| 7,001,616 B2 | 2/2006 | Batich et al. |
| 7,098,320 B1 | 8/2006 | Mirkin et al. |
| 7,223,833 B1 | 5/2007 | Nielsen et al. |
| 7,238,472 B2 | 7/2007 | Mirkin et al. |
| 7,323,309 B2 | 1/2008 | Mirkin et al. |
| 7,332,586 B2 | 2/2008 | Franzen et al. |
| 7,611,728 B2 | 11/2009 | Kidane et al. |
| 7,638,557 B2 | 12/2009 | Lipkin et al. |
| 7,667,004 B2 | 2/2010 | Zhong et al. |
| 7,727,969 B2 | 6/2010 | Farokhzad et al. |
| 2002/0172953 A1 | 11/2002 | Mirkin et al. |
| 2003/0147966 A1 | 8/2003 | Franzen et al. |
| 2003/0181412 A1 | 9/2003 | Erikson |
| 2004/0219565 A1 | 11/2004 | Kauppinen et al. |
| 2004/0247680 A1 | 12/2004 | Farokhzad et al. |
| 2004/0248099 A1 | 12/2004 | Goppelt et al. |
| 2005/0059016 A1 | 3/2005 | Ecker et al. |
| 2005/0074753 A1 | 4/2005 | Goldsborough |
| 2005/0096263 A1 | 5/2005 | Keay et al. |
| 2005/0136258 A1 | 6/2005 | Nie et al. |
| 2005/0197315 A1 | 9/2005 | Taira et al. |
| 2005/0214782 A1 | 9/2005 | Chen et al. |
| 2005/0244858 A1 | 11/2005 | Rossi et al. |
| 2006/0002949 A1 | 1/2006 | Glenn et al. |
| 2006/0008907 A1 | 1/2006 | Friedman et al. |
| 2006/0019917 A1 | 1/2006 | Guerciolini et al. |
| 2006/0025363 A1 | 2/2006 | Breitenbach et al. |
| 2006/0035344 A1 | 2/2006 | Pachuk et al. |
| 2006/0105343 A1 | 5/2006 | Zetter et al. |
| 2006/0159921 A1 | 7/2006 | Murthy et al. |
| 2006/0183247 A1 | 8/2006 | Kim et al. |
| 2006/0188560 A1 | 8/2006 | Cheresh et al. |
| 2006/0233712 A1 | 10/2006 | Penades et al. |
| 2006/0252037 A1 | 11/2006 | Kolesnick et al. |
| 2006/0275371 A1 | 12/2006 | Dai et al. |
| 2007/0105139 A1 | 5/2007 | Nishigaki et al. |
| 2007/0243132 A1* | 10/2007 | Russell-Jones et al. ...... 424/1.11 |
| 2008/0057128 A1 | 3/2008 | Li et al. |
| 2008/0194463 A1 | 8/2008 | Weller et al. |
| 2008/0213177 A1 | 9/2008 | Rademacher et al. |
| 2008/0220072 A1 | 9/2008 | Unger et al. |
| 2008/0279946 A1 | 11/2008 | Hainfeld |
| 2008/0305106 A1 | 12/2008 | Brennan et al. |
| 2008/0306016 A1 | 12/2008 | Mirkin et al. |
| 2008/0317749 A1 | 12/2008 | Kastelein et al. |
| 2008/0317768 A1 | 12/2008 | Bianchi |
| 2009/0035576 A1 | 2/2009 | Prasad et al. |
| 2009/0081244 A1* | 3/2009 | Glenn et al. ............... 424/184.1 |
| 2009/0148384 A1 | 6/2009 | Fischer et al. |
| 2009/0155173 A1 | 6/2009 | Scherman et al. |
| 2009/0209629 A1 | 8/2009 | Mirkin et al. |
| 2009/0286853 A1 | 11/2009 | Gryaznov et al. |
| 2010/0167051 A1 | 7/2010 | Goia et al. |
| 2010/0183504 A1 | 7/2010 | Chen |
| 2010/0183634 A1* | 7/2010 | Luo et al. ................... 424/178.1 |
| 2010/0267814 A1 | 10/2010 | Bennett et al. |
| 2011/0172404 A1* | 7/2011 | Luo et al. ..................... 536/23.1 |
| 2011/0201594 A1* | 8/2011 | Murthi et al. ........... 514/210.21 |
| 2011/0262976 A1 | 10/2011 | Kandula et al. |

FOREIGN PATENT DOCUMENTS

| | | |
|---|---|---|
| EP | 2162117 B1 | 2/2018 |
| WO | WO-1989/002439 | 3/1989 |
| WO | WO-1993/007883 | 4/1993 |
| WO | WO-1993/021259 | 10/1993 |
| WO | WO-1995/006731 | 3/1995 |
| WO | WO-1995/011910 | 5/1995 |
| WO | WO-1997/012896 | 4/1997 |
| WO | WO-1998/004740 | 2/1998 |
| WO | WO-1998/039352 | 9/1998 |
| WO | WO-1998/047343 | 10/1998 |
| WO | WO-1999/011655 | 3/1999 |
| WO | WO-1999/014526 | 3/1999 |
| WO | WO-2000/043045 | 7/2000 |
| WO | WO-2001/000876 | 1/2001 |
| WO | WO-2001/049869 | 7/2001 |
| WO | WO-2001/051665 | 7/2001 |
| WO | WO-2001/073123 | 10/2001 |
| WO | WO-2002/096262 | 12/2002 |
| WO | WO-2003/008539 | 1/2003 |
| WO | WO-2003/030941 A1 | 4/2003 |
| WO | WO-2003/051278 | 6/2003 |
| WO | WO-2003/101386 A2 | 12/2003 |
| WO | WO-2005/079462 | 9/2005 |
| WO | WO-2005/108616 A1 | 11/2005 |
| WO | WO-2005/112619 A2 | 12/2005 |
| WO | WO-2005/116226 | 12/2005 |
| WO | WO-2006/012695 | 2/2006 |
| WO | WO-2006/045541 | 5/2006 |
| WO | WO-2006/064451 | 6/2006 |
| WO | WO-2006/064453 | 6/2006 |
| WO | WO-2006/138145 | 12/2006 |
| WO | WO-2007/047455 | 4/2007 |
| WO | WO-2008/042156 A1 | 4/2008 |
| WO | WO-2008/098248 | 8/2008 |
| WO | WO-2008/141289 | 11/2008 |
| WO | WO-2008/151049 | 12/2008 |
| WO | WO-2010/060110 | 5/2010 |
| WO | WO-2010/081049 | 7/2010 |
| WO | WO-2010/120420 | 10/2010 |
| WO | WO-2011/017690 | 2/2011 |

OTHER PUBLICATIONS

Cui et al, (J. Controlled Release, vol. 81, pp. 173-184 (2002).*
Lin et al, Recent Application of Intronic MicroRNA Agents in Cosmetics, in Current Perspectives in MicroRNAs (miRNA) pp. 51-72 (Springer Science + Business Media B.V. 2008).*
Seferos et al, Nano Lett., vol. 9, No. 1, pp. 308-311 (2009).*
Abou-Alfa et al., Randomized phase III study of exatecan and gemcitabine compared with gemcitabine alone in untreated advanced pancreatic cancer, J. Clin. Oncol., 24(27):4441-7 (2006).
Agasti et al., Photoregulated release of caged anticancer drugs from gold nanoparticles, J. Am. Chem. Soc., 131(16):5728-9 (2009).
Agrawal et al., Antisense therapeutics: Is it as simple as complementary base recognition? Mol. Med. Today, 6: 72-81 (2000).
Ahmadi et al., Shape-controlled synthesis of colloidal platinum nanoparticles. Science, 272(5270): 1924-6 (1996).
Aime et al., Insights into the use of paramagnetic Gd(III) complexes in MR-molecular imaging investigations, J. Magn. Reson. Imaging, 16(4):394-406 (2002).
Aime et al., Pushing the sensitivity envelope of lanthanide-based magnetic resonance imaging (MRI) contrast agents for molecular imaging applications, Acc. Chem. Res., 42(7):822-31 (2009).
Alivisatos et al., Organization of 'nanocrystal molecules' using DNA. Nature, 382: 609-11 (1996).
Alivisatos, The use of nanocrystals in biological detection, Nat. Biotechnol., 22(1):47-52 (2004).
Allara et al., Spontaneously organized molecular assemblies. 1. Formation, dynamics, and physical properties of n-alkanoic acids adsorbed from solution on an oxidized aluminum surface. Langmuir, 1(1): 45-52 (1985).
Allara et al., The study of the gas-solid interaction of acetic acid with a cuprous oxide surface using reflection-absorption spectroscopy. J. Colloid Interface Sci., 49: 410-21 (1974).
Alric et al., Gadolinium chelate coated gold nanoparticles as contrast agents for both X-ray computed tomography and magnetic resonance imaging, J. Am. Chem. Soc., 130(18):5908-15 (2008).
Altieri, Survivin, versatile modulation of cell division and apoptosis in cancer, Oncogene, 22: 8581-9 (2003).

(56) References Cited

OTHER PUBLICATIONS

Altschul et al., Basic local alignment search tool. J. Mol. Biol., 215: 403-10 (1990).
Amirkhanov et al., Design of (Gd-DO3A)n-polydiamidopropanoyl-peptide nucleic acid-D(Cys-Ser-Lys-Cys) magnetic resonance contrast agents. Biopolymers, 89(12): 1061-76 (2008).
Angelini et al., Reversal of P-glycoprotein-mediated multidrug resistance in human sarcoma MES-SA/Dx-5 cells by nonsteroidal anti-inflammatory drugs, Oncol. Rep., 20(4):731-5 (2008).
Anton et al., Design and production of nanoparticles formulated from nano-emulsion templates—a review, J. Control Release, 128(3):185-99 (2008).
Aynie, et al., Spongelike alginate nanoparticles as a new potential system for the delivery of antisense oligonucleotides. Antisense Nucl. Acid Drug Dev., 9: 301-12 (1999).
Bahnemann, Photochemical Conversion and Storage of Solar Energy, Pelizetti and Schiavello (Eds.) pp. 251-276 (1991).
Baker et al., Dendrimer-mediated cell transfection in vitro, Meth. Molec. Biol., 245: 67-81 (2004).
Balasubramanian et al., Biodistribution of gold nanoparticles and gene expression changes in the liver and spleen after intravenous administration in rats, Biomaterials, 31 (8):2034-42 (2010).
Bardeesy et al., Pancreatic cancer biology and genetics, Nat. Rev. Cancer, 2(12):897-909 (2002).
Bath et al., DNA nanomachines, Nat. Nanotechnol., 2: 275-84 (2007).
Baudhuim, Mechanisms of organic transformations on semiconductor particles. Photochemical Conversion and Storage of Solar Energy. Kluwer Academic Publishers. 251-76 (1990).
Baudhuin et al., Molecular interactions between colloidal gold, proteins, and living cells. Chapter 1: 1-17 (1989).
Berton, et al., Highly loaded nanoparticulate carrier using an hydrophobic antisense oligonucleotide complex, Eur. J. Pharma. Sci., 9: 163-70 (1999).
Besch et al., Characterization and quantification of triple helix formation in chromosomal DNA. J. Mol. Biol., 341: 979-89 (2004).
Bharali et al., Organically modified silica nanoparticles: a nonviral vector for in vivo gene delivery and expression in the brain. Proc. Natl. Acad. Sci. USA, 102(32): 11539-44 (2005).
Biancone et al., Magnetic resonance imaging of gadolinium-labeled pancreatic islets for experimental transplantation, NMR Biomed., 20(1):40-8 (2007).
Bielinska et al., DNA complexing with polyamidoamine dendrimers: implications for transfection. Bioconjug Chem., 10(5): 843-50 (1999).
Birck et al., Mutation and allelic loss of the PTEN/MMAC1 gene in primary and metastatic melanoma biopsies, J. Invest. Dermatol., 114: 277-80 (2000).
Bisht et al., Polymeric nanoparticle-encapsulated curcumin ("nanocurcumin"): a novel strategy for human cancer therapy, J. Nanobiotechnology, 5:3 (2007) (18 pages).
Bowman et al., Inhibition of HIV fusion with multivalent gold nanoparticles, J. Am. Chem. Soc., 130(22):6896-7 (2008).
Bramhill, Bacterial cell division, Annu. Rev. Cell Dev. Biol., 13:395-424 (1997).
Bratu et al., Visualizing the distribution and transport of mRNAs in living cells, Proc. Natl. Acad. Sci. USA, 100: 13308-13 (2003).
Brown et al., Surface treatment of the hydrophobic drug danazol to improve drug dissolution, Int. J. Pharmaceutics, 165:227-37 (1998).
Brus, Quantum crystallites and nonlinear optics. Appl. Phys. A. 53(6): 465-74 (1991).
Burwell, Modified silica gels as adsorbents and catalysts. Chem. Technol., 4: 370-7 (1974).
Cao et al., Raman dye-labeled nanoparticle probes for proteins, J. Am. Chem. Soc., 125(48):14676-7 (2003).
Capaccioli et al., Cationic lipids improve antisense oligonucleotide uptake and prevent degradation in cultured cells and inhuman serum, Biochem. Biophys. Res. Commun., 197(2): 818-25 (1993).
Caravan et al., The interaction of MS-325 with human serum albumin and its effect on proton relaxation rates, J. Am. Chem. Soc., 124(12):3152-62 (2002).
Caravan, Strategies for increasing the sensitivity of gadolinium based MRI contrast agents, Chem. Soc. Rev., 35(6):512-23 (2006).
Castoldi et al., A sensitive array for microRNA expression profiling (miChip) based on locked nucleic acids (LNA), RNA. 12: 913-20 (2006).
Cha et al., Hepatocellular carcinoma: current management, Curr. Probl. Surg., 47(1):10-67 (2010).
Chari et al., Immunoconjugates containing novel maytansinoids: promising anticancer drugs, Cancer Res., 52(1):127-31 (1992).
Charreyre et al., Fluorescence energy transfer study of the conformation of oligonucleotides covalently bound to polystyrene latex particles. Langmuir, 13: 3103-10 (1997).
Chavany et al., Polyalkylcyanoacrylate nanoparticles as polymeric carriers for antisense oligonucleotides, Pharma. Res., 9(4): 441-9 (1992).
Chavany, et al., Adsorption of oligonucleotides onto polyisohexylcyanoacrylate nanoparticles protects them against nucleases and increases their cellular uptake. Pharma. Res., 11(9): 1370-8 (1994).
Chen et al., Kinetics and thermodynamics of DNA hybridization on gold nanoparticles, Nucl. Acids Res., 37: 3756-65 (2009).
Chen et al., MDR 1 activation is the predominant resistance mechanism selected by vinblastine in MES-SA cells, Br. J. Cancer, 83(7):892-8 (2000).
Cheng et al., Tandem synthesis of core-shell brush copolymers and their transformation to peripherally cross-linked and hollowed nanostructures, J. Am. Chem. Soc., 128(21):6808-9 (2006).
Cheung et al., Akt3 and mutant V600E B-Raf cooperate to promote early melanoma development, Cancer Res., 68:3429-39 (2008).
Chirila et al., The use of synthetic polymers for delivery of therapeutic antisense oligodeoxynucleotides. Biomaterials, 23: 321-42 (2002).
Chithrani et al., Elucidating the mechanism of cellular uptake and removal of protein-coated gold nanoparticles of different sizes and shapes. Nano Lett., 7: 1542-50 (2007).
Chithrani, et al., Determining the size and shape dependence of gold nanoparticle uptake into mammalian cells, Nano Lett., 6(4): 662-8 (2006).
Chompoosor et al., Charge dependence of ligand release and monolayer stability of gold nanoparticles by biogenic thiols, Bioconjugate Chem., 19:1342-5 (2008).
Chrisey et al., Covalent attachment of synthetic DNA to self-assembled monolayer films, Nucl. Acids Res., 24: 3031-9 (1996).
Chu et al., Effects of photoactivated 5-aminolevulinic acid hexyl ester on MDR1 over-expressing human uterine sarcoma cells, Toxicol. Lett., 181(1):7-12 (2008).
Cload et al., Polyether tethered oligonucleotide probes. J. Am. Chem. Soc., 113(16): 6324-6 (1991).
Connor et al., Gold nanoparticles are taken up by human cells but do not cause acute cytotoxicity, Small, 1(3):325-7 (2005).
Cook, Medicinal chemistry of antisense oligonucleotides—future opportunities. Anticancer Drug Des., 6(6):585-607 (1991).
Crawford et al., A novel B-RAF inhibitor blocks interleukin-8 (IL-8) synthesis in human melanoma xenografts, revealing IL-8 as a potential pharmacodynamic biomarker, Mol. Cancer Ther., 7:492-9 (2008).
Crawford et al., Peptide aptamers: Tools for biology and drug discovery. 2(1): 72-9 (2003).
Crich et al., Improved route for the visualization of stem cells labeled with a Gd-/Eu-chelate as dual (MRI and fluorescence) agent, Magn. Reson. Med., 51(5):938-44 (2004).
Crooke et al., Progress in antisense technology. Ann. Rev. Med., 55: 61-95 (2004).
Curtis et al., A morphology-selective copper organosol. Angew. Chem. Int. Ed. Engl., 27: 1530-3 (1988).
Daniel et al., Gold nanoparticles: assembly, supramolecular chemistry, quantum-size-related properties, and applications toward biology, catalysis, and nanotechnology. Chem Rev., 104(1): 293-346 (2004).

(56) References Cited

OTHER PUBLICATIONS

Dankort et al., A new mouse model to explore the initiation, progression, and therapy of BRAFV600E-induced lung tumors, Genes Dev., 21: 379-84 (2007).
Dankort et al., Braf(V600E) cooperates with Pten loss to induce metastatic melanoma, Nat Genet., 41: 544-52 (2009).
Davies et al., A novel AKT3 mutation in melanoma tumours and cell lines, Br. J. Cancer, 99: 1265-8 (2008).
De Mesmaeker et al., Antisense oligonucleotides. Acc. Chem. Res., 28(9): 366-74 (1995).
Debouttiere et al., Design of gold nanoparticles for magnetic resonance imaging. Adv. Funct. Mater., 16:2330 (2006).
Demers et al., Combinatorial templates generated by dip-pen nanolithography for the formation of two-dimensional particle arrays, Angew. Chem. Int. Ed., 40: 3071-3 (2003).
DeMesmaeker et al., Backbone modifications in oligonucleotides and peptide nucleic acid systems, Curr. Opin. Structural Biol., 5:343-55 (1995).
Deutsch et al., Synthesis of congeners and prodrugs. 3. Water-soluble prodrugs of taxol with potent antitumor activity, J. Med. Chem., 32(4):788-92 (1989).
Devlin et al., Random peptide libraries: a source of specific protein binding molecules, Science, 249: 404-6 (1990).
Dhar et al., Polyvalent oligonucleotide gold nanoparticle conjugates as delivery vehicles for platinum(IV) warheads. J. Am. Chem. Soc., 131(41): 14652-3 (2009).
Dhar et al., Targeted single wall carbon nanotube mediated Pt(IV) prodrug delivery using folate as a homing device. J. Am. Chem. Soc., 130(34): 11467-76 (2008).
Dhomen et al., BRAF signaling and targeted therapies in melanoma, Hematol. Oncol. Clin. North Am., 23: 529-45, ix (2009).
Donachie, The cell cycle of *Escherichia coli*., Annu. Rev. Microbiol., 47:199-230 (1993).
Dreyfus et al., Simple quantitative model for the reversible associate of DNA coated colloids, Phys. Rev. Lett., 102: 048301 (2009).
Dubertret et al., Single-mismatch detection using gold-quenched fluorescent oligonucleotides, Nat. Biotechnol., 19: 365-70 (2001).
Duimstra et al., A gadolinium chelate for detection of beta-glucuronidase: a self-immolative approach, J. Am. Chem. Soc., 127(37):12847-55 (2005).
Dulkeith et al., Gold nanoparticles quench fluorescence by phase induced radiative rate suppression, Nano Lett., 5: 585-9 (2005).
Durand et al., Circular dichroism studies of an oligodeoxyribonucleotide containing a hairpin loop made of a hexaethylene glycol chain: conformation and stability. Nucl. Acids Res., 18(21): 6353-9 (1990).
Dykxhoorn et al., Killing the messenger: short RNAs that silence gene expression, Nat. Rev. Mol. Cell Biol., 4(6):457-67 (2003).
Eckstein (Ed.), Oligonucleotides and analogues, 1st Ed., Oxford University Press, New York (1991).
Elaissari et al., Effect of charge nature on the adsorption of single-stranded DNA fragments onto latex particles. J. Colloid Interface Sci., 202: 251-60 (1998).
Elghanian et al., Selective colorimetric detection of polynucleotides based on the distance-dependent optical properties of gold nanoparticles. Science, 277: 1078-81 (1997).
Eltekova et al., Adsorption of aromatic compounds from solutions on titanium dioxide and silica. Langmuir, 3(6): 951-7 (1987).
Endres et al., DNA-TiO2 nanoconjugates labeled with magnetic resonance contract agents. J. Am. Chem. Soc. 129(51): 15760-1 (2007).
Englisch et al., Chemically modified oligonucleotides as probes and inhibitors, Angew. Chem. Int. Ed. English, 30:613-29 (1991).
Enustun et al., Coagulation of colloidal gold, J Am Chem Soc, 85:3317-3328 (1963).
European Examination Report from corresponding European Application No. 08729548.1, dated Jan. 19, 2010.
Fahy et al., Design and synthesis of polyacrylamide-based oligonucleotide supports for use in nucleic acid diagnostics, Nucl. Acids Res., 21: 1819-26 (1993).

Fattal et al., Biodegradable polyalkylcyanoacrylate nanoparticles for the delivery of oligonucleotides. J. Control Rel., 53(1-3): 137-43 (1998).
Faulds et al., Evaluation of surface-enhanced resonance Raman scattering for quantitative DNA analysis. Anal. Chem., 76: 412-7 (2004).
Femino et al., Visualization of single RNA transcripts in situ. Science, 280: 585-90 (1998).
Ferentz et al., Disulfide-crosslinked oligonucleotides. J. Am. Chem. Soc., 113(10): 4000-2 (1991).
Final Office Action issued in connection with U.S. Appl. No. 11/917,680, dated Nov. 10, 2010.
Final Office Action issued in connection with U.S. Appl. No. 11/917,680, dated Nov. 10, 2011.
Final Office Action issued in connection with U.S. Appl. No. 12/130,643, dated Jun. 16, 2011.
Flandroy et al., (D, L)Polyactide microspheres as embolic agent. *Neuroradiology*, 32: 311-5 (1990).
Freier et al., The ups and downs of nucleic acid duplex stability: structure-stability studies on chemically-modified DNA:RNA duplexes, *Nucleic Acids Res.*, 25:4429-43 (1997).
Frens, Controlled nucleation for the regulation of the particle size in monodisperse gold suspensions, *Nature Physical Science*, 241 :20-2 (1973).
Frens, Particle size and sol stability in metal colloids, Kolloid-Zeitschrift und Zeitschrift fur Polymere, 250(7):736-41 (1972).
Frullano et al., Multimodal MRI contrast agents, J. Biol. Inorg. Chem., 12(7):939-40 (2007).
Fukuda et al., Bull. Chem. Soc. Jpn., 64:2013-5 (1991).
Fukuda et al., J. Org. Chem., 56(11):3729-31 (1991).
Furstner et al., Catalytic carbophilic activation: catalysis by platinum and gold pi acids, Angew Chem Int Ed Engl., 46(19):3410-49 (2007).
Gao et al., Secondary structure effects on DNA hybridization kinetics: a solution versus surface comparison. Nucl. Acids Res., 34: 3370-7 (2006).
Gavrieli et al., Identification of programmed cell death in situ via specific labeling of nuclear DNA fragmentation, J. Cell Biol., 119(3):493-501 (1992).
Gerdes et al., Experimental determination and system level analysis of essential genes in *Escherichia coli* MG1655, J. Bacteriol., 185:5673-84 (2003).
Gestwicki et al., Influencing receptor-ligand binding mechanisms with multivalent ligand architecture. J. Am. Chem. Soc., 124: 14922-33 (2002).
Ghosh et al., Gold nanoparticles in delivery applications, Adv. Drug Deliv. Rev. 60(11):1307-15 (2008).
Gibson et al., Paclitaxel-functionalized gold nanoparticles, J. Am. Chem. Soc., 129(37):11653-61 (2007).
Gidwani et al., Hybridization kinetics of double-stranded DNA probes for rapid molecular analysis. Analyst, 134: 1675-81 (2009).
Giljohann et al., Gene regulation with polyvalent siRNA-nanoparticle conjugates. J. Am. Chem. Soc., 131 :2072-3 (2009).
Giljohann et al., Gold nanoparticles for biology and medicine, Angew Chem. Int. Ed. Engl., 49(19):3280-94 (2010).
Giljohann et al., Oligonucleotide loading determines cellular uptake of DNA-modified gold nanoparticles. Nano Lett., 7(12): 3818-21 (2007).
Goel et al., Melanocytic nevus-like hyperplasia and melanoma in transgenic BRAFV600E mice. Oncogene, 28: 2289-98 (2009).
Goodrich et al., Non-coding-RNA regulators of RNA polymerase II transcription, Nat. Rev. Mol. Cell Biol., 7(8):612-6 (2006).
Grabar et al., Preparation and Characterization of Au Colloid Monolayers. Anal. Chem., 67(4): 735-43 (1995).
Guo et al., Cell-Selex: Novel perspectives of aptamer-based therapeutics, Int. J. Mol. Sci., 9: 668-78 (2008).
Guy et al., Transdermal drug delivery. Handb. Exp. Pharmacol., 197: 399-410 (2010).
Hale et al., Recruitment of ZipA to the septal ring of *Escherichia coli* is dependent on FtsZ and independent of FtsA., J. Bacteriol., 181:167-76 (1999).
Hames et al. (eds.), Gene Probes 1, New York: IRL Press (1995).

(56) References Cited

OTHER PUBLICATIONS

Hamilton et al., A species of small antisense RNA in post-transcriptional gene silencing in plants. Science, 286: 950-2 (1999).
Hammond et al., An RNA-directed nuclease mediates post-transcriptional gene silencing in Drosophilia cells. Nature, 404: 293-6 (2000).
Han et al., A gold nanoparticle based approach for screening triplex DNA binders, J. Am. Chem. Soc., 128(15):4954-5 (2006).
Hashmi et al., Gold catalysis, Angew Chem Int Ed Engl. 45(47):7896-936 (2006).
Hashmi et al., Gold-catalyzed organic reactions, Chem. Rev., 107(7):3180-211 (2007).
Hayashi, Ultrafine particles, Physics Today, pp. 44-60 (Dec. 1987).
Hayashi, Ultrafine particles, Vac. Sci. Technol., A5(4):1375-84 (1987).
Hayat, (Ed.) Colloidal Gold: Principles, Methods, and Applications, vol. 1, Table of Contents, pp. v-xvii; vol. 2, Table of Contents pp. v-xix; vol. 3, Table of Contents, pp. v-xiv, Academic Press, San Diego (1989-1991).
He et al., Colloidal Au-enhanced surface plasmon resonance for ultrasensitive detection of DNA hybridization. J. Am. Chem. Soc., 122(38): 9071-7 (2000).
Hegner et al., Modified DNA immobilized on bioreactive self-assembled monolayer on gold for dynamic force microscopy imaging in aqueous buffer solution, J. Vac. Sci. Technol. B, 14(2):1418-21 (1996).
Henglein et al., Absorption spectrum and some chemical reactions of colloidal platinum in aqueous solution. J. Phys. Chem., 99(38): 14129-36 (1995).
Henglein, Mechanism of reactions on colloidal microelectrodes and size quantization effects. Top. Curr. Chem., 143: 113-80 (1998).
Henglein, Small-particle research: physicochemical properties of extremely small colloidal metal and semiconductor particles. Chem. Rev., 89(8): 1861-73 (1989).
Hickman et al., Combining spontaneous molecular assembly with microfabrication to pattern surfaces: selective binding of isonitriles to platinum microwires and characterization by electrochemistry and surface spectroscopy. J. Am. Chem. Soc., 111(18): 7271-2 (1989).
Holen et al., Positional effects of short interfering RNAs targeting the human coagulation trigger tissue factor. Nucl. Acids Res., 30: 1757-66 (2002).
Hsu et al., Delivery of siRNA and other macromolecules into skin and cells using a peptide enhancer. Proc. Natl. Acad. Sci. USA, 108(38): 15816-21 (2011).
Hu et al., Advances in high-field magnetic resonance imaging, Annu. Rev. Biomed.Eng., 6:157-84 (2004).
Hu et al., Hollow chitosan/poly(acrylic acid) nanospheres as drug carriers, Biomacromolecules, 8(4):1069-76 (2007).
Hubbard, Electrochemistry of well-defined surfaces. Acc. Chem. Res., 13: 177-84 (1980).
Hurst et al., Multisegmented one-dimensional nanorods prepared by hard-template synthetic methods, Angew. Chem. Int. Ed. Engl., 45:2672-2692 (2006).
Hurst et al., Maximizing DNA loading on a range of gold nanoparticle sizes. Anal. Chem., 78: 8313 (2006).
Hussain et al., A novel anionic dendrimer for improved cellular delivery of antisense oligonucleotides. J. Controlled Rel., 99: 139-55 (2004).
Hwu et al., Targeted Paclitaxel by conjugation to iron oxide and gold nanoparticles, J. Am. Chem. Soc., 131(1):66-8 (2009).
Iler, The Chemistry of Silica, Chapter 6, pp. 622-729, New York: Wiley (1979).
International Preliminary Report on Patentability for corresponding international applicaton No. PCT/US2010/047594, dated Mar. 6, 2012.
International Preliminary Report on Patentability for International Application No. PCT/US2006/022325, dated Dec. 17, 2007.
International Preliminary Report on Patentability for International Application No. PCT/US2008/053603, dated Aug. 11, 2009.
International Preliminary Report on Patentability for International Application No. PCT/US2008/065366, dated Dec. 1, 2009.
International Preliminary Report on Patentability for International application No. PCT/US2009/065822, dated May 24, 2011.
International Preliminary Report on Patentability for International Application No. PCT/US2010/020558, dated Jul. 12, 2011.
International Preliminary Report on Patentability for International Application No. PCT/US2010/044453, dated Feb. 7, 2012.
International Preliminary Report on Patentability for International Application No. PCT/US2010/044844, dated Feb. 7, 2012.
International Preliminary Report on Patentability for Itnernational Application No. PCT/US2010/55018, dated May 1, 2012.
International Preliminary Report on Patentability, PCT/US2010/27363, dated Oct. 18, 2011.
International Preliminary Report on Patentability, PCT/US2010/47591, dated Mar. 6, 2012.
International Preliminary Report on Patentability, PCT/US2010/47594, dated Mar. 6, 2012.
International Search Report and Written Opinion for International Application No. PCT/US2006/022325, dated Oct. 20, 2006.
International Search Report and Written Opinion for International Application No. PCT/US2008/053603, dated Jul. 30, 2008.
International Search Report and Written Opinion for International Application No. PCT/US2008/065366, dated Aug. 28, 2008.
International Search Report and Written Opinion for International application No. PCT/US2008/065822, dated Mar. 5, 2010.
International Search Report and Written Opinion for International Application No. PCT/US2010/020558, dated Mar. 9, 2010.
International Search Report and Written Opinion for International Application No. PCT/US2010/044453, dated Apr. 29, 2011.
International Search Report and Written Opinion for International Application No. PCT/US2010/044844, dated Apr. 27, 2011.
International Search Report and Written Opinion for International Application No. PCT/US2010/27363, dated Apr. 15, 2010.
International Search Report and Written Opinion for International Application No. PCT/US2010/47591, dated Oct. 4, 2010.
International Search Report and Written Opinion for International Application No. PCT/US2010/47594, dated Oct. 8, 2010.
International Search Report and Written Opinion for International Application No. PCT/US2010/55018, dated Dec. 9, 2010.
International Search Report and Written Opinion from corresponding International Application No. PCT/US2010/044844, dated Apr. 24, 2011.
Introducing Antisense Oligonucleotides into Cells, Innovation & Precision in Nucleic Acid Synthesis, Integrated DNA Technologies (2005).
Jackson et al., *Escherichia coli* O157:H7 diarrhoea associated with well water and infected cattle on an Ontario farm, Epidemiol. Infect., 120:17-20 (1998).
Jackson et al., How do microRNAs regulate gene expression?, Sci STKE, 2007(367):re1 (2007).
Jason et al., Toxicology of antisense therapeutics. Toxicol. Appl. Pharmacol., 201(1): 66-83 (2004).
Jen et al., A nonviral transfection approach in vitro: the design of a gold nanoparticle vector joint with microelectromechanical systems. Langmuir, 20(4): 1369-74 (2004).
Jeong et al., Novel intracellular delivery system of antisense oligonucleotide by self-assembled hybrid micelles composed of DNA/PEG conjugate and cationic fusogenic peptide. Bioconjugate Chem., 14: 473-9 (2003).
Jin et al., Radiosensitization of paclitaxel, etanidazole and paclitaxel+etanidazole nanoparticles on hypoxic human tumor cells in vitro, Biomaterials, 28(25):3724-30 (2007).
Jin et al., What controls the melting properties of DNA-linked gold nanoparticle assemblies? J. Am. Chem. Soc., 125: 1643 (2003).
Jäschke et al., Automated incorporation of polyethylene glycol in synthetic oligonucleotides. Tetrahedron Lett., 34: 301-4 (1993).
Kalman et al., Potentiometric and relaxometric properties of a gadolinium-based MRI contrast agent for sensing tissue pH, Inorg. Chem., 46(13):5260-70 (2007).
Kan et al., Distribution and effect of iodized poppyseed oil in the liver after hepatic artery embolization: experimental study in several animal species, Radiology, 186(3):861-6 (1993).

(56) References Cited

OTHER PUBLICATIONS

Kan et al., Role of Kupffer cells in iodized oil embolization, Invest. Radiol., 29(11):990-3 (1994).
Kasuya et al., Chapter 8—Bio-nanocapsule-liposome conjugates for in vivo pinpoint drug and gene delivery, Methods Enzymol., 464:147-66 (2009).
Katz et al., Integrated nanoparticle-biomolecule hybrid systems: synthesis, properties, and applications, Angew. Chem. Int. Ed., 43: 6042-108 (2004).
Katz, The reversible reaction of sodium thymonucleate and mercuric chloride, J. Am. Chem. Soc., 74: 2238-45 (1952).
Kim et al., Biodegradable quantum dot nanocomposites enable live cell labeling and imaging of cytoplasmic targets, Nano Lett., 8(11):3887-92 (2008).
Kim et al., Direct synthesis of polymer nanocapsules with a noncovalently tailorable surface, Angew. Chem. Int. Ed. Engl., 46(19):3471-4 (2007).
Kim et al., Direct synthesis of polymer nanocapsules: self-assembly of polymer hollow spheres through irreversible covalent bond formation, J. Am. Chem. Soc., 132(28):9908-19 (2010).
Kim et al., Facile, template-free synthesis of stimuli-responsive polymer nanocapsules for targeted drug delivery, Angew. Chem. Int. Ed. Engl., 49(26):4405-8 (2010).
Kloosterman et al., In situ detection of miRNAs in animal embryos using LNA-modified oligonucleotide probes, Nat. Methods, 3: 27-9 (2006).
Kolarova et al., Preparation of magnetic oligo (dT) particles, Biotechniques, 20: 196-8 (1996).
Kondo et al., Nanotube formation through the continuous one-dimensional fusion of hollow nanocapsules composed of layer-by-layer poly(lactic acid) stereocomplex films, J. Am. Chem. Soc., 132(24):8236-7 (2010).
Kopylov et al., Combinatorial chemistry of nucleic acids: SELEX, Mol. Biol., 34: 940-54 (2000).
Kosturko et al., The crystal and molecular structure of a 2:1 complex of 1-methylthymine-mercury(II), Biochem., 13:3949-52 (1974).
Kroschwitz (Ed.), The Concise Encyclopedia of Polymer Science and Engineering, pp. 858-859, John Wiley & Sons (1990).
Krutzfeldt et al., Silencing of microRNAs in vivo with 'antagomirs', Nature, 438(7068):685-9 (2005).
Kukowska-Latallo et al., Efficient transfer of genetic material into mammalian cells using Starburst polyamidoamine dendrimers, Proc. Natl. Acad. Sci. USA, 93: 4897-902 (1996).
Landfester et al., From polymeric particles to multifunctional nanocapsules for biomedical applications using the miniemulsion process, J. Polymer Sci. Part A, 48(3):493-515 (2010).
Lannutti et al., Human angiostatin inhibits murine hemangioendothelioma tumor growth in vivo, Cancer Res., 57: 5277-80 (1997).
Leachman et al., Therapeutic siRNAs for dominant genetic skin diseases including pachyonychia congenita. J. Dermatol. Sci., 51(3): 151-7 (2008).
Lebedeva et al., Antisense oligonucleotides: Promise and reality. Annu. Rev. Pharmacol. Toxicol., 41: 403-19 (2001).
Lee et al., Adsorption of ordered zirconium phosphonate multilayer films on silicon and gold surfaces. J. Phys. Chem., 92: 2597-601 (1988).
Lee et al., Chip-based scanometric detection of mercuric ion using DNA-functionalized gold nanoparticles, Anal. Chem., 80(17):6805-8 (2008).
Lee et al., Colorimetric detection of mercuric ion (Hg2+) in aqueous media using DNA-functionalized gold nanoparticles, Angew. Chem. Int. Ed. Engl., 46(22):4093-6 (2007).
Lemaigre et al., Transcriptional control of genes that regulate glycolysis and gluconeogenesis in adult liver, Biochem. J., 303:1-14 (1994).
Leslie et al., A new tool for oligonucleotides import into cells. Clin. Chem., 55: 609-10 (2009).

Leunissen et al., Switchable self-protected attractions in DNA-functionalized colloids. Nat. Mater., 8: 590-95 (2009).
Lewis, Controlled release of bioactive agents from lactide/glycolide polymer, pp. 1-41, in: Chasin et al. (eds.), Biodegradable Polymers as Drug Delivery Systems, Marcel Dekker (1990).
Li et al., A calcium-sensitive magnetic resonance imaging contrast agent. J. Am. Chem. Soc., 121:1413 (1999).
Li et al., Dual-reactive surfactant used for synthesis of functional nanocapsules in miniemulsion, J. Am. Chem. Soc., 132(23):7823-5 (2010).
Li et al., Gold-catalyzed organic transformations, Chem. Rev., 108(8):3239-65 (2008).
Li et al., Reversible and chemically programmable micelle assembly with DNA block-copolymer amiphiphiles, Nano Lett., 4(6):1055-8 (2004).
Lin et al., Effector/memory but not naive regulatory T cells are responsible for the loss of concomitant tumor immunity. J. Immunol., 182: 6095-104 (2009).
Lin et al., Modeling genomic diversity and tumor dependency in malignant melanoma. Cancer Res., 68: 664-73 (2003).
Link et al., J. Phys. Chem. B, 103(21):4212-7 (1999).
Lipshutz et al., High density synthetic oligonucleotide arrays. Nanotechnology, 14: R15-27 (2003).
Liu et al., Accelerated color change of gold nanoparticles assembled by DNAzymes for simple and fast colorimetric Pb2+ detection. J. Am. Chem. Soc., 126: 12298-305 (2004).
Liu et al., ARDB—Antibiotic Resistance Genes Database, *Nucl. Acids Res.*, 37:D443-7 (2009).
Liu et al., Argonaute2 is the catalytic engine of mammalian RNAi. Science, 305(5689): 1437-41 (2004).
Liu et al., Cross-linked polynorbornene-coated gold nanoparticles: dependence of particle stability on cross-linking position and cross-linker structure, Langmuir, 24(19):11169-74 (2008).
Liu et al., De-N-acetyl GM3 promotes melanoma cell migration and invasion through urokinase plasminogen activator receptor signaling-dependent MMP-2 activation. Cancer Res., 69: 8662-9 (2009).
Liu et al., DNA-based micelles: synthesis, micellar properties and size-dependent cell permeability, Chemistry, 16(12):3791-7 (2010).
Liu et al., New poly(d-glucaramidoamine)s induce DNA nanoparticle formation and efficient gene delivery into mammalian cells. J. Am. Chem. Soc., 126: 7422-3 (2004).
Liu et al., Rational design of "turn-on" allosteric DNAzyme catalytic beacons for aqueous mercury ions with ultrahigh sensitivity and selectivity, Angew. Chem. Int. Ed. Engl., 46(60):7587-90 (2007).
Liu et al., Synthesis, stability, and cellular internalization of gold nanoparticles containing mixed peptide-poly(ethylene glycol) monolayers. Anal. Chem., 79: 2221-9 (2007).
Llovet et al., Arterial embolisation or chemoembolisation versus symptomatic treatment in patients with unresectable hepatocellular carcinoma: a randomised controlled trial, Lancet, 359(9319):1734-9 (2002).
Loeken, Effects of mutation of the CREB binding site of the somatostatin promoter on cyclic AMP responsiveness in CV-1 cells, Gene Expr., 3:253-64 (1993).
Love et al., Self-assembled monolayers of thiolates on metals as a form of nanotechnology. Chem. Rev., 105: 1103-69 (2005).
Lutkenhaus et al., Bacterial cell division and the Z ring, Annu. Rev. Biochem., 66:93-116 (1997).
Lytton-Jean et al., A thermodynamic investigation into the binding properties of DNA functionalized gold nanoparticle probes and molecular fluorophore probes. J. Am. Chem Soc., 127: 12754-5 (2005).
Ma et al., Design and synthesis of RNA miniduplexes via a synthetic linker approach. 2. Generation of covalently closed, double-stranded cyclic HIV-1 TAR RNA analogs with high Tat-binding affinity. Nucl. Acids Res., 21: 2585-9 (1993).
Ma et al., Design and synthesis of RNA miniduplexes via a synthetic linker approach. Biochemistry, 32(7): 1751-8 (1993).
Major et al., Bioresponsive, cell-penetrating, and multimeric MR contrast agents, Acc. Chem. Res., 42(7):893-903 (2009).
Major et al., The synthesis and in vitro testing of a zinc-activated MRI contrast agent, Proc. Natl. Acad. Sci. USA, 104(35):13881-6 (2007).

(56) References Cited

OTHER PUBLICATIONS

Maoz et al., Penetration-controlled reactions in organized monolayer assemblies. 1. Aqueous permanganate interaction with monolayer and multilayer films of long-chain surfactants. Langmuir, 3: 1034-44 (1987).
Maoz et al., Penetration-controlled reactions in organized monolayer assemblies. 2. Aqueous permanganate interaction with self-assembling monolayers of long-chain surfactants. Langmuir, 3: 1045-1051 (1987).
Marinakos et al., Gold nanoparticles as templates for the synthesis of hollow nanometer-sized conductive polymer capsules, Ad. Mater, 11:34-37 (1999).
Marinakos et al., Template synthesis of one-dimensional Au, Au-poly(pyrrole), and poly(pyrrole) nanoparticle arrays, Chem Mater, 10:1214-19 (1998).
Martin et al., 38. Ein neuer zugang zu 2'-O-alkylribonucleosiden and eigenschaften deren oligonucleotide, Helv. Chim. Acta, 78:486-504 (1995) [English abstract only.].
Martin, A New Access to 2-O-Alkylated Ribonucleosides and Properties of 2-O-Alkylated Oligoribonucleotides. Helv. Chim. Acta 1995; 78: 486-504.
Martinez et al., Locked nucleic acid based beacons for surface interaction studies and biosensor development. Anal. Chem., 81: 3448-54 (2009).
Maruyama, et al., Nanoparticle DNA carrier with poly(L-lysine) grafted polysaccharide copolymer and poly(D,L-lactic acid). Bioconjugate Chem., 8: 735-742 (1997).
Massart, Preparation of aqueous magnetic liquids in alkaline and acidic media. IEEE Transactions on Magnetics. 17(2): 1247-8 (1981).
Matsuura et al., Construction and characterization of protein libraries composed of secondary structure modules. Protein Sci., 11: 2631-43 (2002).
Matteucci et al., Synthesis of deoxyoligonucleotides on a polymer support. J. Am. Chem. Soc., 103: 3185-91 (1981).
Mattson et al., A practical approach to crosslinking. Molec. Biol. Rep., 17: 167-83 (1993).
Maxwell et al., Self-assembled nanoparticle probes for recognition and detection of biomolecules. J. Am. Chem. Soc., 124: 9606-12 (2002).
Maye et al., A simple method for kinetic control of DNA-induced nanoparticle assembly. J. Am. Chem. Soc., 128: 14020-1 (2006).
Mayer (ed.), Nucleic Acid and Peptide Aptamers: Methods and Protocols (Humana Press, 2009).
McCurdy et al., Deoxyligonucleotides with inverted polarity: Synthesis and use in triple-helix formation. Nucleosides & Nucleotides, 10: 287-90 (1991).
McGehee et al., Differentiation-specific element: a cis-acting developmental switch required for the sustained transcriptional expression of the angiotensinogen gene during hormonal-induced differentiation of 3T3-L1 fibroblasts to adipocytes, Mol. Endocrinol., 7:551-60 (1993).
McKenzie et al., Sequence-specific DNA detection using high-affinity LNA-functionalized gold nanoparticles. Small, 3(11): 1866-8 (2007).
McManus et al., Gene silencing in mammals by small interfering RNAs. Nat. Rev. Genet., 3(10): 737-47 (2002).
Mendell, MicroRNAs: critical regulators of development, cellular physiology and malignancy, Cell Cycle, 4(9):1179-84 (2005).
Merbach et al. (eds.), The Chemistry of Contrast Agents in Medical Magnetic Resonance Imaging, 1st ed., New York: Wiley (2001).
Miller et al., Antisense oligonucleotides: Strategies for delivery. PSTT, 1(9): 377-86 (1998).
Milne et al., An approach to gene-specific transcription inhibition using oligonucleotides complementary to the template strand of the open complex. Proc. Natl. Acad. Sci. USA, 97(7): 3136-41 (2000).
Mirkin et al., A DNA-based method for rationally assembling nanoparticles into macroscopic materials. Nature, 382(6592): 607-9 (1996).

Mitragotri et al., Ultrasound-mediated transdermal protein delivery. Science, 269: 850-3 (1995).
Mittal, Improving the efficiency of RNA interference in mammals, Nat. Rev. Genet., 5(5):355-65 (2004).
Modo et al. (eds.), Molecular and Cellular MR Imaging, Florida: CRC Press (2007).
Modo et al., Mapping transplanted stem cell migration after a stroke: a serial, in vivo magnetic resonance imaging study, Neuroimage, 21(1):311-7 (2004).
Moriggi et al., Gold nanoparticles functionalized with gadolinium chelates as high-relaxivity MRI contrast agents, J. Am. Chem. Soc., 131(31):10828-9 (2009).
Moughton et al., Hollow nanostructures from self-assembled supramolecular metallo-triblock copolymers, Soft Matter, 5(12):2361-70 (2009).
MRS Bulletin, Fine Particles Pt. II, pp. 16-47 (Jan. 1990).
Mucic et al., Synthesis and characterization of DNA with ferrocenyl groups attached to their 5-termini: electrochemical characterization of a redox-active nucleotide monolayer. Chem. Commun., 4: 555-7 (1996).
Myers et al., A cyclopentane conformational restraint for a peptide nucleic acid: design, asymmetric synthesis, and improved binding affinity to DNA and RNA. Org Lett., 5(15): 2695-8 (2003).
Nam et al., Nanoparticle-based bio-bar codes for the ultrasensitive detection of proteins. Science, 301: 1884-6 (2003).
Nielsen et al., Sequence-selective recognition of DNA by strand displacement with a thymine-substituted polyamide, Science, 254:1497-500 (1991).
Nitin et al., Peptide-linked molecular beacons for efficient delivery and rapid mRNA detection in living cells. Nucl. Acids Res., 32: e58 (2004).
Nitin, et al. Oligonucleotide-Coated Metallic Nanoparticles as a Flexible Platform for Molecular Imaging Agents, Bioconjugate Chem. 18:2090-2096 (2007).
Non-Final Office Action issued in connection with U.S. Appl. No. 11/917,680, dated Jun. 8, 2011.
Non-Final Office Action issued in connection with U.S. Appl. No. 12/130,643, dated Jan. 13, 2011.
Non-Final Office Action issued in connection with U.S. Appl. No. 12/526,560, dated Mar. 15, 2012.
Non-Final Office Action issued in connection with U.S. Appl. No. 12/625,537, dated May 23, 2012.
Non-Final Office Action issued in connection with U.S. Appl. No. 12/684,836, dated Jan. 6, 2012.
Non-Final Office Action issued in connection with U.S. Appl. No. 12/684,836, dated May 17, 2012.
Non-Final Office Action issued in connection with U.S. Appl. No. 12/724,395, dated Feb. 17, 2012.
Notice of Allowance issued in connection with U.S. Appl. No. 11/917,680, dated Apr. 26, 2012.
Nuzzo et al., Spontaneously organized molecular assemblies. 3. Preparation and properties of solution adsorbed monolayers of organic disulfides on gold surfaces. J. Am. Chem. Soc., 109(8): 2358-68 (1987).
Nykypanchuk et al., DNA-guided crystallization of colloidal nanoparticles. Nature, 451: 549-52 (2008).
O'Meara et al., Capture of single-stranded DNA assisted by oligonucleotide modules. Anal. Biochem., 255: 195-203 (1998).
O'reilly et al., Identification of an activating transcription factor (ATF) binding site in the human transforming growth factor-beta 2 promoter, J. Biol. Chem., 267:19938-43 (1992).
Ohishi et al., Hepatocellular carcinoma detected by iodized oil. Use of anticancer agents, Radiology, 154(1):25-9 (1985).
Ohuchi et al., In vitro method for the generation of protein libraries using PCR amplification of a single DNA molecule and coupled transcription/translation, Nucl. Acids Res., 26: 4339-46 (1998).
Okayasu et al., Selective and persistent deposition and gradual drainage of iodized oil, Lipiodol in the hepatocellular carcinoma after injection into the feeding hepatic artery, Am. J. Clin. Pathol., 90(5):536-44 (1988).
Olshaysky et al., Organometallic synthesis of gallium-arsenide crystallites, exhibiting quantum confinement. J. Am. Chem. Soc., 112(25): 9438-9 (1990).

(56) References Cited

OTHER PUBLICATIONS

Ono et al., DNA triplex formation of oligonucleotide analogues consisting of linker groups and octamer segments that have opposite sugar-phosphate backbone polarities. Biochemistry, 30(41): 9914-2 (1991).
Opalinska et al., Nucleic-acid therapeutics: basic principles and recent applications. Nat. Rev. Drug Discov., 1: 503-14 (2002).
Ow Sullivan et al., Development of a novel gene delivery scaffold utilizing colloidal gold-polyethylenimine conjugates for DNA condensation. Gene Ther., 10(22): 1882-90 (2003).
Ozpolat et al., Nanomedicine based approaches for the delivery of siRNA in cancer, J. Intern. Med., 267(1):44-53 (2010).
Paciotti et al., Colloidal gold: a novel nanoparticle vector for tumor directed drug delivery, Drug Deliv., 11(3):169-83 (2004).
Parak et al., Biological applications of colloidal nanocrystals, Nanotechnol., 14: R15-27 (2003).
Park et al., Array-based electrical detection of DNA with nanoparticle probes. Science, 295: 1503-6 (2002).
Park et al., DNA-programmable nanoparticle cystrallization. Nature, 451: 553-6 (2008).
Park et al., Gold nanoparticles functionalised by Gd-complex of DTPA-bis(amide) conjugate of glutathione as an MRI contrast agent, Bioorg. Med. Chem. Lett, 18(23):6135-7 (2008).
Parrish et al., Functional anatomy of a dsRNA trigger: Differential requirement for the two trigger strands in RNA interference. Mol. Cell, 6: 1077-87 (2000).
Patel et al., Peptide antisense nanoparticles. Proc. Natl. Acad. Sci. USA, 105: 17222-6 (2008).
Patel et al., Scavenger receptors mediate cellular uptake of polyvalent oligonucleotide-functionalized gold nanoparticles, Bioconjug. Chem., 21(12):2250-6 (2010).
Patil et al., DNA-based therapeutics and DNA delivery systems: a comprehensive review. AAPS J., 7(1): E61-77 (2005).
Paunecku et al., Godolinium-conjugated Ti02-DNA oligonucleotide nanocanjugates show prolonged intracellular retention period and T1-weighted contract enhancement in magnetic resonance images. Nanomedicine, 4(3): 201-7 (2008).
Peng et al., Real-time detection of gene expression in cancer cells using molecular beacon imaging: New strategies for cancer research. Cancer Res., 65: 1909-17 (2005).
Penn et al., Nanoparticles for bioanalysis. Curr. Opin. Chem. Biol., 7: 609-15 (2003).
Peracchi, Prospects for antiviral ribozymes and deoxyribozymes. Rev. Med. Virol., 14: 47-64 (2004).
Perlette et al., Real-time monitoring of intracellular mRNA hybridization inside single living cells. Anal. Chem., 73: 5544-50 (2001).
Pon, Solid-phase supports for oligonucleotide synthesis, Methods in Molecular Biology, pp. 465-496 (1993).
Prausnitz et al., Transdermal drug delivery, Nat. Biotechnol., 26: 1261-8 (2008).
Prausnitz eta l., Microneedles for transdermal drug delivery. Adv. Drug Delivery Rev., 56: 581-7 (2004).
Prigodich et al., Nano-flares for mRNA regulation and detection. ACS Nano, 3: 2147-52 (2009).
Prime et al., Self-assembled organic monolayers; Model systems for studing adsorption of proteins at surfaces. Science, 252: 1164-7 (1991).
Raj et al., Stochastic mRNA synthesis in mammalian cells. PLoS Biol., 4(10): e309 (2006).
Rethore et al., Preparation of chitosan/polyglutamic acid spheres based on the use of polystyrene template as nonviral gene carrier. Tissue Engineering, 15(4): 605-13 (2009).
Rethore et al., Use of templates to fabricate nanoscale spherical structures for defined architectural control, Small, 6(4):488-98 (2010).
Riccelli et al., Hybridization of single-stranded DNA targets to immobilized complementary DNA probes: comparison of hairpin versus linear capture probes. Nucl. Acids Res., 29: 996-1004 (2001).

Richardson et al., Tethered oligonucleotide probes. A strategy for the recognition of structured RNA. J. Am. Chem. Soc., 113(13): 5109-11 (1991).
Rihova et al., Receptor-mediated targeted drug or toxin delivery. Adv. Drug Deliv. Rev., 29(3): 273-89 (1998).
Rizzo et al., Chimeric RNA-DNA molecular beacon assay for ribonuclease H activity. Mol. Cell Probes, 16: 277-83 (2002).
Rosi et al., Nanostructures in biodiagnostics. Chem Rev., 105(4): 1547-62 (2005).
Rosi et al., Oligonucleotide-modified gold nanoparticles for intracellular gene regulation. Science, 2312(5776): 1027-30 (2006).
Sadauskas et al., Protracted elimination of gold nanoparticles from mouse liver, Nanomedicine, 5(2):162-9 (2009).
Sambrook et al., Molecular Cloning: A Laboratory Manual, 2nd Edition, Table of Contents, pp. v-xxxii (1989).
Sandhu et al., Gold nanoparticle-mediated transfection of mammalian cells. Bioconjugate Chem., 13: 3-6 (2002).
Sanghvi et al., Heterocyclic base modifications in nucleic acids and their applications in antisense oligonucleotides, Chapter 15 in: Crooke et al. (eds.), Antisense Research and Applications, Boca Raton: CRC Press (1993).
Santangelo et al., Dual FRET molecular beacons for mRNA detection in living cells. Nucl. Acids Res., 32:e57 (2004).
Santangelo et al., Nanostructured probes for RNA detection in living cells. Ann. Biomed. Eng., 34:39-50 (2006).
Schifferlers et al., Cancer siRNA therapy by tumor selective delivery with ligand-targeted sterically stabilized nanoparticle. Nucl. Acid Res., 32(19): e149 (2004).
Schmid, G. (ed.) Clusters and Colloids (VCH, Weinheim, 1994).
Seela et al., Oligodeoxyribonucleotides containing 1,3-propanediol as nucleoside substitute. Nucl. Acids Res., 15(7): 3113-29 (1987).
Seelig et al., Catalyzed relaxation of a metastable DNA fuel. J. Am. Chem. Soc., 128: 12211-20 (2006).
Seferos et al., Locked nucleic acid-nanoparticle conjugates. Chembiochem., 8: 1230-2 (2007).
Seferos et al., Nano-flares: probes for transfection and mRNA detection in living cells. J. Am. Chem. Soc., 129: 15477-9 (2007).
Seferos et al., Polyvalent DNA nanoparticle conjugates stabilize nucleic acids. Nano Lett., 9: 308-11 (2009).
Sharma et al., Characterization of MRI contrast agent-loaded polymeric nanocapsules as versatile vehicle for targeted imaging, Contrast Media Mol. Imaging, 5(2):59-69 (2010).
Sharma et al., Mutant V599EB-Raf regulates growth and vascular development of malignant melanoma tumors. Cancer Res., 65: 2412-21 (2005).
Sharma et al., Targeting Akt3 signaling in malignant melanoma using isoselenocyanates. Clin. Cancer Res., 15: 1674-85 (2009).
Sharma et al., Targeting mitogen-activated protein kinase/extracellular signal-regulated kinase kinase in the mutant (V600E) B-Raf signaling cascade effectively inhibits melanoma lung metastases. Cancer Res., 66: 8200-9 (2006).
Sharp et al., RNA interference—2001. Genes Dev., 15: 485-90 (2001).
Shu et al., Gradient cross-linked biodegradable polyelectrolyte nanocapsules for intracellular protein drug delivery, Biomaterials, 31(23):6039-49 (2010).
Simmel et al., DNA nanodevices. Small, 1: 284-99 (2005).
Skwarczynski et al., Paclitaxel prodrugs: toward smarter delivery of anticancer agents, J. Med. Chem., 49(25):7253-69 (2006).
Smith et al., Bioconjugated quantum dots for in vivo molecular and cellular imaging, Adv. Drug Deliv. Rev., 60(11):1226-40 (2008).
Sokol et al., Real time detection of DNA.RNA hybridization in living cells. Proc. Natl. Acad. Sci. USA, 95: 11538-43 (1998).
Song et al., Synthesis of multimeric MR contrast agents for cellular imaging, J. Am. Chem. Soc., 130(21):6662-3 (2008).
Soriaga et al., Determination of the orientation of aromatic molecules adsorbed on platinum electrodes. The effect of solute concentration. J. Am. Chem. Soc., 104: 3937-45 (1982).
Srivastava et al., Use of riboprobes for northern blotting analysis. Biotechniques, 11(5): Abstract (1991).
Stahl et al., Deregulated Akt3 activity promotes development of malignant melanoma, Cancer Res., 64: 7002-10 (2004).

(56) References Cited

OTHER PUBLICATIONS

Stephenson et al., Inhibition of Rous sarcoma viral RNA translation by a specific oligodeoxyribonucleotide. Proc. Natl. Acad. Sci. USA, 75(1): 285-8 (1978).
Stoermer et al., Distance-dependent emission from dye-labeled oligonucleotides on striped Au/Ag nanowires: effect of secondary structure and hybridization efficiency. J. Am. Chem. Soc., 128: 13243-54 (2006).
Stoeva et al., Multiplexed detection of protein cancer markers with biobarcoded nanoparticle probes. J. Am. Chem. Soc., 128: 8378-9 (2006).
Storhoff et al., One-pot colorimetric differentiation of polynucleotides with single base imperfections using gold nanoparticle probes, J. Am. Chem. Soc., 120:1959-64 (1998).
Storhoff et al., What controls the optical properties of DNA-linked gold nanoparticle assemblies? J. Am. Chem. Soc., 122: 4640-50 (2000).
Storz et al., An abundance of RNA regulators, Annu. Rev. Biochem., 74:199-217 (2005).
Sugihara et al., One-pot synthesis of biomimetic shell cross-linked micelles and nanocages by ATRP in alcohol/water mixtures, Angew. Chem. Int. Ed. Engl., 48(20):3500-3 (2010).
Sun et al., Ganglioside loss promotes survival primarily by activating integrin-linked kinase/Akt without phosphoinositide 3-OH kinase signaling. J. Invest. Dermatol., 119: 107-17 (2002).
Sundaram et al., Particle-mediated delivery of recombinant expression vectors to rabbit skin induces high-titered polyclonal antisera (and circumvents purification of a protein immunogen). Nucl. Acids Res., 24(7): 1375-7 (1996).
Tan et al., Facile synthesis of hybrid silica nanocapsules by interfacial templating condensation and their application in fluorescence imaging, Chem. Commun. (Camb.), Nov. 7(41):6240-2 (2009).
Taton et al., Scanometric DNA array detection with nanoparticle probes, Science, 289(5485):1757-60 (2000).
Thomas et al., Conjugation to gold nanoparticles enhances polyethylenimine's transfer of plasmid DNA into mammalian cells. Proc. Natl. Acad. Sci. USA, 100(16): 9138-43 (2003).
Thomas et al., The interaction of HgCl2 with sodium thymonucleate, J. Am. Chem. Soc., 76:6032-4 (1954).
Thompkins et al., The study of the gas-solid interaction of acetic acid with a cuprous oxide surface using reflection-absorption spectroscopy. J. Colloid Interface Sci., 49: 410-21 (1974).
Thurn et al., Labeling TiO2 nanoparticles with dyes for optical fluorescence microscopy and determination of TiO2-DNA nanoconjugate stability. Small, 5(11): 1318-25 (2009).
Timmons et al., Investigation of fatty acid monolayers on metals by contact potential measurements. J. Phys. Chem., 69(3): 984-90 (1965).
Tkachenko et al., Cellular trajectories of peptide-modified gold particle complexes: comparison of nuclear localization signals and peptide transduction domains. Bioconjugate Chem., 15(3): 482-90 (2004).
Tkachenko et al., Multifunctional gold nanoparticle-peptide complexes for nuclear targeting. J. Am. Chem. Soc., 125: 4700-1 (2003).
Tondelli, et al., Highly efficient cellular uptake of c-myb antisense oligonucleotides through specifically designed polymeric nanospheres. Nucl. Acids Res., 26: 5425-31 (1998).
Treisman, The SRE: a growth factor responsive transcriptional regulator, Semin. Cancer Biol., 1:47-58 (1990).
Tsao et al., Genetic interaction between NRAS and BRAF mutations and pten/mmac1 inactivation in melanoma. J. Invest. Dermatol., 122: 337-41 (2004).
Tuerk et al., Systematic evolution of ligands by exponential enrichment: RNA ligands to bacteriophage T4 DNA polymerase. Science, 249: 505-10 (1990).
Turberfield et al., DNA fuel for free-running nanomachines. Phys. Rev. Lett., 90: 118102 (2003).
Turner et al., Nanoscale Cage-like Structures Derived from Polyisoprene-Containing Shell Cross-linked Nanoparticle Templates, Nano Lett., 4(4):683-8 (2004).

Tyagi et al., Molecular beacons: Probes that fluoresce upon hybridization. Nat. Biotechnol., 14: 303-8 (1996).
Uchida et al., Gallium arsenide nanocrystals prepared in quinoline. J. Phys. Chem. 95(14): 5382-4 (1991).
Vasiliskov et al., Parallel multiplex thermodynamic analysis of coaxial base stacking in DNA duplexes by oligodeoxyribonucleotide microchips. Nucl. Acids Res., 29: 2303-13 (2001).
Virmani et al., Comparison of two different methods for inoculating VX2 tumors in rabbit livers and hind limbs, J. Vasc. Interv. Radiol., 19(6):931-6 (2008).
Wagner et al., Gene inhibition using antisense oligodeoxynucleotides. Nature, 372: 333-5 (1994).
Wang et al., Ganglioside GM3 inhibits matrix metalloproteinase-9 activation and disrupts its association with integrin, J. Biol. Chem., 278: 25591-9 (2003).
Wang et al., Ganglioside GM3 promotes carcinoma cell proliferation via urokinase plasminogen activator-induced extracellular signal-regulated kinase-independent p70S6 kinase signaling, J. Invest. Dermatol., 126: 2687-96 (2006).
Wang et al., Inhibition of integrin-linked kinase/protein kinase B/Akt signaling: mechanism for ganglioside-induced apoptosis. J. Biol. Chem., 276: 44504-11 (2001).
Wang et al., Locked nucleic acid molecular beacons. J. Am. Chem. Soc., 127: 15664-5 (2005).
Wang et al., Molecular engineering of DNA: molecular beacons. Angew. Chem., Int. Ed., 48: 856-70 (2009).
Wang et al., Nanometer-sized semiconductor clusters: materials synthesis, quantum size effects, and photophysical properties. J. Phys. Chem., 95(2): 525-32 (1991).
Wang et al., Nanoparticles for multiplex diagnostics and imaging. Nanomedicine (Lond.), 1: 413-26 (2006).
Wang et al., Speeding up a single-molecule DNA device with a simple catalyst. Phys. Rev. E Stat. Nonlin. Soft Matter. Phys., 72: 051918 (2005).
Wang et al., Superparamagnetic sub-5 nm Fe@ nanoparticles: isolation, structure, magnetic properties, and directed assembly, Nano Lett., 8(11):3761-5 (2008).
Warnmark et al., Activation functions 1 and 2 of nuclear receptors: molecular strategies for transcriptional activation, Mol. Endocrinol., 17(10):1901-9 (2003).
Wasserman et al., Structure and reactivity of alkylsiloxane monolayers formed by reaction of alkyltrichlorosilanes on silicon substrates. Langmuir, 5(4) 1074-87 (1989).
Watson et al. (eds.), Molecular Biology of the Gene, 4th ed., The Benjamin/Cummings Publishing Company Inc. (1987).
Wei et al., A study of the relationships between oligonucleotide properties and hybridization signal intensities from NimbleGen microarray datasets. Nucl. Acids Res., 36: 2926-38 (2008).
Wellbrock et al., V599EB-RAF is an oncogene in melanocytes. Cancer Res., 64: 2338-42 (2004).
Weller, Colloidal Semiconductor Q-particles: Chemistry in the transition region between solid state and molecules. Angew. Chem. Int. Ed. Engl., 32(1): 41-53 (1993).
Whitesides, Proceedings of the Robert A. Welch Foundation 39th Conference on Chemical Research Nanophase Chemistry, Houston, Tex., pp. 109-121 (1995).
Wikipedia entry on Aspirin, Last modified on Oct. 6, 2010 (online). Retrieved on Oct. 7, 2010). Retrieved from the Internet: <http://en.wikipedia.org/wiki/Aspirin>.
Wikipedia entry on Phenylbutazone. Last modified on Sep. 20, 2010. Online. (Retrieved on Oct. 7, 2010). Retrieved from the Internet: < http://en.wikipedia.org/wiki/Phenylbutazone>.
Wikipedia entry on Warfarin. Last modified on Oct. 5, 2010. (Online) (Retrieved on Oct. 8, 2010). Retrieved from the Internet: < http://en.wikipedia.org/wiki/Warfarin>.
Winter et al., Molecular imaging by MRI, Curr. Cardiol. Rep. 8(1):65-9 (2006).
Wolf et al., Rapid hybridization kinetics of DNA attached to submicron latex particles. Nucl. Acids Res., 15: 2911-26 (1987).
Xia, Nanomaterials at work in biomedical research, Nat. Mater., 7(10):758-60 (2008).

(56) References Cited

OTHER PUBLICATIONS

Xu et al., A gold-nanoparticle-based real-time colorimetric screening method for endonuclease activity and inhibition, Angew. Chem. Int. Ed. Engl., 46(19):3468-70 (2007).

Xu et al., Homogeneous detection of nucleic acids based upon the light scattering properties of silver-coated nanoparticle probes, Anal. Chem., 79(17):6650-4 (2007).

Xu et al., Thermodynamics of DNA hybridization on gold nanoparticles. J. Am. Chem. Soc., 127(38): 13227-31 (2005).

Yamane et al., On the complexing of desoxyribonucleic acid (DNA) by mercuric ion, J. Am. Chem. Soc., 83:2599-607 (1961).

Yan et al., Aptamers and aptamer targeted delivery. RNA Biol., 6: 316-20 (2009).

Yang et al., Evidence that processed small dsRNAs may mediate sequence-specific mRNA degradation during RNAi in *Drosophila* embryos. Curr. Biol., 10: 1191-200 (2000).

Ye et al., Characterization of a silencer regulatory element in the human interferon-gamma promoter, J. Biol. Chem., 269:25728-34 (1994).

Yin Win et al., Effects of particle size and surface coating on cellular uptake of polymeric nonparticles for oral delivery of anticancer drugs. Biomaterials, 26: 2713-22 (2005).

You et al., Detection and identification of proteins using nanoparticle-fluorescent polymer 'chemical nose' sensors. Nat. Nanotechnol., 2: 318-23 (2007).

You et al., Engineering the nanoparticle-biomacromolecule interface. Soft Matter, 2: 190-204 (2006).

Zabner et al., Cellular and molecular barriers to gene transfer by a cationic lipid. J. Biol. Chem., 270: 18997-9007 (1995).

Zamecnik et al., Inhibition of Rous sarcoma virus replication and cell transformation by a specific oligodeoxynucleotide. Proc. Natl. Acad. Sci. USA, 75(1): 280-4 (1978).

Zamore et al., RNAi: double-stranded RNA directs the ATP-dependent cleavage of mRNA at 21 to 23 nucleotide intervals. Cell, 101: 25-33 (2000).

Zhang et al., A novel paclitaxel-loaded poly(epsilon-caprolactone)/Poloxamer 188 blend nanoparticle overcoming multidrug resistance for cancer treatment, Acta Biomater., 6(6):2045-52 (2010).

Zhang et al., An extremely stable and orthogonal DNA base pair with a simplifed three-carbon backbone, J. Am. Chem. Soc., 127:74-5 (2005).

Zhang et al., Cationic shell-crosslinked knedel-like nanoparticles for highly efficient gene and oligonucleotide transfection of mammalian cells, Biomaterials, 30(5):968-77 (2009).

Zhang et al., Control of DNA strand displacement kinetics using toehold exchange. J. Am. Chem. Soc., 131: 17303-14 (2009).

Zhang et al., PowerBLAST: a new network BLAST application for interactive or automated sequence analysis and annotation, Genome Res., 7(6):649-56 (1997).

Zhang et al., PowerBlast: A new network BLAST application for interactive or automated sequence analysis and annotation. Genome, 7: 649-56 (1997).

Zhang et al., Self-assembled monolayers of terminal alkynes on gold, J. Am. Chem. Soc., 129(16):4876-7 (2007).

Zhang et al., Single-quantum-dot-based DNA sensor. Nat. Mater., 4: 826-31 (2005).

Zhao et al., A rapid bioassay for single bacterial cell quantitation using bioconjugated nanoparticles, Proc. Natl. Acad. Sci. USA, 101(42):15027-32 (2004).

Zheng et al., Aptamer nano-flares for molecular detection in living cells. Nano Lett., 9: 3258-61 (2009).

Zimmer, Antisense oligonucleotide delivery with polyhexylcyanoacrylate nanoparticles as carriers. Methods, 18: 286-95 (1999).

Zimmerman et al., A novel silver(I)-mediated DNA base pair, J. Am. Chem. Soc., 124:13684-5 (2002).

Combadiere et al., Particle-based vaccines for transcutaneous vaccination. *Comp. Immunol. Microbiol. Infect Dis*. 31: 293-315 (2008).

Cui et al., Topical immunization using nanoengineered genetic vaccines. *J. Control Rel*. 81: 173-84 (2002).

Fan, et al. "Immunization via hair follicles by topical application of naked DNA to normal skin," Nature Biotechnology 17:870-872 (1999).

Mehta "Topical and Transdermal Drug Delivery: What a Pharmacist Needs to Know," pp. 1-10 (2004).

Lewandowski et al., "Topically Delivered Tumor Necrosis Factor-α-Targeted Gene Regulation for Psoriasis," Journal of Investigative Dermatology 137:2027-2030 (2017).

Zheng et al., "Topical delivery of siRNA-based spherical nucleic acid nanoparticle conjugates for gene regulation," PNAS 109(30):11975-11980 (2012).

\* cited by examiner

DELIVERY OF OLIGONUCLEOTIDE FUNCTIONALIZED NANOPARTICLES

CROSS REFERENCE TO RELATED APPLICATIONS

This application is a continuation of U.S. patent application Ser. No. 12/724,395, filed Mar. 15, 2012, which claims the priority benefit under 35 U.S.C. § 119(e) of U.S. Provisional Application No. 61/187,759, filed Jun. 17, 2009. U.S. patent application Ser. No. 12/724,395 is a continuation-in-part of U.S. application Ser. No. 12/684,836,filed Jan. 8, 2010 which claims the priority benefit under 35 U.S.C. § 119(e) of U.S. Provisional Application No. 61/143,293, filed Jan. 8, 2009, and U.S. Provisional Application No. 61/169,384, filed Apr. 15, 2009, the disclosures of all of which are incorporated herein by reference in their entirety.

STATEMENT OF GOVERNMENT INTEREST

This invention was made with government support under Grant Numbers 5DP1 OD000285 and U54 CA119341, awarded by the National Institutes of Health (NIH). The government has certain rights in the invention.

FIELD OF THE INVENTION

The present invention is directed to oligonucleotide-modified nanoparticle (ON-NP) conjugates and methods of inhibiting bacterial protein production. The invention also relates to compositions and methods of delivering oligonucleotide-functionalized nanoparticle.

BACKGROUND OF THE INVENTION

Introduction of genetic material into cells and tissues for controlling gene expression has significantly impacted research involving gene pathways and function, and provides promise for therapeutic application. The genetic level approach has inherent specificity not available with the vast majority of drugs. siRNAs hold great promise as potential therapeutic tools and are currently in clinical trials, targeting a wide range of clinical problems including cancer. Gene silencing is much more cost-effective, and leads to down-regulation of protein expression and function with greater potential specificity than small molecule inhibitors. In particular, siRNA treatment may target a single point mutation in a gene, while small molecule therapy to date does not precisely distinguish between mutant and normal gene products. Given the ability to determine specific gene alterations in each melanoma through identification of hotspot mutations, direct gene sequencing, or assays for gene amplification, each melanoma can be assigned a specific genetic signature. Although the siRNA may be taken up by many cells, only cells with a mutated gene or activated signaling protein are affected by targeted gene therapy, thereby allowing normalization of pathway signaling in melanomas without adversely affecting normal cells.

As with delivery of many proteins, degradation of nucleic acids and poor bioavailability from the gastrointestinal tract are major hurdles to the oral delivery of siRNAs. Even with intravenous delivery, conventional siRNA is rapidly degraded by serum factors and does not reach its targets. Topical application of nucleic acids offers great therapeutic advantages, both for suppressing genes in lesional skin (for example and without limitation, to treat metastases in skin) and for transdermal delivery to internal targets. Application is painless and easily controlled, and skin is highly accessible. The effective physical barrier in the epidermis is localized mainly to the outermost area of epidermis, the stratum corneum, and to a lesser extent the deeper epidermis. This epidermal barrier protects against extensive water loss (inside-out) and against the entry of environmental substances (outside-in), including nucleic acids. Mechanical approaches, such as ultrasound, laser and injection, have been used to facilitate penetration through the mouse stratum corneum and drive siRNA into skin, but require specialized equipment, limit the area of delivery, and potentially harm the skin. These challenges emphasize the need for an easily applied transdermal system for delivering suppressive nucleic acids that is able to transit the stratum corneum.

Direct targeting of a skin disorder is an ideal model for gene suppressive therapy. However, the commercially available materials to suppress genes in vitro have been marginally successful, at best, for delivering genetic material into primary cultured cells, such as keratinocytes (KCs) and melanocytes. Furthermore, the outer layers of skin function as an anatomic barrier that traditionally prevents the penetration of nucleic acids and proteins into skin and, from dermis, into the circulation [Prausnitz et al., Nat Biotechnol 26: 1261-1268 (2008)]. Thus, traversing this layer to transfer sufficient amounts of oligonucleotides has been a challenge.

The skin is the largest organ of the body and contains three layers: the epidermis, dermis, and subcutaneous tissue. The epidermis is the outer layer of skin. The thickness of the epidermis varies in different types of skin. It is the thinnest on the eyelids at 0.05 mm and the thickest on the palms and soles at 1.5 mm. The epidermis contains 4 major layers of progressively more differentiated cells. From bottom to top the layers are named:

stratum basale
stratum spinosum
stratum granulosum
stratum corneum

The bottom layer, the stratum basale, has cells that are shaped like columns. In this layer the cells divide and push already-formed cells into higher layers. As the cells move into the higher layers, they flatten, become more mature and eventually "die" and are shed. The top layer of the epidermis, the stratum corneum, is made of flattened skin cells that are shed; it takes about 4 weeks from cells of the stratum basale to reach the stratum corneum and subsequently be shed.

SUMMARY OF THE INVENTION

The present disclosure provides compositions and methods for delivering an oligonucleotide-functionalized nanoparticle.

In some embodiments, the present disclosure provides a dermal composition comprising an oligonucleotide-functionalized nanoparticle (ON-NP) and a dermal vehicle.

Also provided by the present disclosure is a method of dermal delivery of an oligonucleotide-functionalized nanoparticle comprising the step of administering a composition comprising the oligonucleotide-functionalized nanoparticle and a dermal vehicle to the skin of a patient in need thereof.

In one aspect, the delivery of the oligonucleotide-functionalized nanoparticle is transdermal. In another aspect, the delivery of the oligonucleotide-functionalized nanoparticle is topical. In another aspect, the delivery of the oligonucleotide-functionalized nanoparticle is to the epidermis and dermis after topical application.

In some embodiments, the dermal vehicle comprises an ointment. In some aspects, the ointment is Aquaphor.

In another embodiment, a method of regulating gene expression is provided comprising the step of administering a therapeutically effective amount of a composition comprising an oligonucleotide-functionalized nanoparticle to skin under conditions wherein the oligonucleotide-functionalized nanoparticle hybridizes to a target and regulates gene expression.

In some aspects, the target is a polynucleotide. In related aspects, the polynucleotide is RNA. In some aspects, the target is a polypeptide.

In further embodiments of the present disclosure, the administration of the composition ameliorates a skin disorder.

In various embodiments, the skin disorder is selected from the group consisting of cancer, a genetic disorder, aging, inflammation, infection, and cosmetic disfigurement.

In some aspects, the cancer is selected from the group consisting of squamous cell carcinoma, basal cell carcinoma, breast cancer, and melanoma.

In still further embodiments, the target is a gene product expressed by a gene selected from the group consisting of Ras, IκBα, hedgehog, B-Raf, Akt and cyclin D.

In some aspects, the genetic disorder is selected from the group consisting of epidermolysis bullosa simplex, bullous ichthyosis, pachyonychia congenita, Costello syndrome and tuberous sclerosis. In further aspects, the target is a gene product that comprises a mutation, said gene product being expressed by a gene selected from the group consisting of K5, K14, K1, K10, H-Ras and m-Tor.

In some embodiments, the aging disorder is selected from the group consisting of UV-damage and progeria. In some aspects, the target is a gene product expressed by a gene selected from the group consisting of matrix metalloproteinase-1 and progerin.

In some embodiments, the inflammation is due to psoriasis. In some aspects, the target is interleukin-23.

In one embodiment, the viral infection results in warts. In some aspects, the target is E6/E7.

In further embodiments, the cosmetic disfigurement is selected from the group consisting of seborrheic keratoses, epidermal nevi and pigmented nevi. In various aspects, the target is a gene product comprising a mutation, said gene product being expressed by a gene selected from the group consisting of FGFR3, K10 and B-Raf.

DETAILED DESCRIPTION OF THE INVENTION

Figure 1:
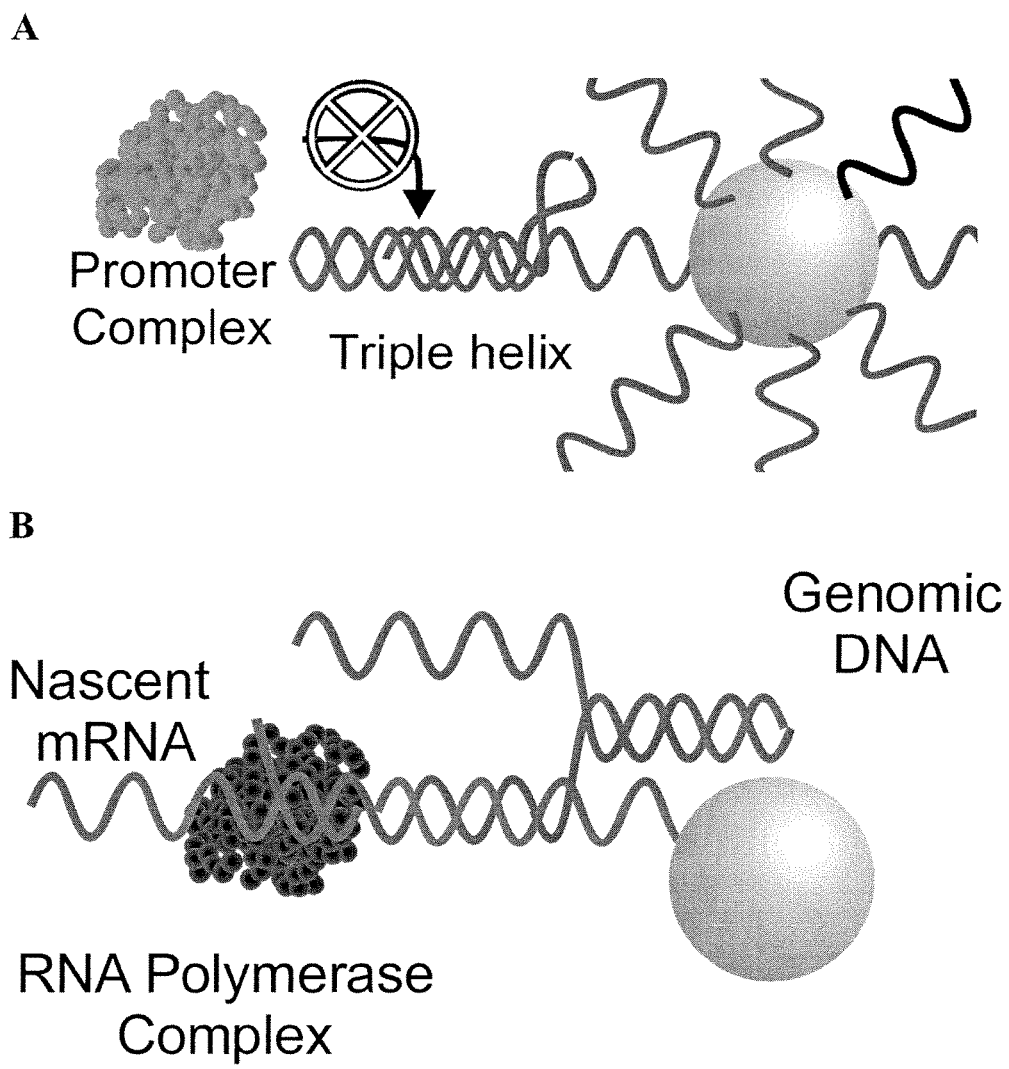
FIG. 1 depicts a schematic of oligonucleotide gold nanoparticle (Au-NP) conjugate blocking promoter complex binding (A) and full mRNA transcript formation (B) forming.

Disclosed herein is a nanoparticle delivery system that can be administered topically or transdermally for systemic delivery. In some embodiments, this system utilizes siRNA duplexes that are densely packed on the surface of nanoparticles (siRNA-NPs). These conjugates exhibit a number of unique properties that include but are not limited to: Retention of the oligonucleotide shell under biological conditions, resulting in a single agent capable of simultaneous transfection and gene regulation. Oligonucleotide-NPs (ON-NPs) are readily able to traverse cellular membranes without the addition of toxic transfection reagents. Importantly, these structures do not serve solely as vehicles for nucleic acid delivery, but remain conjugated as structures inside cells. Fluorescence spectroscopy studies reveal that the thiolated oligonucleotides remain bound to the NPs after cellular internalization, allowing one to take advantage of the composite properties of the nanomaterials. Another property exhibited by ON-NPs is their extraordinary stability in physiological environments. Unlike other nanomaterials and gene transfection reagents, oligonucleotide-NPs can be easily manipulated under biologically relevant conditions. These include high and low salt concentrations, extremes in pH, and fluctuations in temperature. An additional property of ON-NPs is their resistance to nuclease degradation. Since endo- and exo-nucleases are present in biological fluids and function to destroy foreign genetic material, methods for increasing the enzyme stability of nucleic acids are of paramount importance. While previous strategies to increase the enzyme stability of nucleic acids have relied on chemical modification, the enhanced resistance of oligonucleotide-NPs is unique in that it is based on dense functionalization of a nanoparticle surface. This environment creates a higher local dielectric within the vicinity of the nanoparticle surface, thus providing for both high affinity target recognition, and resistance to enzymatic degradation. A further property exhibited by ON-NPs is their ability to enter a variety of cell types, including "hard to transfect" primary cells without the use of auxiliary reagents. Another property of ON-NPs is their lack of apparent toxicity. These nanoconjugates have unique size, charge, and surface functionality, with properties derived from the combination of the oligonucleotide and the NP. Preliminary toxicology screening for these unique materials has shown no acute toxicity at high doses in animal models.

In is disclosed herein that topical application of ON-NPs is a novel means to deliver selective gene suppression to lesional skin, lymph nodes, or into the circulation for transdermal delivery to internal targets. In one embodiment, by delivering ON-NPs directly to lesional skin, oligonucleotide-NP concentration is maximized at the sites of maximal tumor load, while minimizing potential side effects.

In one aspect, the present disclosure provides an antibiotic composition and methods of its use. In one aspect, the antibiotic composition comprises a nanoparticle modified to include an oligonucleotide, wherein the oligonucleotide is sufficiently complementary to a target non-coding sequence of a prokaryotic gene such that the oligonucleotide will hybridize to the target sequence under conditions that allow hybridization. Through this hybridization, the antibiotic composition inhibits growth of the target prokaryotic cell. In the target cell, in certain aspects, hybridization inhibits expression of a functional protein encoded by the targeted sequence. In various aspects, transcription, translation or both of a prokaryotic protein encoded by the targeted sequence is inhibited. The disclosure further provides a method of utilizing the antibiotic composition disclosed herein for inhibiting production of a target prokaryotic gene product in a cell comprising the step of contacting the cell with the antibiotic composition, wherein the oligonucleotide associated with the nanoparticle of the composition is sufficiently complementary to a target non-coding sequence of a bacterial gene under conditions that allow hybridization, and wherein hybridization results in inhibition of a functional prokaryotic gene product encoded by the target gene. It will be appreciated by those of ordinary skill in the art that inhibition of either transcription or translation, or both transcription and translation, of the target prokaryotic sequence results in the inhibition of production of a functional protein encoded by the target prokaryotic sequence.

Hybridization of an oligonucleotide-functionalized nanoparticle and a target prokaryotic sequence forms a "complex" as defined herein. As used herein, a "complex" is either a double-strand (or duplex) complex or a triple-strand (or triplex) complex. It is contemplated herein that a triplex complex and a duplex complex inhibit translation or transcription of a target bacterial prokaryotic acid.

As used herein, a "non-coding sequence" has a meaning accepted in the art. In general, non-coding sequence describes a polynucleotide sequence that does not contain codons for translation a protein encoded by the gene. In some aspects, a non-coding sequence is chromosomal. In some aspects, a non-coding sequence is extra-chromosomal. In one aspect, a non-coding sequence is complementary to all or part of the coding sequence of the gene. Non-coding sequences include regulatory elements such as promoters, enhancers, and silencers of expression. Examples of non-coding sequences are 5' non-coding sequences and 3' non-coding sequences. A "5' non-coding sequence" refers to a polynucleotide sequence located 5' (upstream) to the coding sequence. The 5' non-coding sequence can be present in the fully processed mRNA upstream of the initiation codon and may affect processing of the primary transcript to mRNA, mRNA stability or translation efficiency. A "3' non-coding sequence" refers to nucleotide sequences located 3' (downstream) to a coding sequence and includes polyadenylation signal sequences and other sequences encoding signals capable of affecting mRNA processing or gene expression. The polyadenylation signal is usually characterized by its ability to affect the addition of polyadenylic acid sequences to the 3' end of the mRNA precursor.

In one embodiment, a non-coding sequence comprises a promoter. A "promoter" is a polynucleotide sequence that directs the transcription of a structural gene. Typically, a promoter is located in the 5' non-coding sequence of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements [DSEs; McGehee et al., *Mol. Endocrinol.* 7: 551 (1993)], cyclic AMP response elements (CREs), serum response elements [SREs; Treisman, Seminars in Cancer Biol. 1: 47 (1990)], glucocorticoid response elements (GREs), and binding sites for other transcription factors, such as CRE/ATF [O'Reilly et al., *J. Biol. Chem.* 267:19938 (1992)], AP2 [Ye et al., *J. Biol. Chem.* 269:25728 (1994)], SP1, cAMP response element binding protein [CREB; Loeken, Gene Expr. 3:253 (1993)] and octamer factors [see, in general, Watson et al., eds., Molecular Biology of the Gene, 4th ed. (The Benjamin/Cummings Publishing Company, Inc. 1987), and Lemaigre and Rousseau, *Biochem. J.* 303:1 (1994)]. If a promoter is an inducible promoter, then the rate of transcription increases in response to an inducing agent. In contrast, the rate of transcription is not regulated by an inducing agent if the promoter is a constitutive promoter. Repressible promoters are also known. A "core promoter" contains essential nucleotide sequences for promoter function, including the TATA box and start of transcription. By this definition, a core promoter may or may not have detectable activity in the absence of specific sequences that may enhance the activity or confer tissue specific activity.

In another embodiment, a non-coding sequence comprises a regulatory element. A "regulatory element" is a polynucleotide sequence that modulates the activity of a core promoter. For example, a regulatory element may contain a polynucleotide sequence that binds with cellular factors enabling transcription exclusively or preferentially in particular prokaryotes.

In another embodiment, a non-coding sequence comprises an enhancer. An "enhancer" is a type of regulatory element that can increase the efficiency of transcription, regardless of the distance or orientation of the enhancer relative to the start site of transcription.

It is noted here that, as used in this specification and the appended claims, the singular forms "a," "an," and "the" include plural reference unless the context clearly dictates otherwise.

It is to be noted that the terms "polynucleotide" and "oligonucleotide" are used interchangeably herein and have meanings accepted in the art.

It is further noted that the terms "attached", "conjugated", "modified" and "functionalized" are also used interchangeably herein and refer to the association of an oligonucleotide with a nanoparticle.

"Hybridization" means an interaction between two or three strands of nucleic acids by hydrogen bonds in accordance with the rules of Watson-Crick DNA complementarity, Hoogstein binding, or other sequence-specific binding known in the art. Hybridization can be performed under different stringency conditions known in the art.

The terms "oligonucleotide-functionalized nanoparticle" and "nanoconjugate" are used interchangeably herein.

As used herein, the melting temperature, or "T$_m$," is the temperature at which two specific nucleic acids that are hybridized are dissociated by 50%.

As used herein, the term "dermal" means of or relating to the skin, and is used interchangeably herein with "cutaneous." As used herein, "transdermal" means across the skin to the subcutaneous tissues and, often, into the systemic vascular or lymphatic circulation. The term "topical" as used herein means pertaining to the skin. Thus, when a composition is applied topically, it is applied to the skin. It will be understood by those of ordinary skill in the art, however, that the term "topical" does not necessarily refer to where the composition will remain, but rather how it is applied.

Compositions and methods of the present disclosure are, in various embodiments, contemplated to target different depths of skin depending on, for example and without limitation, a particular target of interest. In various embodiments, the compositions of the present disclosure target the epidermis. In some embodiments, the compositions of the present disclosure target the dermis. In further embodiments, the compositions of the present disclosure travel transdermally and reach subcutaneous tissue, the systemic vasculature or lymphatic circulation.

Factors that affect the depth of penetration of the compositions and methods of the present disclosure include, but are not limited to, the size of the nanoparticle and the density of functionalized oligonucleotides on the surface of the nanoparticle. These aspects are described in further detail herein below. Thus, in some aspects the present disclosure contemplates that the oligonucleotide-functionalized nanoparticle itself facilitates the depth to which the compositions of the present disclosure can travel. In some aspects, the vehicle in the composition facilitates the depth to which the compositions of the present disclosure can travel. In still further aspects, the combination of the vehicle and oligonucleotide-functionalized nanoparticle together facilitate the depth to which the compositions of the present disclosure can travel.

Melanomas represent a heterogeneous group of tumors, with different patterns of oncogenic mutation and genomic amplification. Progression from a precursor lesion, such as a pigmented nevus, to melanoma is thought to follow a stepwise pathway with genetic change leading to activation of signaling pathways. Most common is activation of the RAS/RAF/MEK/ERK pathway (approximately 60% of melanomas have activating BRAF mutations and 25% NRAS mutations). Sun-exposed sites most commonly show BRAF mutations, whereas the less common mucosal or acral sites rarely show BRAF mutations.

More than 95% of the BRAF mutations [Dhomen et al., Hematol Oncol Clin North Am 23, 529-545, ix (2009)] is a point mutation (T1799A) that substitutes valine for glutamic acid (V600E) and increases BRAF activation 500-fold. This mutation leads to hyperactive melanocyte ERK signaling and growth factor-independent proliferation of explanted tumors in mouse models [Wellbrock et al., Cancer Res. 64(7): 2338-42 (2004)].

Activation of the BRAF/ERK pathway alone, however, does not explain melanoma transformation. Indeed, metastatic melanomas tend to harbor more than one gene alteration [Goel et al., Oncogene 28: 2289-2298 (2009)](see Table A, below), most commonly leading to activation of the phosphoinositide 3-kinase (PI3K)/protein kinase B (AKT) pathway (~70% of sporadic melanomas) [Cheung et al., Cancer Res 68: 3429-3439 (2008)], in addition to BRAF/ERK activation. The critical role of constitutive PI3K/AKT activation in the BRAF V600E mutation-mediated development of melanoma has now been demonstrated in both in vitro and mouse studies. BRAF mutations are frequently found in combination with either PTEN loss/inactivation (~30% of cell lines and at least 58% of melanoma metastases)(Birck et al., 2000) or activating AKT3 mutations (43-50% of melanomas) [Davies et al., Br J Cancer 99: 1265-1268 (2008); Lin et al., Cancer Res 68: 664-673 (2008); Stahl et al., Cancer Res 64: 7002-7010 (2004); Tsao et al., J Invest Dermatol 122: 337-341 (2004)].

TABLE A

Genotypes of selected melanocytic cells and melanoma cell lines

| Cell line | Genetic change | Metastases |
|---|---|---|
| Normal human melanocytes | None | None |
| BRAF$^{V/E}$PTEN$^{lox}$ (mouse) | Braf V600E (inducible by 4-HT), PTEN loss | Lungs, Lymph Node |
| SK-MEL28 | Homozygous BRAF V600E, CDK4 R24C, PTEN T167A, p53 L145R, wildtype c-KIT, NRAS, CDKN2a | Lungs, liver |
| 1205Lu | Hemizygous BRAF V600E, CDK4 K22Q, PTEN MU/Hem del, CDKN2a mut, wildtype c-KIT, NRAS, p53 | Lung |
| A375P | BRAF V600E, wildtype CDK4, PTEN, p53, c-KIT, NRAS, CDKN2a | None |
| C8161 | AKT activation, but no BRAF mutation; other mutations unknown | Lung, liver |

Antibiotic Compositions

In some embodiments, the present disclosure provides antibiotic compositions comprising an oligonucleotide-modified nanoparticle and a vehicle, wherein the oligonucleotide is sufficiently complementary to a target non-coding sequence of a prokaryotic gene that it will hybridize to the target sequence under conditions that allow hybridization. In various embodiments, the antibiotic compositions are formulated for administration in a therapeutically effective amount to a mammal in need thereof for the treatment of a prokaryotic cell infection. In some aspects, the mammal is a human.

In various embodiments, it is contemplated that hybridization of the oligonucleotide-modified nanoparticle to a prokaryotic gene inhibits (or prevents) the growth of a prokaryotic cell. Thus, the hybridization of the oligonucleotide-modified nanoparticle to a prokaryotic gene is contemplated to result in a bacteriostatic or bactericidal effect in aspects wherein the prokaryote is bacteria. In aspects wherein the hybridization occurs in vivo, the growth of the prokaryotic cell is inhibited by about 5% compared to the growth of the prokaryotic cell in the absence of contact with the oligonucleotide-modified nanoparticle. In various aspects, the growth of the prokaryotic cell is inhibited by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 2-fold, about 3-fold, about 4-fold, about 5-fold, about 6-fold, about 7-fold, about 8-fold, about 9-fold, about 10-fold, about 20-fold, about 50-fold or more compared to the growth of the prokaryotic cell in the absence of contact with the oligonucleotide-modified nanoparticle.

In aspects wherein the hybridization occurs in vitro, the growth of the prokaryotic cell is inhibited by about 5% compared to the growth of the prokaryotic cell in the absence of contact with the oligonucleotide-modified nanoparticle. In various aspects, the growth of the prokaryotic cell is inhibited by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 2-fold, about 3-fold, about 4-fold, about 5-fold, about 6-fold, about 7-fold, about 8-fold, about 9-fold, about 10-fold, about 20-fold, about 50-fold or more compared to the growth of the prokaryotic cell in the absence of contact with the oligonucleotide-modified nanoparticle.

Whether the inhibition is in vivo or in vitro, one of ordinary skill in the art can determine the level of inhibition of prokaryotic cell growth using routine techniques. For example, direct quantitation of the number of prokaryotic cells is performed by obtaining a set of samples (e.g., a bodily fluid in the case of in vivo inhibition or a liquid culture sample in the case of in vitro inhibition) wherein the samples are collected over a period of time, culturing the samples on solid growth-permissive media and counting the resultant number of prokaryotic cells that are able to grow. The number of prokaryotic cells at a later time point versus the number of prokaryotic cells at an earlier time point yields the percent inhibition of prokaryotic cell growth.

In some embodiments, hybridization of the oligonucleotide-modified nanoparticle to a prokaryotic gene inhibits expression of a functional prokaryotic protein encoded by the prokaryotic gene. A "functional prokaryotic protein" as used herein refers to a full length wild type protein encoded by a prokaryotic gene. In one aspect, the expression of the functional prokaryotic protein is inhibited by about 5% compared to a cell that is not contacted with the oligonucleotide-modified nanoparticle. In various aspects, the expression of the functional prokaryotic protein is inhibited by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 2-fold, about 3-fold, about 4-fold, about 5-fold, about 6-fold, about 7-fold, about 8-fold, about 9-fold, about 10-fold, about 20-fold, about 50-fold or more compared to a cell that is not contacted with the oligonucleotide-modified nanoparticle. In other words, methods provided embrace those which results in any degree of inhibition of expression of a target gene product.

In related aspects, the hybridization of the oligonucleotide-modified nanoparticle to a prokaryotic gene inhibits expression of a functional protein essential for prokaryotic cell growth. In one aspect, the expression of the functional prokaryotic protein essential for prokaryotic cell growth is inhibited by about 5% compared to a cell that is not contacted with the oligonucleotide-modified nanoparticle. In various aspects, the expression of the functional prokaryotic protein essential for prokaryotic cell growth is inhibited by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 2-fold, about 3-fold, about 4-fold, about 5-fold, about 6-fold, about 7-fold, about 8-fold, about 9-fold, about 10-fold, about 20-fold, about 50-fold or more compared to a cell that is not contacted with the oligonucleotide-modified nanoparticle.

Prokaryotic proteins essential for growth include, but are not limited to, a gram-negative gene product, a gram-positive gene product, cell cycle gene product, a gene product involved in DNA replication, a cell division gene product, a gene product involved in protein synthesis, a bacterial gyrase, and an acyl carrier gene product. These classes are discussed in detail herein below.

The present disclosure also contemplates an antibiotic composition wherein hybridization to a target non-coding sequence of a prokaryotic gene results in expression of a protein encoded by the prokaryotic gene with altered activity. In one aspect, the activity of the protein encoded by the prokaryotic gene is reduced about 5% compared to the activity of the protein in a prokaryotic cell that is not contacted with the oligonucleotide-modified nanoparticle. In various aspects, activity of the prokaryotic protein is inhibited by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98% about 99% or about 100% compared to the activity of the protein in a prokaryotic cell that is not contacted with the oligonucleotide-modified nanoparticle. In another aspect, the activity of the protein encoded by the prokaryotic gene is increased about 5% compared to the activity of the protein in a prokaryotic cell that is not contacted with the oligonucleotide-modified nanoparticle. In various aspects, the expression of the prokaryotic protein is increased by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 2-fold, about 3-fold, about 4-fold, about 5-fold, about 6-fold, about 7-fold, about 8-fold, about 9-fold, about 10-fold, about 20-fold, about 50-fold or more compared to the activity of the protein in a prokaryotic cell that is not contacted with the oligonucleotide-modified nanoparticle.

The activity of the protein in a prokaryotic cell is increased or decreased as a function of several parameters including but not limited to the sequence of the oligonucleotide attached to the nanoparticle, the prokaryotic gene (and the protein encoded by the gene) that is targeted, and the size of the nanoparticle.

In various embodiments, it is contemplated that the antibiotic composition of the present disclosure inhibits transcription of the prokaryotic gene. In some embodiments, it is contemplated that the antibiotic composition of the present disclosure inhibits translation of the prokaryotic gene.

In some embodiments, the antibiotic composition hybridizes to a target non-coding sequence of a prokaryotic gene that confers a resistance to an antibiotic. These genes are known to those of ordinary skill in the art and are discussed, e.g., in Liu et al., Nucleic Acids Research 37: D443-D447, 2009 (incorporated herein by reference in its entirety). In some aspects, hybridization of the antibiotic composition to a target non-coding sequence of a prokaryotic gene that confers a resistance to an antibiotic results in increasing the susceptibility of the prokaryote to an antibiotic. In one aspect, the susceptibility of the prokaryote to the antibiotic is increased by about 5% compared to the susceptibility of the prokaryote that was not contacted with the antibiotic composition. In various aspects, the susceptibility of the prokaryote to the antibiotic is increased by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 2-fold, about 3-fold, about 4-fold, about 5-fold, about 6-fold, about 7-fold, about 8-fold, about 9-fold, about 10-fold, about 20-fold, about 50-fold or more compared to the susceptibility of the prokaryote that was not contacted with the antibiotic composition. Relative susceptibility to an antibiotic can be determined by those of ordinary skill in the art using routine techniques as described herein.

Combination Therapy with Antibiotics

In some embodiments, the antibiotic composition comprising the oligonucleotide-modified nanoparticle conjugates are formulated for administration in combination with an antibiotic agent, each in a therapeutically effective amount.

The term "antibiotic agent" as used herein means any of a group of chemical substances having the capacity to inhibit the growth of, or to kill bacteria, and other microorganisms, used chiefly in the treatment of infectious diseases. See, e.g., U.S. Pat. No. 7,638,557 (incorporated by reference herein in its entirety). Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefinetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

Dosing and Pharmaceutical Compositions

The term "therapeutically effective amount", as used herein, refers to an amount of a composition sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by an assay described herein. The precise effective amount for a subject will depend upon the subject's body weight, size, and health; the nature and extent of the condition; and the antibiotic composition or combination of compositions selected for administration. Therapeutically effective amounts for a given situation can be determined by routine experimentation that is within the skill and judgment of the clinician.

The compositions described herein may be formulated in pharmaceutical compositions with a pharmaceutically acceptable excipient, carrier, or diluent. The compound or composition can be administered by any route that permits treatment of the prokaryotic infection or condition. As described herein, compositions of the present disclosure that comprise an ON-NP and a vehicle are provided that are useful for topical application. An additional route of administration is oral administration. Additionally, the compound or composition may be delivered to a patient using any standard route of administration, including parenterally, such as intravenously, intraperitoneally, intrapulmonary, subcutaneously or intramuscularly, intrathecally, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration may take the form of single dose administration, or the compound of the embodiments can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions comprises in various aspects a therapeutically or prophylactically effective amount of at least one composition as described herein, together with one or more pharmaceutically acceptable excipients. As described herein, the pharmaceutical compositions may optionally comprise a combination of the compounds described herein.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using suitable dispersing or wetting agents and suspending agents. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

Inhibition of Prokaryotic Protein

In some aspects, the disclosure provides methods of targeting specific nucleic acids. Any type of prokaryotic nucleic acid may be targeted, and the methods may be used, e.g., for inhibition of production of a functional prokaryotic gene product. Examples of nucleic acids that can be targeted by the methods of the invention include but are not limited to genes and prokaryotic RNA or DNA.

For prokaryotic target nucleic acid, in various aspects, the nucleic acid is RNA transcribed from genomic DNA.

The degree of inhibition is determined in vivo from, for example a body fluid sample of an individual in whom the target prokaryote is found and for which inhibition of a prokaryotic protein is desirable, or by imaging techniques in an individual in whom the target prokaryote is found and for which inhibition of a prokaryotic protein is desirable, well known in the art. Alternatively, the degree of inhibition is determined in vivo by quantitating the amount of a prokaryote that remains in cell culture or an organism compared to the amount of a prokaryote that was in cell culture or an organism at an earlier time point.

In embodiments where a triplex complex is formed, it is contemplated that a mutation is introduced to the prokaryotic genome. In these embodiments, the oligonucleotide-modified nanoparticle conjugate comprises the mutation and formation of a triplex complex initiates a recombination event between the oligonucleotide attached to the nanoparticle and a strand of the prokaryotic genome.

Oligonucleotide Hybridization and Design

The oligonucleotide of the present disclosure has a $T_m$, when hybridized with the target polynucleotide sequence, of at least about 45° C., typically between about 50° to 60° C., although the $T_m$ may be higher, e.g., 65° C. In aspects wherein the target is a prokaryotic polynucleotide, the selection of prokaryotic target polynucleotide sequence, and prokaryotic mRNA target polynucleotide sequences are considered herein below.

In one embodiment, the oligonucleotides of the invention are designed to hybridize to a target oligonucleotide sequence under physiological conditions, with a $T_m$ substantially greater than 37° C., e.g., at least 45° C. and, in some aspects, approximately 60° C.-80° C. The oligonucleotide is designed to have high binding affinity to the nucleic acid and, in one aspect, is 100% complementary to the target oligonucleotide sequence, or it may include mismatches. Methods are provided in which the oligonucleotide is greater than 95% complementary to the target oligonucleotide sequence, greater than 90% complementary to the target oligonucleotide sequence, greater than 80% complementary to the target oligonucleotide sequence, greater than 75% complementary to the target oligonucleotide sequence, greater than 70% complementary to the target oligonucleotide sequence, greater than 65% complementary to the target oligonucleotide sequence, greater than 60% complementary to the target oligonucleotide sequence, greater than 55% complementary to the target oligonucleotide sequence, or greater than 50% complementary to the target oligonucleotide sequence.

It will be understood that one of skill in the art may readily determine appropriate targets for oligonucleotide modified nanoparticle conjugates, and design and synthesize oligonucleotides using techniques known in the art. Targets can be identified by obtaining, e.g., the sequence of a target nucleic acid of interest (e.g. from GenBank) and aligning it with other nucleic acid sequences using, for example, the MacVector 6.0 program, a ClustalW algorithm, the BLOSUM 30 matrix, and default parameters, which include an open gap penalty of 10 and an extended gap penalty of 5.0 for nucleic acid alignments.

Any essential prokaryotic gene is contemplated as a target gene using the methods of the present disclosure. As described above, an essential prokaryotic gene for any prokaryotic species can be determined using a variety of methods including those described by Gerdes for *E. coli* [Gerdes et al., *J. Bacteriol.* 185(19): 5673-84, 2003]. Many essential genes are conserved across the bacterial kingdom thereby providing additional guidance in target selection. Target gene sequences can be identified using readily available bioinformatics resources such as those maintained by the National Center for Biotechnology Information (NCBI). Complete reference genomic sequences for a large number of microbial species can be obtained and sequences for essential bacterial genes identified. Bacterial strains are also in one aspect obtained from the American Type Culture Collection (ATCC). Simple cell culture methods, using the appropriate culture medium and conditions for any given species, can be established to determine the antibacterial activity of oligonucleotide modified nanoparticle conjugates.

Oligonucleotide modified nanoparticle conjugates showing optimal activity are then tested in animal models, or veterinary animals, prior to use for treating human infection.

Therapeutic Targets

Target Sequences for Cell-Division and Cell-Cycle Target Proteins

The oligonucleotides of the present disclosure are designed to hybridize to a sequence of a prokaryotic nucleic acid that encodes an essential prokaryotic gene. Exemplary genes include but are not limited to those required for cell division, cell cycle proteins, or genes required for lipid biosynthesis or nucleic acid replication. Any essential bacterial gene is a target once a gene's essentiality is determined. One approach to determining which genes in an organism are essential is to use genetic footprinting techniques as described [Gerdes et al., *J. Bacteriol.* 185(19): 5673-84, 2003, incorporated by reference herein in its entirety]. In this report, 620 *E. coli* genes were identified as essential and 3,126 genes as dispensable for growth under culture conditions for robust aerobic growth. Evolutionary context analysis demonstrated that a significant number of essential *E. coli* genes are preserved throughout the bacterial kingdom, especially the subset of genes for key cellular processes such as DNA replication, cell division and protein synthesis.

In various aspects, the present disclosure provides an oligonucleotide that is a nucleic acid sequence effective to stably and specifically bind to a target sequence which encodes an essential bacterial protein including the following: (1) a sequence specific to a particular strain of a given species of bacteria, such as a strain of *E. coli* associated with food poisoning, e.g., O157:H7 (see Table 1 of U.S. Patent Application Number 20080194463, incorporated by reference herein in its entirety); (2) a sequence common to two or more species of bacteria; (3) a sequence common to two related genera of bacteria (i.e., bacterial genera of similar phylogenetic origin); (4) a sequence generally conserved among Gram-negative bacteria; (5) generally conserved among Gram-positive bacteria; or (6) a consensus sequence for essential bacterial protein-encoding nucleic acid sequences in general.

In general, the target for modulation of gene expression using the methods of the present disclosure comprises a prokaryotic nucleic acid expressed during active prokaryotic growth or replication, such as an mRNA sequence transcribed from a gene of the cell division and cell wall synthesis (division cell wall or dcw) gene cluster, including, but not limited to, zipA, sulA, secA, dicA, dicB, dicC, dicF, ftsA, ftsI, ftsN, ftsK, ftsL, ftsQ, ftsW, ftsZ, murC, murD, murE, murF, murg, minC, minD, minE, mraY, mraW, mraZ, seqA and ddlB. See [Bramhill, *Annu Rev Cell Dev Biol.* 13: 395-424, 1997], and [Donachie, *Annu Rev Microbiol.* 47: 199-230, 1993], both of which are expressly incorporated by reference herein, for general reviews of bacterial cell division and the cell cycle of *E. coli*, respectively. Additional targets include genes involved in lipid biosynthesis (e.g. acpP) and replication (e.g. gyrA).

Cell division in *E. coli* involves coordinated invagination of all 3 layers of the cell envelope (cytoplasmic membrane, rigid peptidoglycan layer and outer membrane). Constriction of the septum severs the cell into two compartments and segregates the replicated DNA. At least 9 essential gene products participate in this process: ftsZ, ftsA, ftsQ, ftsL, ftsI, ftsN, ftsK, ftsW and zipA [Hale et al., *J. Bacteriol.* 181(1): 167-76, 1999]. Contemplated protein targets are the three discussed below, and in particular, the GyrA and AcpP targets described below.

FtsZ, one of the earliest essential cell division genes in *E. coli*, is a soluble, tubulin-like GTPase that forms a membrane-associated ring at the division site of bacterial cells. The ring is thought to drive cell constriction, and appears to affect cell wall invagination. FtsZ binds directly to a novel integral inner membrane protein in *E. coli* called zipA, an essential component of the septal ring structure that mediates cell division in *E. coli* [Lutkenhaus et al., *Annu Rev Biochem.* 66: 93-116, 1997].

GyrA refers to subunit A of the bacterial gyrase enzyme, and the gene therefore. Bacterial gyrase is one of the bacterial DNA topoisomerases that control the level of supercoiling of DNA in cells and is required for DNA replication.

AcpP encodes acyl carrier protein, an essential cofactor in lipid biosynthesis. The fatty acid biosynthetic pathway requires that the heat stable cofactor acyl carrier protein binds intermediates in the pathway.

For each of these three proteins, Table 1 of U.S. Patent Application Number 20080194463 provides exemplary bacterial sequences which contain a target sequence for each of a number of important pathogenic bacteria. The gene sequences are derived from the GenBank Reference full genome sequence for each bacterial strain.

Target Sequences for Prokaryotic 16S Ribosomal RNA

In one embodiment, the oligonucleotides of the invention are designed to hybridize to a sequence encoding a bacterial 16S rRNA nucleic acid sequence under physiological conditions, with a $T_m$ substantially greater than 37° C., e.g., at least 45° C. and preferably 60° C.-80° C.

More particularly, the oligonucleotide has a sequence that is effective to stably and specifically bind to a target 16S rRNA egne sequence which has one or more of the following characteristics: (1) a sequence found in a double stranded sequence of a 16s rRNA, e.g., the peptidyl transferase center, the alpha-sarcin loop and the mRNA binding sequence of the 16S rRNA sequence; (2) a sequence found in a single stranded sequence of a bacterial 16s rRNA; (3) a sequence specific to a particular strain of a given species of bacteria, i.e., a strain of *E. coli* associated with food poisoning; (4) a sequence specific to a particular species of bacteria; (5) a sequence common to two or more species of bacteria; (6) a sequence common to two related genera of bacteria (i.e., bacterial genera of similar phylogenetic origin); (7) a sequence generally conserved among Gram-negative bacterial 16S rRNA sequences; (6) a sequence generally conserved among Gram-positive bacterial 16S rRNA sequences; or (7) a consensus sequence for bacterial 16S rRNA sequences in general.

Exemplary bacteria and associated GenBank Accession Nos. for 16S rRNA sequences are provided in Table 1 of U.S. Pat. No. 6,677,153, incorporated by reference herein in its entirety.

*Escherichia coli* (*E. coli*) is a Gram-negative bacterium that is part of the normal flora of the gastrointestinal tract. There are hundreds of strains of *E. coli*, most of which are harmless and live in the gastrointestinal tract of healthy humans and animals. Currently, there are four recognized classes of enterovirulent *E. coli* (the "EEC group") that cause gastroenteritis in humans. Among these are the enteropathogenic (EPEC) strains and those whose virulence mechanism is related to the excretion of typical *E. coli* enterotoxins. Such strains of *E. coli* can cause various diseases including those associated with infection of the gastrointestinal tract and urinary tract, septicemia, pneumonia, and meningitis. Antibiotics are not effective against some strains and do not necessarily prevent recurrence of infection.

For example, *E. coli* strain 0157:H7 is estimated to cause 10,000 to 20,000 cases of infection in the United States annually (Federal Centers for Disease Control and Prevention). Hemorrhagic colitis is the name of the acute disease caused by *E. coli* O157:H7. Preschool children and the elderly are at the greatest risk of serious complications. *E. coli* strain 0157:H7 was recently reported as the cause the death of four children who ate under-cooked hamburgers from a fast-food restaurant in the Pacific Northwest. [See, e.g., Jackson et al., *Epidemiol. Infect.* 120(1):17-20, 1998].

Exemplary sequences for enterovirulent *E. coli* strains include GenBank Accession Numbers X97542, AF074613, Y11275 and AJ007716.

*Salmonella typhimurium*, are Gram-negative bacteria that cause various conditions that range clinically from localized gastrointestinal infections, gastroenteritis (diarrhea, abdominal cramps, and fever) to enteric fevers (including typhoid fever) which are serious systemic illnesses. *Salmonella* infection also causes substantial losses of livestock.

Typical of Gram-negative bacilli, the cell wall of *Salmonella* spp. contains a complex lipopolysaccharide (LPS) structure that is liberated upon lysis of the cell and may function as an endotoxin, which contributes to the virulence of the organism.

Contaminated food is the major mode of transmission for non-typhoidal *salmonella* infection, due to the fact that *Salmonella* survive in meats and animal products that are not thoroughly cooked. The most common animal sources are chickens, turkeys, pigs, and cows; in addition to numerous other domestic and wild animals. The epidemiology of typhoid fever and other enteric fevers caused by *Salmonella* spp. is associated with water contaminated with human feces.

Vaccines are available for typhoid fever and are partially effective; however, no vaccines are available for non-typhoidal *Salmonella* infection. Non-typhoidal salmonellosis is controlled by hygienic slaughtering practices and thorough cooking and refrigeration of food. Antibiotics are indicated for systemic disease, and Ampicillin has been used with some success. However, in patients under treatment with excessive amounts of antibiotics, patients under treatment with immunosuppressive drugs, following gastric surgery, and in patients with hemolytic anemia, leukemia, lymphoma, or AIDS, *Salmonella* infection remains a medical problem.

*Pseudomonas* spp. are motile, Gram-negative rods which are clinically important because they are resistant to most antibiotics, and are a major cause of hospital acquired (nosocomial) infections. Infection is most common in immunocompromised individuals, burn victims, individuals on respirators, individuals with indwelling catheters, IV narcotic users and individual with chronic pulmonary disease (e.g., cystic fibrosis). Although infection is rare in healthy individuals, it can occur at many sites and lead to urinary tract infections, sepsis, pneumonia, pharyngitis, and numerous other problems, and treatment often fails with greater significant mortality.

*Pseudomonas aeruginosa* is a Gram-negative, aerobic, rod-shaped bacterium with unipolar motility. An opportunistic human pathogen, *P. aeruginosa* is also an opportunistic pathogen of plants. Like other Pseudomonads, *P. aeruginosa* secretes a variety of pigments. Definitive clinical identification of *P. aeruginosa* can include identifying the production of both pyocyanin and fluorescein as well as the organism's ability to grow at 42° C. *P. aeruginosa* is also capable of growth in diesel and jet fuel, for which it is known as a hydrocarbon utilizing microorganism (or "HUM bug"), causing microbial corrosion.

*Vibrio cholera* is a Gram-negative rod which infects humans and causes cholera, a disease spread by poor sanitation, resulting in contaminated water supplies. *Vibrio cholerae* can colonize the human small intestine, where it produces a toxin that disrupts ion transport across the mucosa, causing diarrhea and water loss. Individuals infected with *Vibrio cholerae* require rehydration either intravenously or orally with a solution containing electrolytes. The illness is generally self-limiting; however, death can occur from dehydration and loss of essential electrolytes. Antibiotics such as tetracycline have been demonstrated to shorten the course of the illness, and oral vaccines are currently under development.

*Neisseria gonorrhoea* is a Gram-negative coccus, which is the causative agent of the common sexually transmitted disease, gonorrhea. *Neisseria gonorrhoea* can vary its surface antigens, preventing development of immunity to reinfection. Nearly 750,000 cases of gonorrhea are reported annually in the United States, with an estimated 750,000 additional unreported cases annually, mostly among teenagers and young adults. Ampicillin, amoxicillin, or some type of penicillin used to be recommended for the treatment of gonorrhea. However, the incidence of penicillin-resistant gonorrhea is increasing, and new antibiotics given by injection, e.g., ceftriaxone or spectinomycin, are now used to treat most gonococcal infections.

*Staphylococcus aureus* is a Gram-positive coccus which normally colonizes the human nose and is sometimes found on the skin. *Staphylococcus* can cause bloodstream infections, pneumonia, and nosocomial infections. *Staph. aureus* can cause severe food poisoning, and many strains grow in food and produce exotoxins. *Staphylococcus* resistance to common antibiotics, e.g., vancomycin, has emerged in the United States and abroad as a major public health challenge both in community and hospital settings. Recently, a vancomycin-resistant *Staph. aureus* isolate has also been identified in Japan.

*Mycobacterium tuberculosis* is a Gram positive bacterium which is the causative agent of tuberculosis, a sometimes crippling and deadly disease. Tuberculosis is on the rise and globally and the leading cause of death from a single infectious disease (with a current death rate of three million people per year). It can affect several organs of the human body, including the brain, the kidneys and the bones, however, tuberculosis most commonly affects the lungs.

In the United States, approximately ten million individuals are infected with *Mycobacterium tuberculosis*, as indicated by positive skin tests, with approximately 26,000 new cases of active disease each year. The increase in tuberculosis (TB) cases has been associated with HIV/AIDS, homelessness, drug abuse and immigration of persons with active infections. Current treatment programs for drug-susceptible TB involve taking two or four drugs (e.g., isoniazid, rifampin, pyrazinamide, ethambutol or streptomycin), for a period of from six to nine months, because all of the TB germs cannot be destroyed by a single drug. In addition, the observation of drug-resistant and multiple drug resistant strains of *Mycobacterium tuberculosis* is on the rise.

*Helicobacter pylori* (*H. pylori*) is a micro-aerophilic, Gram-negative, slow-growing, flagellated organism with a spiral or S-shaped morphology which infects the lining of the stomach. *H. pylori* is a human gastric pathogen associated with chronic superficial gastritis, peptic ulcer disease, and chronic atrophic gastritis leading to gastric adenocarcinoma. *H. pylori* is one of the most common chronic bacterial infections in humans and is found in over 90% of patients with active gastritis. Current treatment includes triple drug therapy with bismuth, metronidazole, and either tetracycline or amoxicillin which eradicates *H. pylori* in most cases. Problems with triple therapy include patient compliance, side effects, and metronidazole resistance. Alternate regimens of dual therapy which show promise are amoxicillin plus metronidazole or omeprazole plus amoxicillin.

*Streptococcus pneumoniae* is a Gram-positive coccus and one of the most common causes of bacterial pneumonia as well as middle ear infections (otitis media) and meningitis.

Each year in the United States, pneumococcal diseases account for approximately 50,000 cases of bacteremia; 3,000 cases of meningitis; 100,000-135,000 hospitalizations; and 7 million cases of otitis media. Pneumococcal infections cause an estimated 40,000 deaths annually in the United States. Children less than 2 years of age, adults over 65 years of age and persons of any age with underlying medical conditions, including, e.g., congestive heart disease, diabetes, emphysema, liver disease, sickle cell, HIV, and those living in special environments, e.g., nursing homes and long-term care facilities, at highest risk for infection.

Drug-resistant *S. pneumoniae* strains have become common in the United States, with many penicillin-resistant pneumococci also resistant to other antimicrobial drugs, such as erythromycin or trimethoprim-sulfamethoxazole.

*Treponema pallidum* is a spirochete which causes syphilis. *T. pallidum* is exclusively a pathogen which causes syphilis, yaws and non-venereal endemic syphilis or pinta. *Treponema pallidum* cannot be grown in vitro and does replicate in the absence of mammalian cells. The initial infection causes an ulcer at the site of infection; however, the bacteria move throughout the body, damaging many organs over time. In its late stages, untreated syphilis, although not contagious, can cause serious heart abnormalities, mental disorders, blindness, other neurologic problems, and death.

Syphilis is usually treated with penicillin, administered by injection. Other antibiotics are available for patients allergic to penicillin, or who do not respond to the usual doses of penicillin. In all stages of syphilis, proper treatment will cure the disease, but in late syphilis, damage already done to body organs cannot be reversed.

*Chlamydia trachomatis* is the most common bacterial sexually transmitted disease in the United States and it is estimated that 4 million new cases occur each year. The highest rates of infection are in 15 to 19 year olds. *Chlamydia* is a major cause of non-gonococcal urethritis (NGU), cervicitis, bacterial vaginitis, and pelvic inflammatory disease (PID). *Chlamydia* infections may have very mild symptoms or no symptoms at all; however, if left untreated *Chlamydia* infections can lead to serious damage to the reproductive organs, particularly in women. Antibiotics such as azithromycin, erythromycin, of Iloxacin, amoxicillin or doxycycline are typically prescribed to treat *Chlamydia* infection.

*Bartonella henselae* Cat Scratch Fever (CSF) or cat scratch disease (CSD), is a disease of humans acquired through exposure to cats, caused by a Gram-negative rod originally named *Rochalimaea henselae*, and currently known as *Bartonella henselae*. Symptoms include fever and swollen lymph nodes and CSF is generally a relatively benign, self-limiting disease in people, however, infection with *Bartonella henselae* can produce distinct clinical symptoms in immunocompromised people, including, acute febrile illness with bacteremia, bacillary angiomatosis, peliosis hepatis, bacillary splenitis, and other chronic disease manifestations such as AIDS encephalopathy. The disease is treated with antibiotics, such as doxycycline, erythromycin, rifampin, penicillin, gentamycin, ceftriaxone, ciprofloxacin, and azithromycin.

*Haemophilus influenzae* (*H. influenza*) is a family of Gram-negative bacteria; six types of which are known, with most *H. influenza*-related disease caused by type B, or "HIB". Until a vaccine for HIB was developed, HIB was a common causes of otitis media, sinus infections, bronchitis, the most common cause of meningitis, and a frequent culprit in cases of pneumonia, septic arthritis (joint infections), cellulitis (infections of soft tissues), and pericarditis (infections of the membrane surrounding the heart). The *H. influenza* type B bacterium is widespread in humans and usually lives in the throat and nose without causing illness. Unvaccinated children under age 5 are at risk for HIB disease. Meningitis and other serious infections caused by *H. influenza* infection can lead to brain damage or death.

*Shigella dysenteriae* (*Shigella* dys.) is a Gram-negative rod which causes dysentary. In the colon, the bacteria enter mucosal cells and divide within mucosal cells, resulting in an extensive inflammatory response. *Shigella* infection can cause severe diarrhea which may lead to dehydration and can be dangerous for the very young, very old or chronically ill. *Shigella* dys. forms a potent toxin (shiga toxin), which is cytotoxic, enterotoxic, neurotoxic and acts as a inhibitor of protein synthesis. Resistance to antibiotics such as ampicillin and TMP-SMX has developed, however, treatment with newer, more expensive antibiotics such as ciprofloxacin, norfloxacin and enoxacin, remains effective.

*Listeria* is a genus of Gram-positive, motile bacteria found in human and animal feces. *Listeria monocytogenes* causes such diseases as listeriosis, meningoencephalitis and meningitis. This organism is one of the leading causes of death from food-borne pathogens especially in pregnant women, newborns, the elderly, and immunocompromised individuals. It is found in environments such as decaying vegetable matter, sewage, water, and soil, and it can survive extremes of both temperatures and salt concentration making it an extremely dangerous food-born pathogen, especially on food that is not reheated. The bacterium can spread from the site of infection in the intestines to the central nervous system and the fetal-placental unit. Meningitis, gastroenteritis, and septicemia can result from infection. In cattle and sheep, *listeria* infection causes encephalitis and spontaneous abortion.

*Proteus mirabilis* is an enteric, Gram-negative commensal organism, distantly related to *E. coli*. It normally colonizes the human urethra, but is an opportunistic pathogen that is the leading cause of urinary tract infections in catheterized individuals. *P. mirabilis* has two exceptional characteristics: 1) it has very rapid motility, which manifests itself as a swarming phenomenon on culture plates; and 2) it produces urease, which gives it the ability to degrade urea and survive in the genitourinary tract.

*Yersinia pestis* is the causative agent of plague (bubonic and pulmonary) a devastating disease which has killed millions worldwide. The organism can be transmitted from rats to humans through the bite of an infected flea or from human-to-human through the air during widespread infection. *Yersinia pestis* is an extremely pathogenic organism that requires very few numbers in order to cause disease, and is often lethal if left untreated. The organism is enteroinvasive, and can survive and propagate in macrophages prior to spreading systemically throughout the host.

*Bacillus anthracis* is also known as anthrax. Humans become infected when they come into contact with a contaminated animal. Anthrax is not transmitted due to person-to-person contact. The three forms of the disease reflect the sites of infection which include cutaneous (skin), pulmonary (lung), and intestinal. Pulmonary and intestinal infections are often fatal if left untreated. Spores are taken up by macrophages and become internalized into phagolysozomes (membranous compartment) whereupon germination initiates. Bacteria are released into the bloodstream once the infected macrophage lyses whereupon they rapidly multiply, spreading throughout the circulatory and lymphatic systems, a process that results in septic shock, respiratory distress and organ failure. The spores of this pathogen have been used as a terror weapon.

*Burkholderia mallei* is a Gram-negative aerobic bacterium that causes Glanders, an infectious disease that occurs primarily in horses, mules, and donkeys. It is rarely associated with human infection and is more commonly seen in domesticated animals. This organism is similar to *B. pseudomallei* and is differentiated by being nonmotile. The pathogen is host-adapted and is not found in the environment outside of its host. Glanders is often fatal if not treated with antibiotics, and transmission can occur through the air, or more commonly when in contact with infected animals. Rapid-onset pneumonia, bacteremia (spread of the organism through the blood), pustules, and death are common outcomes during infection. The virulence mechanisms are not well understood, although a type III secretion system similar to the one from *Salmonella typhimurium* is necessary. No vaccine exists for this potentially dangerous organism which is thought to have potential as a biological terror agent. The genome of this organism carries a large number of insertion sequences as compared to the related *Bukholderia pseudomallei* (below), and a large number of simple sequence repeats that may function in antigenic variation of cell surface proteins.

*Burkholderia pseudomallei* is a Gram-negative bacterium that causes meliodosis in humans and animals. Meliodosis is a disease found in certain parts of Asia, Thailand, and Australia. *B. pseudomallei* is typically a soil organism and has been recovered from rice paddies and moist tropical soil, but as an opportunistic pathogen can cause disease in susceptible individuals such as those that suffer from diabetes mellitus. The organism can exist intracellularly, and causes pneumonia and bacteremia (spread of the bacterium through the bloodstream). The latency period can be extremely long, with infection preceding disease by decades, and treatment can take months of antibiotic use, with relapse a commonly observed phenomenon. Intercellular spread can occur via induction of actin polymerization at one pole of the cell, allowing movement through the cytoplasm and from cell-to-cell. This organism carries a number of small sequence repeats which may promoter antigenic variation, similar to what was found with the *B. mallei* genome.

*Burkholderia cepacia* is a Gram-negative bacterium composed of at least seven different sub-species, including *Burkholderia multivorans, Burkholderia vietnamiensis, Burkholderia stabilis, Burkholderia cenocepacia* and *Burkholderia ambifaria*. *B. cepacia* is an important human pathogen which most often causes pneumonia in people with underlying lung disease (such as cystic fibrosis or immune problems (such as (chronic granulomatous disease). *B. cepacia* is typically found in water and soil and can survive for prolonged periods in moist environments. Person-to-person spread has been documented; as a result, many hospitals, clinics, and camps for patients with cystic fibrosis have enacted strict isolation precautions *B. cepacia*. Individuals with the bacteria are often treated in a separate area than those without to limit spread. This is because infection with *B. cepacia* can lead to a rapid decline in lung function resulting in death. Diagnosis of *B. cepacia* involves isolation of the bacteria from sputum cultures. Treatment is difficult because *B. cepacia* is naturally resistant to many common antibiotics including aminoglycosides (such as tobramycin) and polymixin B. Treatment typically includes multiple antibiotics and may include ceftazidime, doxycycline, piperacillin, chloramphenicol, and co-trimoxazole.

*Francisella tularensis* was first noticed as the causative agent of a plague-like illness that affected squirrels in Tulare County in California in the early part of the 20th century by Edward Francis. The organism now bears his namesake. The disease is called tularemia and has been noted throughout recorded history. The organism can be transmitted from infected ticks or deerflies to a human, through infected meat, or via aerosol, and thus is a potential bioterrorism agent. It is an aquatic organism, and can be found living inside protozoans, similar to what is observed with *Legionella*. It has a high infectivity rate, and can invade phagocytic and nonphagocytic cells, multiplying rapidly. Once within a macrophage, the organism can escape the phagosome and live in the cytosol.

Veterinary Applications

A healthy microflora in the gastrointestinal tract of livestock is of vital importance for health and corresponding production of associated food products. As with humans, the gastrointestinal tract of a healthy animal contains numerous types of bacteria (i.e., *E. coli, Pseudomonas aeruginosa* and *Salmonella* spp.), which live in ecological balance with one another. This balance may be disturbed by a change in diet, stress, or in response to antibiotic or other therapeutic treatment, resulting in bacterial diseases in the animals generally caused by bacteria such as *Salmonella, Campylobacter, Enterococci, Tularemia* and *E. coli*. Bacterial infection in these animals often necessitates therapeutic intervention, which has treatment costs as well being frequently associated with a decrease in productivity.

As a result, livestock are routinely treated with antibiotics to maintain the balance of flora in the gastrointestinal tract. The disadvantages of this approach are the development of antibiotic resistant bacteria and the carry over of such antibiotics and the resistant bacteria into resulting food products for human consumption.

Targets for Ameliorating a Skin Disorder

In some embodiments of the present disclosure it is contemplated that a composition comprising an ON-NP as disclosed herein is administered and regulates the expression of a target gene. In various embodiments, the composition is administered to ameliorate a skin disorder.

In some aspects, the skin disorder to be ameliorated includes, but is not limited to, a hyperproliferative disorder, a neoplastic disorder, a genetic disorder, aging, inflammation, infection, and cosmetic disfigurement. In further aspects, the skin disorder includes but is not limited to cancer. In yet further aspects, the cancer includes but is not limited to squamous cell carcinoma, basal cell carcinoma, melanoma and breast cancer. In related aspects, a gene product targeted by a composition of the present disclosure includes but is not limited to Ras, IicBa, hedgehog, B-Raf, Akt and cyclin D.

In some embodiments, a composition of the present disclosure is administered to ameliorate a genetic disorder that includes but is not limited to epidermolysis bullosa simplex, bullous ichthyosis, pachyonychia congenita, Costello syndrome and tuberous sclerosis. In some aspects, a gene product that is targeted by the administered composition is a gene product that comprises a mutation, the gene product being expressed by a gene that includes but is not limited to K5, K14, K1, K10, H-Ras, N-Ras, K-Ras, NF-kB, Akt, B-raf, ERK, Mek1, Mek2, and m-Tor.

In some embodiments, a composition of the present disclosure is administered to ameliorate an aging disorder that includes but is not limited to UV-damage and progeria. In some aspects, a gene product that is targeted by the administered composition includes but is not limited to matrix metalloproteinase-1 and progerin.

In further embodiments, a composition of the present disclosure is administered to ameliorate an inflammatory disorder that includes but is not limited to atopic dermatitis and psoriasis. In some aspects, a gene product that is targeted by the administered composition includes but is not limited to interleukin-23. In various aspects, a gene product that is targeted by the administered composition includes but is not limited to IL1-α, IL1-β, IL6, TNF-α, leukemia inhibitory factor (LIF), IFN-γ, oncostatin M (OSM), ciliary neurotrophic factor (CNTF), TGF-β, GM-CSF, IL-11, IL-12, IL-17, IL-18, IL-8.

In still further embodiments, a composition of the present disclosure is administered to ameliorate an infection. In some aspects, the infection is a viral infection. In some aspects, the infection is a bacterial infection as disclosed herein. In aspects wherein the infection is a viral infection, it is contemplated that the viral infection results in warts. In these aspects, a gene product that is targeted by the administered composition includes but is not limited to E6/E7.

In some embodiments, a composition of the present disclosure is administered to ameliorate a cosmetic disfigurement that includes but is not limited to seborrheic keratoses, epidermal nevi and pigmented nevi. In some aspects, a gene product that is targeted by the administered composition is a gene product that comprises a mutation, the gene product being expressed by a gene that includes but is not limited to FGFR3, K10 and B-Raf.

Vehicles

In some embodiments, ON-NP compositions and methods of the present disclosure comprise vehicles. As used herein, a "vehicle" is a base compound with which an oligonucleotide-functionalized nanoparticle is associated.

Vehicles useful in the compositions and methods of the present disclosure are known to those of ordinary skill in the art and include without limitation an ointment, cream, lotion, gel, foam, buffer solution or water. In some embodiments, vehicles comprise one or more additional substances including but not limited to salicylic acid, alpha-hydroxy acids, or urea that enhance the penetration through the stratum corneum.

In various aspects, vehicles contemplated for use in the compositions and methods of the present disclosure include, but are not limited to, Aquaphor® healing ointment, A+D, polyethylene glycol (PEG), glycerol, mineral oil, Vaseline Intensive Care cream (comprising mineral oil and glycerin), petroleum jelly, DML (comprising petrolatum, glycerin and PEG 20), DML (comprising petrolatum, glycerin and PEG 100), Eucerin moisturizing cream, Cetaphil (comprising petrolatum, glycerol and PEG 30), Cetaphil, CeraVe (comprising petrolatum and glycerin), CeraVe (comprising glycerin, EDTA and cholesterol), Jergens (comprising petrolatum, glycerin and mineral oil), and Nivea (comprising petrolatum, glycerin and mineral oil). One of ordinary skill in the art will understand from the above list that additional vehicles are useful in the compositions and methods of the present disclosure.

An ointment, as used herein, is a formulation of water in oil. A cream as used herein is a formulation of oil in water. In general, a lotion has more water than a cream or an ointment; a gel comprises alcohol, and a foam is a substance that is formed by trapping gas bubbles in a liquid. These terms are understood by those of ordinary skill in the art.

Nanoparticles

Nanoparticles are provided which are functionalized to have a polynucleotide attached thereto. The size, shape and chemical composition of the nanoparticles contribute to the properties of the resulting polynucleotide-functionalized nanoparticle. These properties include for example, optical properties, optoelectronic properties, electrochemical properties, electronic properties, stability in various solutions, magnetic properties, and pore and channel size variation. Mixtures of nanoparticles having different sizes, shapes and/or chemical compositions, as well as the use of nanoparticles having uniform sizes, shapes and chemical composition, and therefore a mixture of properties are contemplated. Examples of suitable particles include, without limitation, aggregate particles, isotropic (such as spherical particles), anisotropic particles (such as non-spherical rods, tetrahedral, and/or prisms) and core-shell particles, such as those described in U.S. Pat. No. 7,238,472 and International Publication No. WO 2003/08539, the disclosures of which are incorporated by reference in their entirety.

In one embodiment, the nanoparticle is metallic, and in various aspects, the nanoparticle is a colloidal metal. Thus, in various embodiments, nanoparticles of the invention include metal (including for example and without limitation, silver, gold, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials.

Also, as described in U.S. Patent Publication No 2003/0147966, nanoparticles of the invention include those that are available commercially, as well as those that are synthesized, e.g., produced from progressive nucleation in solution (e.g., by colloid reaction) or by various physical and chemical vapor deposition processes, such as sputter deposition. See, e.g., HaVashi, Vac. Sci. Technol. A5(4):1375-84 (1987); Hayashi, Physics Today, 44-60 (1987); MRS Bulletin, January 1990, 16-47. As further described in U.S. Patent Publication No. 2003/0147966, nanoparticles contemplated are alternatively produced using $HAuCl_4$ and a citrate-reducing agent, using methods known in the art. See, e.g., Marinakos et al., Adv. Mater. 11:34-37 (1999); Marinakos et al., Chem. Mater. 10: 1214-19 (1998); Enustun & Turkevich, J. Am. Chem. Soc. 85: 3317 (1963).

In some embodiments, the size of the nanoparticle is related to its ability to penetrate the skin. In general, the smaller the diameter of the nanoparticle, the deeper the penetration into or through the skin. In one aspect, the diameter of the nanoparticle allows the ON-NP to traverse the skin and enter the blood to achieve systemic delivery of the ON-NP. In another aspect, the diameter of the nanoparticle prevents the ON-NP from traversing the skin and the ON-NP is retained at the surface of the skin. In various aspects, it will be understood by one of ordinary skill in the art that the size of the nanoparticle can be adjusted to achieve a desired depth of penetration of the administered ON-NP.

Nanoparticles can range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm, from about 10 to 150 nm, from about 10 to about 100 nm, or about 10 to about 50 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or the amount of surface area that can be functionalized as described herein.

Oligonucleotides

The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases adenine (A), guanine (G), cytosine (C), thymine (T) and uracil (U). Non-naturally occurring nucleobases include, for example and without limitations, xanthine, diaminopurine, 8-oxo-N-6-methyladenine, 7-deazaxanthine, 7-deazaguanine, N4,N4-ethanocytosin, N',N'-ethano-2,6-diaminopurine, 5-methylcytosine (mC), 5-($C_3$-$C_6$)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

A modified nucleotides are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

Nanoparticles provided that are functionalized with a polynucleotide, or a modified form thereof, and a domain as defined herein, generally comprise a polynucleotide from about 5 nucleotides to about 100 nucleotides in length. More specifically, nanoparticles are functionalized with polynucleotide that are about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

In some aspects, nanoparticles with an oligonucleotide attached thereto are provided wherein an oligonucleotide further comprising a domain which affects the efficiency with which the nanoparticle is taken up by a cell is associated with the nanoparticle. Accordingly, the domain increases or decreases the efficiency. As used herein, "efficiency" refers to the number or rate of uptake of nanoparticles in/by a cell. Because the process of nanoparticles entering and exiting a cell is a dynamic one, efficiency can be increased by taking up more nanoparticles or by retaining those nanoparticles that enter the cell for a longer period of time. Similarly, efficiency can be decreased by taking up fewer nanoparticles or by retaining those nanoparticles that enter the cell for a shorter period of time.

The domain, in some aspects, is contiguous/colinear with the oligonucleotide and is located proximally with respect to a nanoparticle. In some aspects, the domain is contiguous/colinear with the oligonucleotide and is located distally with respect to a nanoparticle. The terms "proximal" and "distal" refer to a position relative to the midpoint of the oligonucleotide. In some aspects, the domain is located at an internal region within the oligonucleotide. In further aspects, the domain is located on a second oligonucleotide that is attached to a nanoparticle. Accordingly, a domain, in some embodiments, is contemplated to be attached to a nanoparticle as a separate entity from an oligonucleotide.

It is further contemplated that an oligonucleotide, in some embodiments, comprise more than one domain, located at any of the locations described herein.

The domain, in some embodiments, increases the efficiency of uptake of the oligonucleotide-functionalized nanoparticle by a cell. In some aspects, the domain comprises a sequence of thymidine residues (polyT) or uridine residues (polyU). In further aspects, the polyT or polyU sequence comprises two thymidines or uridines. In various aspects, the polyT or polyU sequence comprises 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 125, about 150, about 175, about 200, about 250, about 300, about 350, about 400, about 450, about 500 or more thymidine or uridine residues.

In some embodiments, it is contemplated that a nanoparticle functionalized with an oligonucleotide and a domain is taken up by a cell with greater efficiency than a nanoparticle functionalized with the same oligonucleotide but lacking the domain. In some aspects, a nanoparticle functionalized with an oligonucleotide and a domain is taken up by a cell 1% more efficiently than a nanoparticle functionalized with the same oligonucleotide but lacking the domain. In various aspects, a nanoparticle functionalized with an oligonucleotide and a domain is taken up by a cell 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 3%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold or higher, more efficiently than a nanoparticle functionalized with the same oligonucleotide but lacking the domain.

In some embodiments, the domain decreases the efficiency of uptake of the oligonucleotide-functionalized nanoparticle by a cell. In some aspects, the domain comprises a phosphate polymer (C3 residue) that is comprised of two phosphates. In various aspects, the C3 residue comprises 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 125, about 150, about 175, about 200, about 250, about 300, about 350, about 400, about 450, about 500 or more phosphates.

In some embodiments, it is contemplated that a nanoparticle functionalized with an oligonucleotide and a domain is taken up by a cell with lower efficiency than a nanoparticle functionalized with the same oligonucleotide but lacking the domain. In some aspects, a nanoparticle functionalized with an oligonucleotide and a domain is taken up by a cell 1% less efficiently than a nanoparticle functionalized with the same oligonucleotide but lacking the domain. In various aspects, a nanoparticle functionalized with an oligonucleotide and a domain is taken up by a cell 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold or higher, less efficiently than a nanoparticle functionalized with the same oligonucleotide but lacking the domain.

Polynucleotides contemplated for attachment to a nanoparticle include those which modulate expression of a gene product expressed from a target polynucleotide. Polynucleotides contemplated by the present disclosure include DNA, RNA and modified forms thereof as defined herein below. Accordingly, in various aspects and without limitation, polynucleotides which hybridize to a target polynucleotide and initiate a decrease in transcription or translation of the target polynucleotide, triple helix forming polynucleotides which hybridize to double-stranded polynucleotides and inhibit transcription, and ribozymes which hybridize to a target polynucleotide and inhibit translation, are contemplated.

In various aspects, if a specific polynucleotide is targeted, a single functionalized oligonucleotide-nanoparticle composition has the ability to bind to multiple copies of the same transcript. In one aspect, a nanoparticle is provided that is functionalized with identical polynucleotides, i.e., each polynucleotide has the same length and the same sequence. In other aspects, the nanoparticle is functionalized with two or more polynucleotides which are not identical, i.e., at least one of the attached polynucleotides differ from at least one other attached polynucleotide in that it has a different length and/or a different sequence. In aspects wherein different polynucleotides are attached to the nanoparticle, these different polynucleotides bind to the same single target polynucleotide but at different locations, or bind to different target polynucleotides which encode different gene products.

Modified Oligonucleotides

As discussed above, modified oligonucleotides are contemplated for functionalizing nanoparticles. In various aspects, an oligonucleotide functionalized on a nanoparticle is completely modified or partially modified. Thus, in various aspects, one or more, or all, sugar and/or one or more or all internucleotide linkages of the nucleotide units in the polynucleotide are replaced with "non-naturally occurring" groups.

In one aspect, this embodiment contemplates a peptide nucleic acid (PNA). In PNA compounds, the sugar-backbone of a polynucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

Other linkages between nucleotides and unnatural nucleotides contemplated for the disclosed polynucleotides include those described in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920; U.S. Patent Publication No. 20040219565; International Patent Publication Nos. WO 98/39352 and WO 99/14226; Mesmaeker et. al., Current Opinion in Structural Biology 5:343-355 (1995) and Susan M. Freier and Karl-Heinz Altmann, Nucleic Acids Research, 25:4429-4443 (1997), the disclosures of which are incorporated herein by reference.

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide."

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are polynucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated.

Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified polynucleotide backbones that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In still other embodiments, polynucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In various forms, the linkage between two successive monomers in the oligo consists of 2 to 4, desirably 3, groups/atoms selected from —$CH_2$—, —O—, —S—, —NRH—, >C=O, >C=NRH, >C=S, —Si(R")$_2$—, —SO—, —S(O)$_2$—, —P(O)$_2$—, —PO(BH$_3$)—, —P(O, S)—, —P(S)$_2$—, —PO(R")—, —PO(OCH$_3$)—, and —PO(NHRH)—, where RH is selected from hydrogen and C1-4-alkyl, and R" is selected from C1-6-alkyl and phenyl. Illustrative examples of such linkages are —CH$_2$—CH$_2$—CH$_2$—, —CH$_2$—CO—CH$_2$—, —CH$_2$—CHOH—CH$_2$—, —O—CH$_2$—O—, —O—CH$_2$—CH$_2$—, —O—CH$_2$—CH═ (including R5 when used as a linkage to a succeeding monomer), —CH$_2$—CH$_2$—O—, —NRH—CH$_2$—CH$_2$—, —CH$_2$—CH$_2$—NRH—, —CH$_2$—NRH—CH$_2$—, —O—CH$_2$—CH$_2$—NRH—, —NRH—CO—O—, —NRH—CO—NRH—, —NRH—CS—NRH—, —NRH—C(═NRH)—NRH—, —NRH—CO—CH$_2$—NRH—O—CO—O—, —O—CO—CH$_2$—O—, —O—CH$_2$—CO—O—, —CH$_2$—CO—NRH—, —O—CO—NRH—, —NRH—CO—CH$_2$—, —O—CH$_2$—CO—NRH—, —O—CH$_2$—CH$_2$—NRH—, —CH═N—O—, —CH$_2$—NRH—O—, —CH$_2$—O—N═ (including R5 when used as a linkage to a succeeding monomer), —CH$_2$—O—NRH—, —CO—NRH—CH$_2$—, —CH$_2$—NRH—O—, —CH$_2$—NRH—CO—, —O—NRH—CH$_2$—, —O—NRH, —O—CH$_2$—S—, —S—CH$_2$—O—, —CH$_2$—CH$_2$—S—, —O—CH$_2$—CH$_2$—S—, —S—CH$_2$—CH═ (including R5 when used as a linkage to a succeeding monomer), —S—CH$_2$—CH$_2$—CH$_2$—, —S—CH$_2$—CH$_2$—O—, —S—CH$_2$—CH$_2$—S—, —CH$_2$—S—CH$_2$—, —CH$_2$—SO—CH$_2$—, —CH$_2$—SO$_2$—CH$_2$—, —O—SO—O—, —O—S(O)$_2$—O—, —O—S(O)$_2$—CH$_2$—, —O—S(O)$_2$—NRH—, —NRH—S(O)$_2$—CH$_2$—; —O—S(O)$_2$—CH$_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHRN)—O—, —O—P(O)$_2$—NRH H—, —NRH—P(O)$_2$—O—, —O—P(O,NRH)—O—, —CH$_2$—P(O)$_2$—O—, —O—P(O)$_2$—CH$_2$—, and —O—Si(R")$_2$—O—; among which —CH$_2$—CO—NRH—, —CH$_2$—NRH—O—, —S—CH$_2$—O—, —O—P(O)$_2$—O—O—P(—O,S)—O—, —O—P(S)$_2$—O—, —NRH P(O)$_2$—O—, —O—P(O,NRH)—O—, —O—PO(R")—O—, —O—PO(CH$_3$)—O—, and —O—PO(NHRN)—O—, where RH is selected form hydrogen and C1-4-alkyl, and R" is selected from C1-6-alkyl and phenyl, are contemplated. Further illustrative examples are given in Mesmaeker et. al., 1995, Current Opinion in Structural Biology, 5: 343-355 and Susan M. Freier and Karl-Heinz Altmann, 1997, Nucleic Acids Research, vol 25: pp 4429-4443.

Still other modified forms of polynucleotides are described in detail in U.S. Patent Application No. 20040219565, the disclosure of which is incorporated by reference herein in its entirety.

Modified polynucleotides may also contain one or more substituted sugar moieties. In certain aspects, polynucleotides comprise one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C$_1$ to C$_{10}$alkyl or C$_2$ to C$_{10}$ alkenyl and alkynyl. Other embodiments include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]2, where n and m are from 1 to about 10. Other polynucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a polynucleotide, or a group for improving the pharmacodynamic properties of a polynucleotide, and other substituents having similar properties. In one aspect, a modification includes 2'-methoxyethoxy (2'-O—CH$_2$CH$_2$OCH$_3$, also known as 2'-O-(2-methoxyethyl) or 2'-MOE) (Martin et al., 1995, Helv. Chim. Acta, 78: 486-504) i.e., an alkoxyalkoxy group. Other modifications include 2'-dimethylaminooxyethoxy, i.e., a O(CH$_2$)200N(CH$_3$)$_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

Still other modifications include 2'-methoxy (2'-O—CH$_3$), 2'-aminopropoxy (2'-OCH$_2$CH$_2$CH$_2$NH$_2$), 2'-allyl (2'-CH$_2$—CH═CH$_2$), 2'-O-allyl (2'-O—CH$_2$—CH═CH$_2$) and 2'-fluoro (2'-F). The 2'-modification may be in the arabino (up) position or ribo (down) position. In one aspect, a 2'-arabino modification is 2'-F. Similar modifications may also be made at other positions on the polynucleotide, for example, at the 3' position of the sugar on the 3' terminal nucleotide or in 2'-5' linked polynucleotides and the 5' position of 5' terminal nucleotide. Polynucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects a methylene (—CH$_2$—)$_n$ group bridging the 2' oxygen atom and the 4' carbon atom wherein n is 1 or 2. LNAs and preparation thereof are described in WO 98/39352 and WO 99/14226, the disclosures of which are incorporated herein by reference.

Polypeptides

As used herein, the term "polypeptide" refers to peptides, proteins, polymers of amino acids, hormones, viruses, and antibodies that are naturally derived, synthetically produced, or recombinantly produced.

In some embodiments, the compositions of the present disclosure regulate the activity of a target polypeptide. Accordingly, in various aspects, the nanoparticle is functionalized with an aptamer. As used herein, an "aptamer" is an oligonucleotide or peptide molecule that binds to a specific target molecule. Thus, in some embodiments, the oligonucleotide-functionalized nanoparticle binds to a target polypeptide and regulates its activity.

In one aspect, the activity of the target polypeptide is inhibited by about 5% compared to a cell that is not contacted with the oligonucleotide-functionalized nanoparticle. In various aspects, the expression of the target polypeptide is inhibited by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, 99% or more compared to a cell that is not contacted with the oligonucleotide-functionalized nanoparticle. In other words, methods provided embrace those which results in any degree of inhibition of activity of a target polypeptide.

Surface Density

The density of oligonucleotides on the surface of the NP can be adjusted for a given application. For instance, work by Seferos et al. [*Nano Lett.*, 9(1): 308-311, 2009] demonstrated that the density of DNA on the NP surface affected the rate at which it was degraded by nucleases. This density modification is used, for example and without limitation, in a NP based drug delivery system where a drug and ON-NP enter cells, and the ON is degraded at a controlled rate.

Nanoparticles as provided herein have a packing density of the polynucleotides on the surface of the nanoparticle that is, in various aspects, sufficient to result in cooperative behavior between nanoparticles and between polynucleotide strands on a single nanoparticle. In another aspect, the cooperative behavior between the nanoparticles increases the resistance of the polynucleotide to nuclease degradation. In yet another aspect, the uptake of nanoparticles by a cell is influenced by the density of polynucleotides associated with the nanoparticle. As described in PCT/US2008/65366, incorporated herein by reference in its entirety, a higher density of polynucleotides on the surface of a nanoparticle is associated with an increased uptake of nanoparticles by a cell.

In some embodiments, the surface density of oligonucleotides on the surface of the NP is related to its ability to penetrate the skin. In general, a higher surface density on the surface of the ON-NP, the deeper the penetration into or through the skin. In some aspects, the surface density allows the ON-NP to traverse the skin and enter the blood to achieve systemic delivery of the ON-NP. In another aspect, the surface density prevents the ON-NP from traversing the skin and the ON-NP is retained at the surface of the skin. In various aspects, it will be understood by one of ordinary skill in the art that the surface density of oligonucleotides on the surface of the nanoparticle can be adjusted to achieve a desired depth of penetration of the administered ON-NP.

A surface density adequate to make the nanoparticles stable and the conditions necessary to obtain it for a desired combination of nanoparticles and polynucleotides can be determined empirically. Generally, a surface density of at least 2 pmoles/cm$^2$ will be adequate to provide stable nanoparticle-oligonucleotide compositions. In some aspects, the surface density is at least 15 pmoles/cm$^2$. Methods are also provided wherein the polynucleotide is bound to the nanoparticle at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more.

Oligonucleotide Attachment to a Nanoparticle

Oligonucleotides contemplated for use in the methods include those bound to the nanoparticle through any means. Regardless of the means by which the oligonucleotide is attached to the nanoparticle, attachment in various aspects is effected through a 5' linkage, a 3' linkage, some type of internal linkage, or any combination of these attachments.

Methods of attachment are known to those of ordinary skill in the art and are described in US Publication No. 2009/0209629, which is incorporated by reference herein in its entirety. Methods of attaching RNA to a nanoparticle are generally described in PCT/US2009/65822, which is incorporated by reference herein in its entirety. Accordingly, in some embodiments, the disclosure contemplates that a polynucleotide attached to a nanoparticle is RNA.

In some aspects, nanoparticles with oligonucleotides attached thereto are provided wherein an oligonucleotide further comprising a domain is associated with the nanoparticle. In some aspects, the domain is a polythymidine sequence. In other aspects, the domain is a phosphate polymer (C3 residue).

In some embodiments, the oligonucleotide attached to a nanoparticle is DNA. When DNA is attached to the nanoparticle, the DNA is comprised of a sequence that is sufficiently complementary to a target sequence of a polynucleotide such that hybridization of the DNA oligonucleotide attached to a nanoparticle and the target polynucleotide takes place, thereby associating the target polynucleotide to the nanoparticle. The DNA in various aspects is single stranded or double-stranded, as long as the double-stranded molecule also includes a single strand sequence that hybridizes to a single strand sequence of the target polynucleotide. In some aspects, hybridization of the oligonucleotide functionalized on the nanoparticle can form a triplex structure with a double-stranded target polynucleotide. In another aspect, a triplex structure can be formed by hybridization of a double-stranded oligonucleotide functionalized on a nanoparticle to a single-stranded target polynucleotide.

Spacers

In certain aspects, functionalized nanoparticles are contemplated which include those wherein an oligonucleotide and a domain are attached to the nanoparticle through a spacer. "Spacer" as used herein means a moiety that does not participate in modulating gene expression per se but which serves to increase distance between the nanoparticle and the functional oligonucleotide, or to increase distance between individual oligonucleotides when attached to the nanoparticle in multiple copies. Thus, spacers are contemplated being located between individual oligonucleotides in tandem, whether the oligonucleotides have the same sequence or have different sequences. In aspects of the invention where a domain is attached directly to a nanoparticle, the domain is optionally functionalized to the nanoparticle through a spacer. In aspects wherein domains in tandem are functionalized to a nanoparticle, spacers are optionally between some or all of the domain units in the tandem structure. In one aspect, the spacer when present is an organic moiety. In another aspect, the spacer is a polymer, including but not limited to a water-soluble polymer, a nucleic acid, a polypeptide, an oligosaccharide, a carbohydrate, a lipid, an ethylglycol, or combinations thereof.

In certain aspects, the polynucleotide has a spacer through which it is covalently bound to the nanoparticles. These polynucleotides are the same polynucleotides as described above. As a result of the binding of the spacer to the nanoparticles, the polynucleotide is spaced away from the surface of the nanoparticles and is more accessible for hybridization with its target. In instances wherein the spacer is a polynucleotide, the length of the spacer in various embodiments at least about 10 nucleotides, 10-30 nucleotides, or even greater than 30 nucleotides. The spacer may have any sequence which does not interfere with the ability of the polynucleotides to become bound to the nanoparticles or to the target polynucleotide. The spacers should not have sequences complementary to each other or to that of the oligonucleotides, but may be all or in part complementary to the target polynucleotide. In certain aspects, the bases of the polynucleotide spacer are all adenines, all thymines, all cytidines, all guanines, all uracils, or all some other modified base.

EXAMPLES

Example 1

Preparation of Nanoparticles

Citrate-stabilized gold nanoparticles (from 1-250 nm) are prepared using published procedures [G. Frens, Nature Physical Science. 1973, 241, 20]. While a 13 and 5 nm size is used in this example, other examples include nanoparticles in size from 1 nm to 500 nm. Briefly, hydrogen tetrachloroaurate is reduced by treatment with citrate in refluxing water. The particle size and dispersity can be confirmed using transmission electron microscopy and uv/vis spectrophotometry. Thiolated oligonucleotides are synthesized using standard solid-phase phosphoramidite methodology [Pon, R. T. Solid-phase supports for oligonucleotide synthesis. Methods in Molecular Biology (Totowa, N.J., United States) (1993), 20 (Protocols for Oligonucleotides and Analogs), 465-496]. The thiol-modified oligonucleotides are next added to 13±1 and 5 nm gold colloids at a concentration of 3 nmol of oligonucleotide per 1 mL of 10 nM colloid and shaken overnight. After 12 hours, sodium dodecylsulphate (SDS) solution (10%) is added to the mixture to achieve a 0.1% SDS concentration, phosphate buffer (0.1 M; pH=7.4) is added to the mixture to achieve a 0.01 phosphate concentration, and sodium chloride solution (2.0 M) is added to the mixture to achieve a 0.1 M sodium chloride concentration. Six aliquots of sodium chloride solution (2.0 M) are then added to the mixture over an eight-hour period to achieve a final sodium chloride concentration of 0.3 M, and shaken overnight to complete the functionalization process. The solution is centrifuged (13,000 rpm, 20 min) and resuspended in sterile phosphate buffered saline three times to produce the purified conjugates.

Example 2

Oligonucleotide Modified Nanoparticle Conjugate Methods

Oligonucleotide design in this example includes two possible mechanisms of action. First, a sequence was designed using the published plasmid sequence that would preferentially hybridize to the sense strand of the promoter site for the Ampicillin resistance (AmpR) gene β-lactamase. This would sensitize the bacteria to ampicillin by taking advantage of the preferential hybridization of the conjugate (imparted by more favorable binding constant and/or intracellular concentration of the particles) to the promoter sequence of AmpR in the bacterial genome. This would prevent the promoter complex from binding to its target site and prevent transcription of the mRNA transcript (Amp resistance gene), therefore sensitizing the bacteria to ampicillin. The sequences used were 5'-AT TGT CTC ATG AGC GGA TAC ATA TTT GAA AAA AAA AAA A-SH-3' (SEQ ID NO: 1) and 5'-AT TGT CTC ATG AGC GGA TAC AAA AAA AAA A-SH-3' (SEQ ID NO: 2).

A second strategy would utilize a sequence designed to hybridize to an internal region of the AmpR gene. In doing so, this would prevent the completion of the full mRNA transcript. The downstream effect of this is to prevent complete transcription of functional mRNA transcript (Amp resistance gene) and therefore sensitize bacteria to ampicillin. For this strategy, a sense strand was chosen to hybridize to the target duplex DNA. The sequence for this was 5'-ACT TTT AAA GTT CTG CTA TAA AAA AAA AA-SH-3' (SEQ ID NO: 3). A scheme for both strategies is presented in FIG. 1. Alternatively, one could use traditional antisense strategy to bind mRNA and prevent protein production, thus sensitizing the bacteria to antibiotics.

JM109 E. coli competent cells were transformed using an ampicillin containing plasmid (either psiCHECK 2, Promega or pScreen-iT, Invitrogen) according to published procedures (Promega and Invitrogen) and grown on antibiotic-containing (Amp) plates. A single colony was selected and grown in liquid culture with ampicillin for twelve hours. This culture was used to form a frozen (10% glycerol) stock for use in subsequent experiments.

Figure 2:
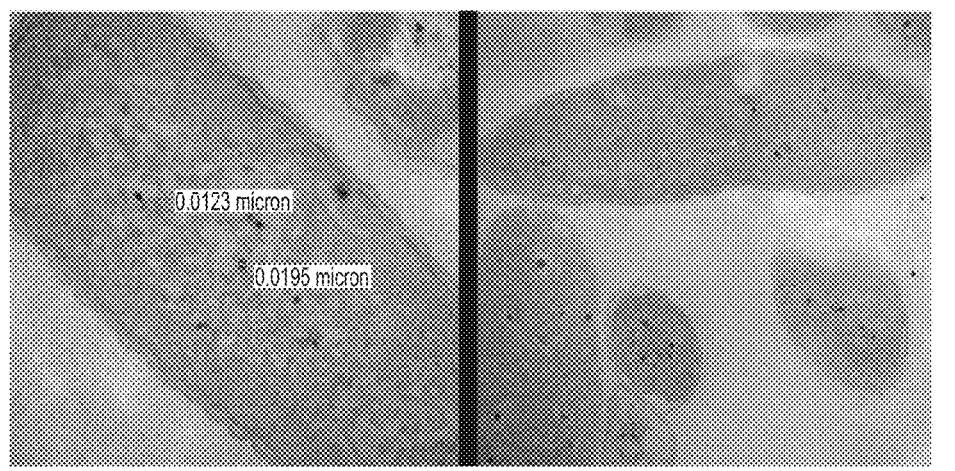
FIG. 2 depicts electron microscopy images of E. coli following conjugate treatment.
Figure 2:
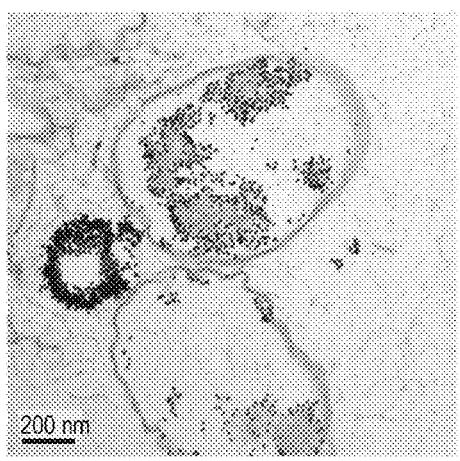
Figure 2:
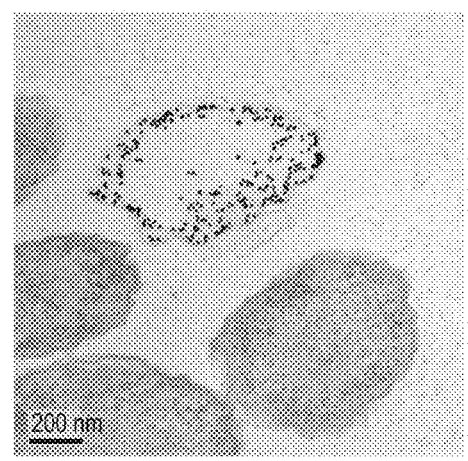

After thawing stocks of E. coli, a small volume was grown in liquid broth either with or without ampicillin as detailed below, and plated on corresponding LB plates. In one example, 5 μL of frozen bacterial broth was grown in 1 mL of LB broth with 30 nM particles for 5.5 hrs. From this 1 mL, 100 μL was plated and grown overnight. Bacterial entry was confirmed using transmission electron microscopy (FIG. 2).

After several hours of treatment with nanoparticles, a small volume of bacteria is plated on either ampicillin positive or ampicillin negative plates. The bacteria are grown on these plates for an additional twelve hours, and the number of colonies grown under each condition is evaluated. The results are summarized below in Table 1, below. A 66% inhibition of bacterial growth was obtained using this strategy. Routine optimization of conditions is expected to yield a 100% successful sensitization of bacteria.

TABLE 1

| Growth Conditions | Trial | | | Expected Growth |
| --- | --- | --- | --- | --- |
| | 1 | 2 | 3 | |
| E. coli (−) Amp (−) Nanoparticle (−) | NA | NA | NA | (−) |
| E. coli (−) Amp (+) Nanoparticle (−) | (−) | (−) | (−) | (−) |

TABLE 1-continued

| | | | | |
|---|---|---|---|---|
| E. coli (+) Amp (−) NonsenseNP (+) | NA | NA | NA | (+) |
| E. coli (+) Amp (+) NonsenseNP (+) | NA | NA | NA | (+) |
| E. coli (+) Amp (−) PromotorNP (+) | (+) | (+) | (−) | (+) |
| E. coli (+) Amp (+) PromotorNP (+) | (−) | (−) | (−) | (−) |
| E. coli (+) Amp (−) InternalNP (+) | (+) | (+) | (−) | (+) |
| E. coli (+) Amp (+) InternalNP (+) | (−) | (−) | (−) | (−) |

Protocol: 5 µL bacterial broth in 1 mL broth with 30 nM particles grown for 3.5 hrs. Plating of 100 µL and grown overnight.

| | | | | |
|---|---|---|---|---|
| E. coli (−) Amp (−) Nanoparticle (−) | (−) | (−) | (−) | (−) |
| E. coli (−) Amp (+) Nanoparticle (−) | (−) | (−) | (−) | (−) |
| E. coli (+) Amp (−) NonsenseNP (+) | (+) | (+) | (+) | (+) |
| E. coli (+) Amp (+) NonsenseNP (+) | (+) | (+) | (+) | (+) |
| E. coli (+) Amp (−) PromotorNP (+) | (+) | (+) | (+) | (+) |
| E. coli (+) Amp (+) PromotorNP (+) | (−) | (−) | (+) | (−) |
| E. coli (+) Amp (−) InternalNP (+) | (+) | (+) | (+) | (+) |
| E. coli (+) Amp (+) InternalNP (+) | (+) | (+) | (+) | (−) |

Protocol: 5 µL bacterial broth in 1 mL broth with 30 nM particles grown for 5.5 hrs. Plating of 100 µL and grown overnight.

Example 3

Figure 3:
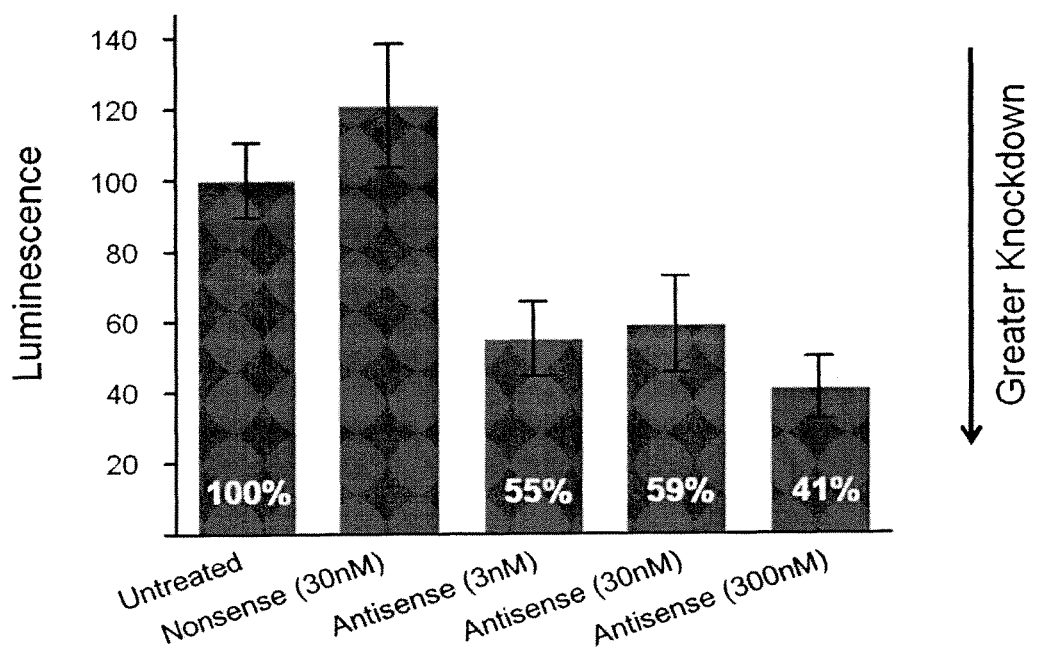
FIG. 3 depicts a summary of results for the inhibition of bacterial luciferase expression using nanoparticles. Nonsense denotes a sequence with no complementary region on the E. coli genome or transfected plasmid. Antisense denotes a sequence targeting luciferase. Relative luciferase activity is shown as percentages within the bars, normalized to renilla expression.

Oligonucleotide Modified Nanoparticle Conjugates Achieve Transcriptional Knockdown An additional strategy was employed to examine transcriptional knockdown in a plasmid derived Luciferase gene. This model was used to demonstrate site-selective gene knock down by differentiating Luciferase knockdown from a separate region on the plasmid encoding *Renilla* expression. To assay this effect the Dual-Luciferase Reporter Assay System (Promega) was used. The strategy employed for this model was to block formation of a full mRNA transcript of the luciferase gene. This results in diminution of luciferase signal in relation to *renilla*. The sequence used for this was 5'-CCC GAG CAA CGC AAA CGC AAA AAA AAA AA-SH-3' (SEQ ID NO: 4). Alternatively, one could use a strategy similar to that used above to block the promoter complex from binding its target site. In this example, 5 nm particles were used. The resulting knockdown after 12 hours was 59% using 300 nM concentration of particles (p value=0.0004). These results demonstrate another method of achieving gene regulation at the transcriptional level. A summary of the data is shown in FIG. 3.

Example 4

Oligonucleotide Modified Nanoparticle Conjugate Blocking of Transcription

Figure 4:
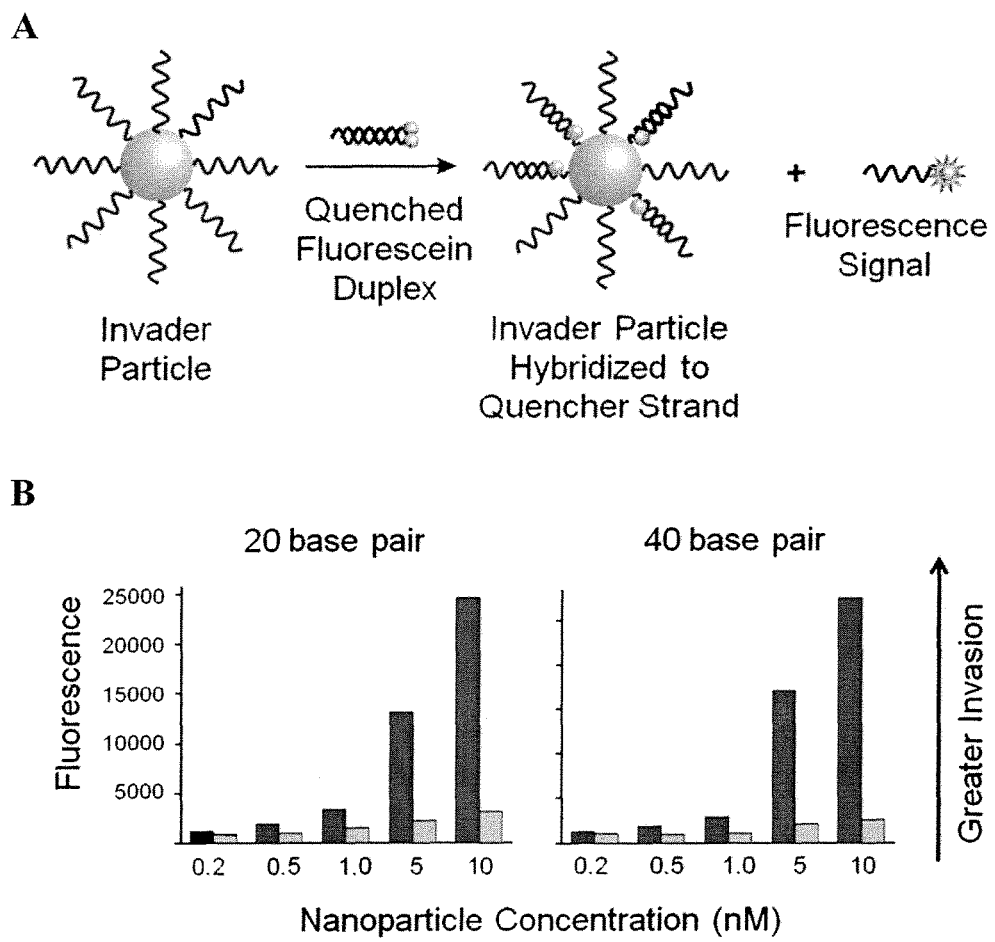
FIG. 4 depicts the duplex invasion scheme. A) Schematic of invasion of a duplex (fluorescein and adjacent dabcyl at terminus of duplex) by nanoparticle thereby releasing fluorescence signal. B) Results demonstrating increasing fluorescence with duplex invasion, both in short (20 base pair) duplexes and long (40 base pair) duplexes (Gray boxes represent nonsense sequences, Black boxes represent antisense sequences).

As a demonstration of these conjugates' ability to block transcription and subsequent protein production by hybridizing with double stranded genomic DNA, an in vitro transcription assay was conducted. Oligonucleotide functionalized gold nanoparticles were added in an in vitro transcription reaction (Promega) that contained double-stranded plasmid DNA encoding the luciferase gene. The oligonucleotide sequence targeted the sense strand of luciferase gene, thus could only block transcription and not translation. As a control, nanoparticle conjugates functionalized with non-complementary sequence was also used in an identical manner. The transcription reaction was allowed to proceed and luciferase activity was measured using a commercial kit (Promega). In the samples that contained nanoparticle conjugates that targeted the luciferase gene, a significant reduction in luciferase activity (>75%) was observed compared to control reactions that contained nanoparticle conjugates with non-complementary sequences;

Additionally, to elucidate the underlying principle of knockdown, experiments were conducted in buffer to examine oligonucleotide gold nanoparticle conjugate invasion of a preformed duplex. A schematic and the resulting data are shown in FIG. 4 (A and B). The particle may bind a preformed duplex (triplex formation). Alternatively, the particle may displace a preformed duplex via its higher binding constant for the target sequence. The particles are then centrifuged at 13,000 RPM, washed 3 times in PBS, and oxidized with KCN. Fluorescence of bound strands is measured. Without being bound by theory, this is hypothesized to result in the release of a fluorescein-capped oligonucleotide (antisense strand) and an increase in fluorescence signal. Prior to nanoparticle addition, a duplex with quencher (dabcyl, sense strand) and fluorophore (fluorescein, antisense strand) are formed. Over a range of concentrations, sequence specificity for this strategy can be seen.

Example 5

Gene Suppression without Toxicity in vitro

Both DNA-Au NPs and siRNA-Au NPs have been shown to suppress gene function in multiple cells in vitro. For example, siRNA-Au NPs directed against survivin led to cell death of T-24 and HT-1376 bladder cancer cells. In addition, siRNA-Au NPs progressively decreased the expression of luciferase in HeLa cells over 4 days in culture after a single treatment, while luciferase expression returned to baseline levels by 4 days after treatment with conventional siRNA [Giljohann et al., J Am Chem Soc 131: 2072-2073 (2009)]. Cell toxicity is not observed at concentrations required for gene silencing, and immune-mediated effects are markedly lower than that of conventional nucleic acids. Concurrent suppression of more than one gene with the oligonucleotide-Au NPs has also been shown; simultaneously adding DNA-Au NPs against two enzymes of ganglioside biosynthesis (GM2/GD2 synthase and GD3 synthase) to cultured keratinocytes (KCs) led to accumulation of the GM3 substrate at the keratinocyte membrane by 3 days after initiation, with persistence of visible membrane expression for at least a week after antisense blockade.

To examine cellular responses to these nanoconjugates, 13 nm citrate stabilized gold nanoparticles and oligonucleotide-modified particles were compared. While citrate stabilized particles induce significant changes in the gene expression profile of HeLa cells (127 genes up or down regulated), scrambled siRNA or DNA functionalized nanoparticles show no significant changes in the gene expression profile.

Example 6

Nanoparticle Conjugates are Delivered Transdermally after Topical Application Studies using a DNA-Au NP or siRNA-Au NP indicate that primary human keratinocytes take up DNA-Au NPs and siRNA-Au NPs at ~100% efficiency within 2 hours. Using inductively coupled plasma mass spectroscopy (ICP-MS) to measure gold particle uptake [Giljohannet al., Nano Lett 7: 3818-3821 (2007)], the uptake by cultured keratinocytes of DNA-Au NPs was found to be at least 10-fold greater than the uptake of any other cells, and the uptake of siRNA-Au NPs into KCs was up to 20-fold higher than other cell types. For example, incubation of 50 pM siRNA-Au NPs for 6 h with KCs in low calcium medium leads to uptake of approximately $6 \times 10^5$ NPs per cell, much higher than cell uptake with conventional siRNAs.

Figure 5:
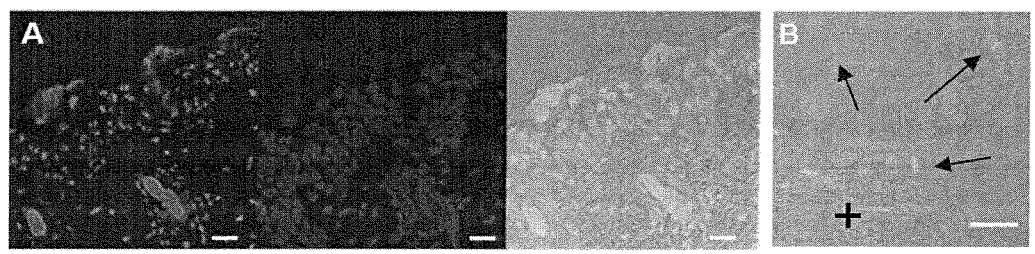
FIG. 5 depicts penetration of approximately 25 nM siRNA-gold nanoparticles into the epidermis, dermis, and subcutaneous tissues within 24 hours after application. A) Confocal imaging of siRNA-Au NPs in mouse skin. Left panel=Cy3. The bright color is the stratum corneum (outer skin layer), which may be brightly fluorescent both because of dense particle accumulation and autofluorescence; The hair (seen in longitudinal section within follicles) also is intensely fluorescent; Middle=DAPI staining of nuclei; Right=Overlap image. The image shows the uptake of fluorescent siRNA-Au NPs in ~100% of epidermal cells. B) Adipocytes (arrows) and fibroblasts of the underlying mesenchymal tissue (+) also take up fluorescent particles almost universally. Bar=20 μm.

A group of potential ointments, creams and lotions for topical delivery were identified that ensured easy mixing, retention at the applied site, and stability of the nanoconjugate (as determined by persistence of the characteristic red color of the nanoparticles). Application of Cy5-labelled sense DNA-Au NP ointment (DNA-Au NPs in Aquaphor ointment®) to dorsal mouse skin showed penetration through stratum corneum to the epidermis by 2 h, penetration to the upper dermis by 6-8 h, and widespread distribution throughout the dermis by 24 and 48 h after a single application. The demonstrated persistence of fluorescence correlated well with persistence of the gold nanoparticles in tissue as measured by ICP-MS. Similarly, Cy3-modified siRNA-Au NP ointment was taken up rapidly through mouse skin, showing excellent penetration to the base of the epidermis, through the dermis and into subcutaneous tissues by 24 h after application (FIGS. 5A, B). These studies showed that the nanoparticles penetrated the stratum corneum, traversed the epidermis, and reached the dermis with its vasculature.

Topical application has shown no evidence of toxicity. Application of 15 nM scrambled siRNA-Au NP for 1 month to the dorsal skin of C57BL/6 mice led to no observed systemic or cutaneous clinical change. In comparison with controls (application of vehicle or untreated), gold particle accumulation was most notable in sites of melanoma metastases: skin, lymph nodes, lungs and, to a lesser extent, liver and kidneys. Histologic sections showed no inflammation, evidence of apoptosis or alteration in proliferation/thickness of skin. In preliminary toxicology studies, mice were treated daily for 10 days with topically applied scrambled siRNA-Au NPs at dosages ranging from 50 nM to 500 nM (n=5 in each group). Gold particles were detected in skin, lymph nodes, liver, GI tract and feces, with concentrations increasing in these organs in proportion to the concentration of applied nanoparticles.

Example 7

Topically Applied siRNA-Au NPs Suppress Gene Expression

Figure 6:
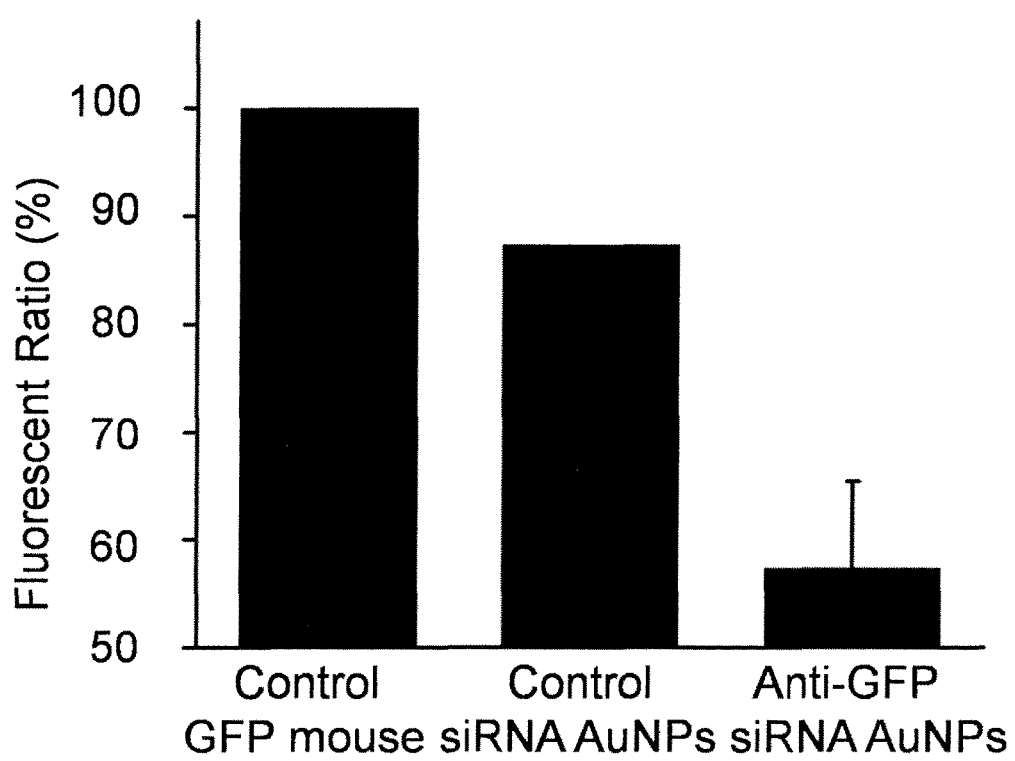
FIG. 6 depicts GFP knockdown in C57BL/6-Tg(UBC-GFP)30Scha/J mice after 4 weeks of treatment with siRNA-Au NPs.

In studies to target gene expression using a topical approach, green fluorescent protein (GFP) was targeted in mice ubiquitously expressing the transgene ($C_{57}BL/6$-Tg (UBC-GFP)30Scha/J). siRNA-Au NPs directed against GFP were applied at 15 nM concentration topically using the Aquaphor vehicle. The mice were treated serially three times weekly for four weeks, with a half of the dorsum of the mouse treated with anti-GFP siRNA-Au NPs and the other half treated with scrambled siRNA-Au NPs. After isolating the treated skin, fluorimetry was used to compare GFP levels between controls and those treated with the anti-GFP siRNA-Au NPs. In treated mice (n=5), this regime resulted in a 43% decrease in GFP expression as measured fluorescently ($p<0.0036$) (FIG. 6) The approximately 12% knockdown seen from the skin in mice treated on one half with scrambled (control) siRNA-Au NPs reflected systemic uptake of the anti-GFP siRNA-Au NPs.

Example 8

Metastatic Melanoma as a Therapeutic Target

Through the study of human melanoma cell lines of different genotypes (e.g., SK– MEL-28, 1205Lu, A375P, C8161, and WM3211 lines) and human melanoma tissue, metastatic cells have been found to be distinguishable from non-metastasizing melanoma cells and normal melanocytes by the presence of a unique de-acetylated form of ganglioside GM3. de-N-acetylGM3 is not only an antigenically distinct marker, but also drives cell migration and invasion [Liu J de-N-acetyl GM3 promotes melanoma cell migration and invasion via urokinase plasminogen activator receptor signaling-dependent matrix metalloproteinase-2 activation. Cancer Res (2009)]. Studies with explant mouse models have verified the value of de-N-acetylGM3 in suppressing the spread of metastasis of metastatic lines in mice to the lungs and liver. During these studies the time course of establishment of cutaneous and metastatic melanomas was explored in explant models with SK-MEL-28 and 1205Lu, two BRAF V600E/PTEN loss models. In these models, subcutaneous inoculation of $10^6$ cells lead to skin tumors and metastases to the lung and liver in the majority of mice within a few weeks after inoculation by gross, microscopic and RT-PCR evaluation. The ability of siRNA-Au NPs to penetrate into melanoma cells and suppress the expression of survivin was also studied. Using an SK-MEL 28 melanoma cell line, siRNA Au-NPs were shown to decrease survivin mRNA levels by 91% as measured by quantitative reverse transcriptase-polymerase chain reaction (qRT-PCR).

Example 9

Multifunctional siRNA-Au NPs for Targeting Known Genes Involved in Metastatic Melanoma Using a Combinatorial In Vitro Approach The ability of multifunctional nanoparticles to genetically target signaling pathways in melanoma is examined. The conjugates are designed and demonstrated to target multiple mutations in a combinatorial manner. Using a ratio-metric approach, functionalized conjugates are optimized for the purposes of concurrently regulating multiple genes.

Multiple signaling pathways are known to be upregulated in metastatic melanomas, particularly BRAF/ERK and AKT3 signaling. A common BRAF mutation and the activated AKT3 are targeted using a combinatorial approach. In addition, the results of knockdown by the BRAF V600E and AKT3 siRNA-Au NPs is compared with the results of non-complementary control siRNA-Au NPs in each experiment. This determines the specificity of gene knockdown and allows for assessments of conjugate toxicity.

The optimal strategy for targeting these two melanoma targets independently is determined. First, siRNA conjugates are designed to target the T1799A (V600E) mutation in BRAF. At least three sequences per target are designed using siRNA design algorithms or via selection from literature [Sharma et al., Cancer Res 65: 2412-2421 (2005)]. BRAF conjugates are individually assessed to determine optimal concentrations for gene knockdown in the BrafVE Ptenlox mouse cell line, 3 human BRAF V600E-containing cell lines (A375P; SK-MEL-28; 1205Lu) and, as negative controls, normal melanocytes (ScienCell Research Labs, Carlsbad, Calif.) and the C8161 metastatic melanoma cell line that shows only wildtype BRAF (see Table A).

A second sequence is designed to target AKT3 [Sharma et al., Clin Cancer Res 15: 1674-1685 (2009)], and is tested in the 3 BRAF V600E-containing cell lines, the C8161 line that also has AKT activation and, as a control, normal human melanocytes. Cells from the transgenic mouse line are grown in the presence of 4-HT (and, as a control, without 4-HT) to induce BrafVE expression. qRT-PCR and Western blot analysis is used after harvesting of cells at specific time points after siRNA-Au NP treatment to determine levels of mRNA and protein expression of human and mouse BRAF V600E and AKT3 [Dankort et al., Nat Genet. 41: 544-552 (2009); Dankort et al., Genes Dev 21: 379-384 (2007)]. To confirm the specificity of knockdown, the effects of siRNA-Au NP treatment is evaluated on wildtype BRAF, CRAF, AKT1 and AKT2 by qRT-PCR and immunoblotting [Stahl et al., Cancer Res 64: 7002-7010 (2004)]. The technique also allows targeting of the less frequent mutations that lead to increased ERK activation, such as in NRAS (e.g., Q61L) or in c-KIT.

Since the gold nanoparticle acts as a scaffold for molecule attachment, the use of a combinatorial approach to simultaneously target BRAF V600E and AKT3 is examined. siRNA duplexes targeting each mutation will be added to the nanoparticles in different ratios. Using the ability to control the stoichiometry of the conjugate, the delivery of siRNA to cells is precisely affected, allowing for investigation of knockdown and cellular response as the amounts of each target are fine tuned.

Example 10

Assessments of Signaling Pathway Alterations and Cell Function

The effects on signaling and cell biologic behavior of selected individual and multifunctional siRNA-Au NPs are compared as described [Sun et al., J Invest Dermatol 119: 107-117 (2002); Wang et al., J Invest Dermatol 126: 2687-2696 (2006); Wang et al., J Biol Chem 276: 44504-44511 (2001); Wang et al., J Biol Chem 278: 25591-25599 (2003)]. BRAF V600E/AKT3 siRNA-Au NPs suppresses both ERK phosphorylation, and AKT expression and phosphorylation. This is confirmed through immunoblotting with antibodies directed against pERK, ERK, pAKT, and AKT. Given the key role of BRAF/ERK and AKT signaling in increased melanoma cell proliferation and survival, a marked alteration in melanoma cell function in vitro occurs as a result of knockdown. Induction of apoptosis is determined by immunoblotting to assess PARP cleavage and by annexin V flow studies. The relative roles of BRAF V600E suppression and AKT3 suppression is dissected by determining protein expression of Bim (induced by BRAF activation), BCL-2 (induced by AKT activation) and BAD (suppressed by AKT activation). Lack of induced apoptosis in controls with scrambled sequences assures that apoptosis results from intended targeting rather than siRNA-Au NP toxicity. Proliferation is assessed by cell counts and WST-1 [(4-[3-(4-iodophenyl)-2-(4-nitrophenyl)-2H-5-tetrazolio]-1,3-benzene disulfonate)] assays, and cyclin D1 expression is evaluated by immunoblotting. Melanoma cells express factors that contribute to angiogenesis (particularly IL-8 and VEGF) and invasion (particularly MMP-2) [Liu J et al., de-N-acetyl GM3 promotes melanoma cell migration and invasion via urokinase plasminogen activator receptor signaling-dependent matrix metalloproteinase-2 activation. Cancer Res (2009)]. Expression of tumor VEGF, Hif-1α and MMP-2 is assessed by immunoblotting cell extracts and supernatants; to assess MMP-2 function zymography assays of culture supernatants are performed as previously described [Liu J et al., de-N-acetyl GM3 promotes melanoma cell migration and invasion via urokinase plasminogen activator receptor signaling-dependent matrix metalloproteinase-2 activation. Cancer Res (2009); Wang et al., J Biol Chem 278: 25591-25599 (2003)]. IL-8 expression is assessed in cell supernatants by ELISA [Crawford et al., Mol Cancer Ther 7: 492-499 (2008)]. Cell invasion assays are performed using Matrigel Invasion Chambers [Wang et al., J Biol Chem 278: 25591-25599 (2003)].

The multifunctional siRNA-AuNPs provide the opportunity to target alternative gene mutations (such as in the WM1366 cell line) or to add additional targeting siRNA's to the multifunctional siRNA-Au NPs targeting BRAF V600E and AKT3. The ability to target three or more genes using genetic profiles of each of the cell lines as well as their known genetic mutations is therefore contemplated (Table A). For example, both SK-MEL-28 and 1205Lu cells have specific CDK4 point mutations; although these mutations do not seem to affect the response to BRAF suppression, additional targeting allows exploration of the functional effect of these mutations. Similarly, SK-MEL-28 and 1205Lu have additional signature mutations in p53 (SK-MEL-28) and CDKN2A (1205Lu) that are targeted to explore their significance in metastatic melanoma transformation and progression. These cell lines have both been used extensively for in vivo xenograft models.

Example 11

Conditions, Safety and Biodistribution for Transdermal and Intravenous Delivery of siRNA Nanoconjugates The delivery, clearance, and toxicity of scrambled siRNA-Au NPs administered intravenously and transdermally is compared in an immunocompetent mouse. In addition, toxicity and pharmacokinetic profiles of the conjugates are assessed. The multifunctional nanoparticles are also optimized for penetration through human skin as described herein above.

siRNA-Au NPs are delivered systemically by transdermal delivery, and their fate is tracked by the deposition of gold particles. Levels of gold particles in organs is measured by ICP-MS as previously described [Giljohann et al., Nano Lett 7: 3818-3821 (2007)]. In these studies, 6 mice are studied in each siRNA-Au NP treatment group with vehicle applied as a control in 2 mice for each parameter. In biodistribution studies, delivery is focused to the liver, lungs, skin and lymph nodes, the most common sites of melanoma metastases and sites reached by siRNA-Au NPs in studies with topical administration. The kidney, spleen, adrenals and GI tract (sites of potential toxicity) are also monitored; and the brain (an occasional site of metastasis in humans that is difficult to reach). 500 nM siRNA-Au NP is administered in these studies, since this concentration reaches internal targets well through transdermal delivery.

Transdermal Delivery

Widespread uptake of 25 nM fluorophore-conjugated siRNA-Au NPs by epidermal, dermal and subcutaneous cells has been demonstrated within 24 h after application (FIG. 5), and delivery of gold particles to the skin, lymph nodes, lungs, liver and kidney, even after application of only 15 nM unifunctional siRNA-Au NPs. Studies are performed in immunocompetent $C_{57}BL/6$ mice at 7-8 weeks of age, the age at which treatment starts in the transgenic mouse melanoma model.

Delivery, Clearance and Toxicity with Single Administration

A time course experiment with the multifunctional siRNA-Au NPs is performed to determine: 1) the time course and efficiency of transdermal penetration; 2) the efficacy of delivery to internal organs; 3) the clearance after a single application; and 4) the potential for irritation or toxicity. Mice are treated once and then euthanized at 8 timepoints from 2 h to 7 weeks post-treatment. In these studies, the distribution of siRNA-Au NP at the early timepoints (i.e. 2, 4, 24, and 72 h) is compared to assure penetration through skin, delivery to organs, and clearance. In mice treated topically, the treated site of skin is trisected for histological analysis to assure lack of toxicity, for ICP-MS to quantify gold particle concentration, and for storage at $-80°$ C. (e.g., for later ELISA assays). The skin section for ICP-MS is subjected to a brief exposure to $60°$ C. water to separate epidermis from the vascularized dermis and thereby determine epidermal versus dermal/subcutaneous delivery. At sacrifice, organs (as noted above) and distant skin are assessed for gold content by ICP-MS, and a portion of each organ is taken for histologic assessment (see below).

Accumulation with Repeated Administration

Given that mice are treated repeatedly in the proposed experiments, rather than just a single application, these studies are also performed with mice treated 2-3 times weekly (based on the persistence of gold particles in skin after single application) for 10 days, 4 weeks and 7 weeks to quantify gold particle accumulation.

Assessment for Toxicity

Mice are weighed every other day as well as observed for visible skin alterations or behavioral change. To test for adverse effects, histologic and immunohistochemical evaluations are performed at the organ level. Specifically, the presence of necrosis and inflammation in all tissues and, in the skin, alterations in epidermal maturation and the presence melanoderma (pigment dumping) is determined. If evidence of cutaneous or visceral atrophy is seen, cell proliferation is assessed immunohistochemically by detection of Ki67. The presence of suspected apoptosis is confirmed immunohistochemically (ApopTag In Situ Apoptosis Detection) [Lannutti et al., Cancer Res. 57(23): 5277-80 (1997)]. If epidermal apoptosis is seen in treated skin, ELISA assays for TNF-alpha expression are performed in siRNA-Au NP skin vs. control-treated skin, given that the skin is an innate immune organ and able to express pro-apoptotic cytokines.

Blood is obtained from cardiac puncture pre-terminally in all animals. In the single dose studies, the serum is frozen for future analysis if needed. Blood from mice treated for 10 days or more is analyzed for blood counts, aspartate aminotransferase (liver function) and creatinine levels (kidney function)(Charles River Labs).

Transdermal Delivery in Human Skin

The ability of the siRNA-Au NPs to traverse human skin is tested by using normal human skin from abdominoplasties to conduct in vitro experiments with Franz diffusion cells. These Franz cells have been the gold standard for testing flux through human skin for the past few decades. They are temperature- and humidity-controlled to match human in vivo conditions and, importantly, provide an osmotic gradient simulating skin. The transit of the gold particles through human skin is quantified by ICP-MS as a marker for penetration, since the siRNA and gold particles remain conjugated. Reconstituted skin is obtained after separating the stratum corneum/epidermis from the dermis. The integrity of reconstituted human skin samples is verified visually under a dissecting microscope. To further verify that tissue is intact, receptor fluid samples are collected in the first 30 minutes with the assumption that gold is not detectable in samples collected within the first thirty minutes if tissue is intact. After mounting skin onto Franz cells, siRNA-Au NPs (beginning with 500 nM and decreasing to as low as 100 pM) are applied with Aquaphor as a control. Studies are performed in at least triplicate and at least three times. These studies indicate the flux through human epidermis, the amount of drug passing across a $cm^2$ of skin surface over time ($ng/cm^2/h$). At the end of 6 hours and 24 hours, the skin is minced and gold particles extracted for ICP-MS measurements to measure the residual Au NPs in tissue.

Example 12

Establishment of the Mouse Model

Melanomas are induced by topical administration of 5 mM 4-HT in DMSO at 6 weeks of age to the left and right flank areas on 3 consecutive days, as previously described [Dankort et al., Nat Genet. 41: 544-552 (2009)]. These highly pigmented melanomas will first be apparent at 7-10 days after 4-HT administration in the transgenic model as highly pigmented tumors [Dankort et al., Nat Genet. 41: 544-552 (2009)]. In studies to generate the mouse model, application of solvent alone is used as a control. To simulate human disease, in which therapy would not begin until at least the skin tumor is first detectable, initiation of therapy is withheld in both mouse models until the melanoma is visible or palpable with a minimal area of at least 5 $mm^2$.

Dose-finding Studies

Eight mice are tested at each of 3 doses between 50 nM and 500 nM. Controls in the dose-finding studies include scrambled siRNA and Aquaphor alone. Mice are sacrificed at 7 weeks after initiation of therapy for necropsy. The primary melanoma(s) and any cutaneous metastases are photographed and the volume(s) are measured at the time of each treatment by calipers. The number of visible or palpable cutaneous metastases are noted. Gross metastases of the lungs, liver, lymph nodes, kidneys and brain are counted (facilitated by their dark brown color), and organs are examined histologically with multiple sections throughout each organ for evidence of micrometastases. Micrometastases are easily visible microscopically, but a Fontana-Masson stain is used to further accentuate the pigmentation if needed. The dosage that is most effective in reducing metastases without any evidence of toxicity is used for subsequent studies.

Time Course of Development of Metastases and its Alteration by siRNA-Au NP Therapy Mice are administered siRNA-Au NPs, scrambled siRNA-Au NPs or control vehicle (topical Aquaphor) with a dosage and frequency based on previous studies. Sets of 8 mice each are sacrificed at 1, 3, 5, and 7 weeks after initiation of therapy to evaluate visceral metastasis grossly and histologically as described above.

Mechanism of the Effect of siRNA-Au NPs

The primary tumors are divided for routine histologic and immunohistochemical studies, immunoblot analysis, and qPCR. Controls in these studies are tumors from mice treated with scrambled siRNA-Au NPs or vehicle and normal/untreated skin (e.g., skin from the upper back in the transgenic mouse). The following is investigated: i) tumor cell proliferation with Ki67 staining; ii) peritumoral vascularity with anti-CD31 antibody; iii) tumor cell apoptosis with TUNEL assay or caspase 3 staining; iv) the direct suppression of expression of BrafVE, wildtype Braf, and Akt3 in the transgenic model using qPCR with primers as previously described [Dankort et al., Nat Genet. 41: 544-552 (2009); Sharma et al., Clin Cancer Res 15: 1674-1685 (2009); Sharma et al., Cancer Res 66: 8200-8209 (2006); Sharma et al., Cancer Res 65: 2412-2421 (2005)]; and v) changes in protein expression of total Braf; Craf; p-Akt/total Akt; and p-ERK½/total ERK12. Extracted protein from tumor samples is assayed for markers of angiogenesis and invasion (VEGF, MMP-2 and Hif-1) by immunoblotting. Baseline retrobulbar bleeding and cardiac puncture at sacrifice 2 h after the last administration of siRNA-Au NPs is performed to assess IL-8 levels by ELISA [Crawford et al., Mol Cancer Ther 7: 492-499 (2008)]. In the immunocompetent transgenic model, whether suppression of Braf and/or Akt3 activation impact the immune response and promote cytotoxic T cell function is also assessed. These studies compare cells from untreated or scrambled siRNA-Au NP treated mice with BrafVE Akt3 siRNA-Au NP-treated transgenic mice. Using immunohistochemistry, the number of Foxp3+ (regulatory T cells) and CTLA4+/CD152 (cytotoxic CD8+ T cells) are counted in tumor sections. To ensure visualization of antibody, AEC chromogen (red color) is used. Tumor-infiltrating lymphocytes are extracted from skin tumors [Lin et al., J Immunol 182: 6095-6104 (2009)] and from mice sacrificed at 1, 4, and 7 weeks after initiation of therapy. Cells are subjected to FACS analysis after staining with fluorochrome-conjugated antibodies against CD4, CD25, Foxp3, CD8 and CTLA4.

Persistence of siRNA Suppression

In separate studies mice are treated with siRNA-Au NPs for 7 weeks to control primary tumor growth and metastases. Therapy is discontinued in half of the mice (n=12). Mice without treatment and a cohort with continuing treatment are sacrificed 2, 4, 8 and 12 weeks later. The primary melanoma is measured twice weekly and visceral metastases are counted at termination. In addition, Au-NPs are quantified in the skin and visceral tumors to determine how their clearance correlates with reversal of tumor suppression.

Prolongation of Survival

Transgenic mice require euthanasia by 25-50 days [Dankort et al., Nat Genet. 41: 544-552 (2009)](e.g., when either the tumor reaches 2 cm at its maximal diameter or the mouse is morbid, such as showing poor feeding, loss of 20% of body weight in one week or 10% of body weight in two consecutive weeks, abnormal respiration, or posture indicating pain). In the studies described above to assess the effect of siRNA-Au NPs, mice are sacrificed at time points up to 10 weeks. Treatment of mice continues and a comparison to untreated and scrambled siRNA-Au NP-treated mice is performed for survival studies of up to 3 months. Mouse survival is plotted using Kaplan-Meier survival curves.

Assessment of Toxicity

Mice are weighed every other day and observed for evidence of altered behavior or appetite. Liver and kidney tissues are assessed for evidence of tissue toxicity (e.g., apoptosis or inflammation) by routine histopathological staining, and screening blood studies for bone marrow, hepatic and renal function are performed according to methods known in the art. Additional immunohistochemical evaluation (such as TUNEL and Ki67) is performed if evidence of toxicity is suspected. siRNA-induced off-target effects is assessed in serum obtained by cardiac puncture to performing Whole Genome arrays (Affymetrix). Gene array studies are performed in at least triplicate on samples from mice exposed for at least 7 weeks to BrafVE Akt 3 siRNA-Au NPs and their controls; samples are banked and arrays performed on mice with shorter exposures if off-target effects are detected.

Statistical Analyses

The ability of synthesized conjugates to knockdown genes and affect protein expression is assessed using the two-tailed Student's t test with significance at $P<0.05$. The significance of differences in the size of cutaneous melanomas and number of lung and liver metastases is determined using the nonparametric Mann-Whitney U-test and PRISM software. Significance in survival studies is determined by logrank tests of the survival plots.

While the present invention has been described in terms of various embodiments and examples, it is understood that variations and improvements will occur to those skilled in the art. Therefore, only such limitations as appear in the claims should be placed on the invention.

Example 13

Applicants have incorporated a portion of Example 3 (page 47, line 29 -page 50, line 14 in its entirety) from PCT/US2008/065366 as follows.

In addition to quantitative measurements, we also investigated the size and surface potential of the particles before and after exposure to cell culture conditions to gain insight into how they were interacting with the extracellular environment. Dynamic light scattering (DLS) measurements were performed to estimate the initial measured hydrodynamic radius of the ASNPs. DLS data show that the average diameter of an ASNP functionalized with only DNA (approximately 80 strands; 13 nm Au NP) is 42 ±1 nm while that of a fully OEG-functionalized particle is 27 ±1 nm. Interestingly, the average size of the DNA-functionalized particles increases to 76 ±3 nm upon exposure to cell culture media, while the size of the OEG functionalized particle remains relatively constant (Table 2). This observation suggests that in cell culture media alone, some components are attracted to the ASNPs, which results in an increase in size.

TABLE 2

ASNP characteristics before and after media exposure.

| Oligonucleotide Strands/AuNP | Diameter (nm) | | Surface potential (mV) | | Adsorbed proteins/ASNP |
|---|---|---|---|---|---|
| | before media | after media | before media | after media | |
| 79 ± 2 | 42 ± 1 | 76 ± 3 | −21 ± 4 | −13 ± 1 | 23 ± 3 |
| 32 ± 1 | 56 ± 2 | 77 ± 2 | −36 ± 2 | −24 ± 2 | 14 ± 1 |
| 7 ± 1 | 38 ± 1 | 50 ± 2 | −34 ± 2 | −27 ± 1 | 10 ± 1 |
| 0 | 27 ± 1 | 30 ± 1 | −20 ± 1 | −19 ± 1 | 2 ± 3 |

Zeta potential measurements indicate a change in surface potential that accompanies the size change of the ASNP, which we hypothesize is due to positively charged serum proteins binding to the DNA shell on the Au NPs (Table 2). Initially, the surface potential of the ASNPs in non-serum containing media was −21 ±4 mV. After exposure to media containing proteins, the ASNPs became more positively charged at −13 ±1 mV. In contrast, Au NPs functionalized with OEG did not show a change in surface potential after exposure to serum containing media. While ASNPs appear to become associated with serum proteins, the OEG particles do not. This is consistent with the well-characterized passivation properties of OEG monolayers with respect to protein adsorption (Prime et al., 1991 Science 252(5009): 1164-1167).

Further analysis using a fluorescence-based assay for protein quantification was carried out and confirmed that the observed size and surface potential changes were due to protein adsorption on the ASNP surface. Additionally, this assay allowed for an estimate of the number of proteins that are attached to each particle. ASNPs (final concentration 6 nM) were incubated both in serum-containing media and serum-free media for 24 hrs at 37° C. After this treatment, ASNPs were isolated from solution via three consecutive centrifugation steps (13,000 rpm, 20 min) and washed with PBS buffer to remove unbound proteins, and finally the Au NPs were dissolved with KCN (2.5 mM final concentration). A Quant-iT fluorescence protein assay (Invitrogen) was used to determine the relative number of proteins in the solution. Estimation of the number of bound proteins per ASNP was calculated using a standard curve and an assumed average protein size of 60kD. In the case of a fully DNA-functionalized Au NP (80 strands per 13 nm particle), approximately 23proteins remain attached to each particle after separation from the media (assuming an average protein is 60kD). As the number of oligonucleotides per particle decreases, so does the number of proteins per particle (Table 2). These numbers may be interpreted as minimum values, as the washing process to remove unbound proteins could remove weakly bound proteins from the ASNPs. Nonetheless, the assay allows for comparison of particles functionalized with varying numbers of oligonucleotides, and it confirms that the density of oligonucleotides directly correlates with the number of proteins, providing one possible reason for the increasing numbers of ASNPs as a function of the DNA loading in the case of particles exposed to cell culture media. While others have looked at the contribution of non-specific serum proteins to the uptake of citrate stabilized Au NPs (Chithrani et al., 2006 Nano Letters 6(4): 662-668), the number of proteins as a determining factor in the uptake of Au NPs has not yet been established. Data presented herein show that specific surface modification by oligonucleotides can be used to control the number of proteins and hence control cellular interactions of Au NP agents and perhaps materials in general. The measurements demonstrate that the quantity of ASNPs associated with each cell is significant, and orders of magnitude larger than what has been observed for non-functionalized, protein or peptide-modified Au NPs (Liu et al., 2007 Analytical Chemistry 79(6): 2221-2229).

In summary, based on literature precedent and the negative charge presented by the DNA functionalization, this uptake ability would not be anticipated. To test the contribution of the oligonucleotides present on the nanoparticle surface to their cellular uptake, the density of oligonucleotides on the surface was varied using OEG as a diluent. Even at high concentrations, it was found that Au NPs functionalized with only OEG showed comparatively little internalization by the cell models studied. The data indicate that the number of proteins increases with the number of oligonucleotides on the surface, reaching a maximum of 23 proteins/particle. Further, their subsequent uptake correlates well with the number of absorbed proteins. The uptake plateau at 60 oligonucleotides per particle is perhaps due to a saturation of proteins on the surface of the oligonucleotide layer. Beyond this point, additional oligonucleotides may confer no additional ability to recruit proteins. Compared to other particles and traditional transfection agents, the differences in uptake of ASNPs may be due to both the number and nature of the proteins which are attracted to the oligonucleotides on the ASNPs.

Thus, in the co-functionalized particles the oligonucleotides provide the contribution to cellular internalization. By increasing the number of oligonucleotides, increased uptake of the ASNPs was observed, with a maximum uptake reached at loadings of approximately 60 oligonucleotides per Au NP. These data show that the surface density of oligonucleotides mediate the amount of nanoparticles internalized by cells.

What is claimed is:

1. A method of inhibiting gene expression comprising the step of:
   administering a therapeutically effective amount of a composition comprising a dermal vehicle and a spherical oligonucleotide-functionalized nanoparticle having a net negative charge to human skin under conditions wherein the oligonucleotide-functionalized nanoparticle hybridizes to a target polynucleotide and inhibits gene expression,
   wherein the nanoparticle is from about 5 nanometers (nm) to about 50 nm in mean diameter,
   wherein gene expression is inhibited by about 10% or more,
   and wherein oligonucleotides are covalently associated with the nanoparticle at a surface density of at least 2 pmol/cm$^2$.

2. The method of claim 1 wherein the target polynucleotide is RNA.

3. The method of claim 1 wherein the administration of the composition ameliorates a skin disorder.

4. The method of claim 3 wherein the skin disorder is selected from the group consisting of cancer, a genetic disorder, an aging disorder, inflammation, infection, and cosmetic disfigurement.

5. The method of claim 4 wherein the cancer is selected from the group consisting of squamous cell carcinoma, basal cell carcinoma, breast cancer and melanoma.

6. The method of claim 4 wherein the genetic disorder is selected from the group consisting of epidermolysis bullosa simplex, bullous ichthyosis, pachyonychia congenita, Costello syndrome and tuberous sclerosis.

7. The method of claim 4 wherein the aging disorder is selected from the group consisting of UV-damage and progeria.

8. The method of claim 4 wherein the inflammation is due to psoriasis.

9. The method of claim 8 wherein the target is interleukin-23.

10. The method of claim 4 wherein the infection is selected from the group consisting of viral infection and bacterial infection.

11. The method of claim 4 wherein the cosmetic disfigurement is selected from the group consisting of seborrheic keratoses, epidermal nevi and pigmented nevi.

12. The method of claim 11 wherein the target is a gene product comprising a mutation, said gene product being expressed by a gene selected from the group consisting of FGFR3, K10 and B-Raf.

13. The method of claim 1 wherein gene expression is inhibited by about 20%, about 30%, about 40%, about 50%, about 60%, about 65%, about 70%, about 75%, about 80%, about 85%, about 90%, about 95%, 99%, or more compared to gene expression in the absence of administration of the composition.

14. The method of claim 1 wherein the nanoparticle is a gold nanoparticle.

15. The method of claim 1, said dermal vehicle comprising an ointment.

16. The method of claim 15 wherein the ointment is Aquaphor.

17. The method of claim 1 wherein each oligonucleotide is from about 5 to about 100 nucleotides in length.

18. The method of claim 1 wherein each oligonucleotide is from about 5 to about 50 nucleotides in length.

19. The method of claim 1 wherein oligonucleotides are covalently associated with the nanoparticle at a surface density of at least 4 $pmol/cm^2$.

20. The method of claim 1 wherein oligonucleotides are covalently associated with the nanoparticle at a surface density of 4 $pmol/cm^2$.

21. The method of claim 1 wherein the oligonucleotide comprises a spacer through which the oligonucleotide is covalently bound to the nanoparticle.

22. The method of claim 21 wherein the spacer is a polynucleotide spacer that is at least 10 nucleotides in length.

* * * * *

UNITED STATES PATENT AND TRADEMARK OFFICE
CERTIFICATE OF CORRECTION

PATENT NO. : 10,098,958 B2  
APPLICATION NO. : 13/721366  
DATED : October 16, 2018  
INVENTOR(S) : Chad A. Mirkin et al.

Page 1 of 1

It is certified that error appears in the above-identified patent and that said Letters Patent is hereby corrected as shown below:

On the Title Page

Item (72), Line 3, "Chicago, CA (US)" should be -- Chicago, IL (US) --.

Signed and Sealed this  
Twenty-sixth Day of February, 2019

Andrei Iancu  
*Director of the United States Patent and Trademark Office*

UNITED STATES PATENT AND TRADEMARK OFFICE
CERTIFICATE OF CORRECTION

PATENT NO. : 10,098,958 B2  
APPLICATION NO. : 13/721366  
DATED : October 16, 2018  
INVENTOR(S) : Chad A. Mirkin et al.

Page 1 of 1

It is certified that error appears in the above-identified patent and that said Letters Patent is hereby corrected as shown below:

In the Specification

At Column 1, Line 21:
"This invention was made with government support under Grant Numbers 5DP1 OD000285 and U54 CA119341, awarded by the National Institutes of Health (NIH). The government has certain rights in the invention."
Should read:
"This invention was made with government support under grant number OD000285 awarded by the National Institutes of Health. The government has certain rights in the invention."

Signed and Sealed this  
Twelfth Day of April, 2022

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 4

<210> SEQ ID NO 1
<211> LENGTH: 39
<212> TYPE: DNA
<213> ORGANISM: Artificial Sequence

```
<220> FEATURE:
<223> OTHER INFORMATION: Synthetic polynucleotide
<220> FEATURE:
<221> NAME/KEY: modified_base
<222> LOCATION: (39)..(39)
<223> OTHER INFORMATION: Thiol

<400> SEQUENCE: 1
attgtctcat gagcggatac atatttgaaa aaaaaaaaa                           39

<210> SEQ ID NO 2
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (30)..(30)
<223> OTHER INFORMATION: Thiol

<400> SEQUENCE: 2
attgtctcat gagcggatac aaaaaaaaaa                                     30

<210> SEQ ID NO 3
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (29)..(29)
<223> OTHER INFORMATION: Thiol

<400> SEQUENCE: 3
acttttaaag ttctgctata aaaaaaaaa                                      29

<210> SEQ ID NO 4
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (29)..(29)
<223> OTHER INFORMATION: Thiol

<400> SEQUENCE: 4
cccgagcaac gcaaacgcaa aaaaaaaaa                                      29
```